(12) United States Patent  (10) Patent No.: US 8,728,631 B2
Kitano et al.  (45) Date of Patent: May 20, 2014

(54) DENDRIMER COMPOUND AND ORGANIC LUMINESCENT DEVICE EMPLOYING THE SAME

(75) Inventors: Makoto Kitano, Auderghem (BE); Yoshiaki Tsubata, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1423 days.

(21) Appl. No.: 10/571,568

(22) PCT Filed: Sep. 10, 2004

(86) PCT No.: PCT/JP2004/013585
§ 371 (c)(1),
(2), (4) Date: Aug. 15, 2006

(87) PCT Pub. No.: WO2005/026144
PCT Pub. Date: Mar. 24, 2005

(65) Prior Publication Data
US 2007/0154732 A1   Jul. 5, 2007

(30) Foreign Application Priority Data

Sep. 12, 2003 (JP) .................... 2003-321522

(51) Int. Cl.
*H01L 51/50* (2006.01)
(52) U.S. Cl.
USPC ........... 428/680; 428/917; 313/504; 313/505; 313/506; 257/40; 257/E51.05; 257/E51.026; 257/E51.032; 548/304.1; 548/418; 548/440
(58) Field of Classification Search
USPC .................. 428/690, 917; 313/504, 506, 507; 257/40, E51.05, E51.026, E51.032; 548/418, 440, 304.1
See application file for complete search history.

(56) References Cited

U.S. PATENT DOCUMENTS

| 5,041,516 A | 8/1991 | Frechet et al. |
| 2002/0072583 A1 | 6/2002 | Miki et al. |

FOREIGN PATENT DOCUMENTS

| EP | 1 238 981 A2 * | 9/2002 |
| EP | 1437395 A2 | 7/2004 |
| EP | 1532158 B1 | 10/2008 |
| JP | 11-40871 A | 2/1999 |

(Continued)

OTHER PUBLICATIONS

Goto et. al., Synthesis a Novel Dendrimer, 2001, Chemistry Letters, p. 1204-1205.*

(Continued)

*Primary Examiner* — Gregory Clark
(74) *Attorney, Agent, or Firm* — Sughrue Mion, PLLC

(57) ABSTRACT

A dendrimer compound characterized by comprising a core represented by the following formula (1-1), (1-2), (1-3), or (1-4) and at least one kind of dendritic structure selected among dendritic structures represented by the following formulae (3) and (4).

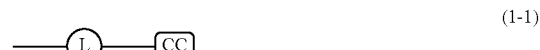

(1-1)

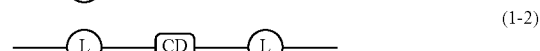

(1-2)

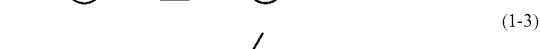

(1-3)

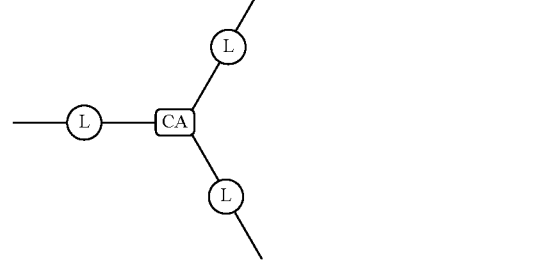

(1-4)

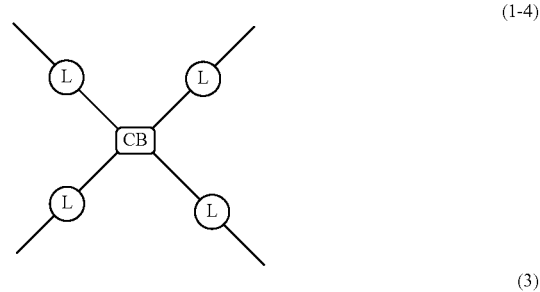

(3)

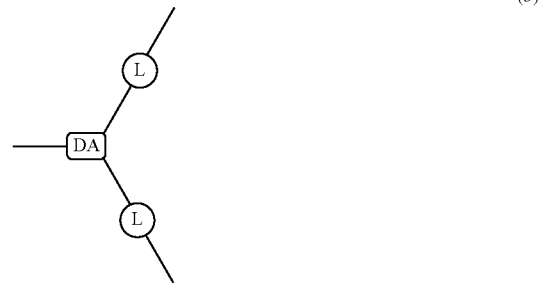

(4)

27 Claims, No Drawings

(56) References Cited

FOREIGN PATENT DOCUMENTS

| | | |
|---|---|---|
| JP | 11-140180 A | 5/1999 |
| JP | 11-171812 A | 6/1999 |
| JP | 2003-514970 | 4/2003 |
| JP | 2003-231741 A | 8/2003 |
| JP | 2004-2703 A | 1/2004 |
| JP | 2004-43544 A | 2/2004 |
| JP | 2004-59899 | 2/2004 |
| JP | 2004-131694 | 4/2004 |
| JP | 2004-315679 A | 11/2004 |
| TW | 200300770 A | 6/2003 |
| WO | 02/066552 | 8/2002 |
| WO | WO 02/067343 A1 | 8/2002 |
| WO | WO 03/044877 A2 | 5/2003 |

OTHER PUBLICATIONS

Sanchez-Delgado et. al., Similtaneous Thiophenes Iridium, 1993, Inorganic Chemistry, vol. 32, pp. 3766-3770.*

Budd et al., An Efficient and Selective Monohydrido Rhodium (I) Homogeneous Hydrogenation Catalyst containing a Cyclic Phosphine, 1974, Canadian Journal of Chemistry, vol. 52, pp. 775-781.*

Rauchfuss et al., One Step Closer to Structural Models for HDS Catalysts: Oxo Complexes of Re(V), 1995, Inorganic Chemistry, vol. 34, pp. 5220-5225.*

M. Kimura et al., "Construction of Regulated Nanospace around a Porphyrin Core", *J. Am. Chem. Soc.*, vol. 123, 2001, pp. 5636-5642.

M. Kimura et al., "Energy transfer within ruthenium-cored rigid metallodendrimers", *Tetrahedron Letters*, vol. 41, 2000, pp. 6809-6813.

Bosman et al., "About Dendrimers: Structure, Physical Properties, and Applications," Chem. Rev.. 99:1665-1688 (1999).

Taiwanese Intellectual Property Office, "Rejection Decision Letter," issued in connection with Taiwanese Patent Application No. 093127396, dated Mar. 30, 2012.

Official Action issued on Jun. 26, 2012 in German Patent Application No. 11 2004 001 675.4 with English translation.

* cited by examiner

DENDRIMER COMPOUND AND ORGANIC LUMINESCENT DEVICE EMPLOYING THE SAME

TECHNICAL FIELD

The present invention relates to a dendrimer compound, a raw material compound thereof and an organic luminescent device (hereinafter sometimes referred to as an organic LED) in which the dendrimer compound is used.

BACKGROUND ART

High molecular weight luminescent materials and high molecular weight charge transport materials have been variously studied since they are soluble in solvents unlike low molecular weight materials and thus can be formed into a luminescent layer or a charge transport layer of a luminescent device by coating.

Linear polymers are generally known as such high molecular weight materials.

On the other hand, applications of dendrimer compounds having a specific polymer structure to luminescent materials and charge transport materials have been recently reported (Patent Documents 1, 2, 3).

Patent Document 1 JP-A-11-40871
Patent Document 2 JP-A-11-171812
Patent Document 3 W002/067343

DISCLOSURE OF THE INVENTION

Problems to be Solved by the Invention

An object of the present invention is to provide a novel dendrimer compound useful as a luminescent material or a charge transport material, a raw material compound thereof and an organic luminescent device in which the dendrimer compound is used.

Means for Solving the Problems

The present inventors have conducted intensive studies to solve the above-described problem and as a result, have found that a dendrimer compound having a structure represented by the following formula (5) is useful as a luminescent material and a charge transport material, and the present invention has been completed.

Accordingly, the present invention is as follows.
(i) The present invention relates to a dendrimer compound characterized by comprising a core represented by the following formula (1-1), (1-2), (1-3) or (1-4) and at least one dendritic structure selected from dendritic structures represented by the following formula (3) or (4). The present invention also relates to a polymer compound characterized by comprising the dendrimer bonded to an atom constituting the main chain structure or a side chain of the polymer compound.

The dendrimer compound is characterized by comprising a core represented by the following formula (1-1), (1-2), (1-3) or (1-4) and at least one dendritic structure selected from dendritic structures represented by the following formula (3) or (4):

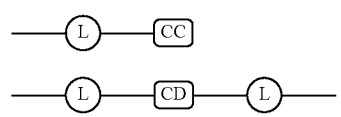

(1-1)

(1-2)

(1-1)

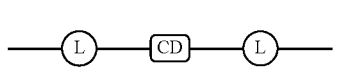

(1-2)

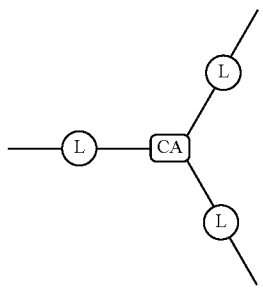

(1-3)

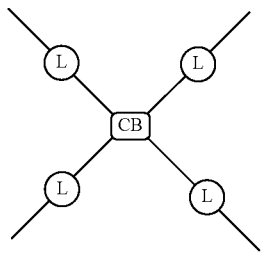

(1-4)

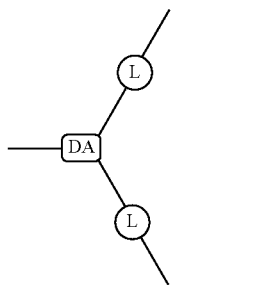

(3)

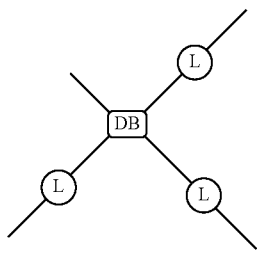

(4)

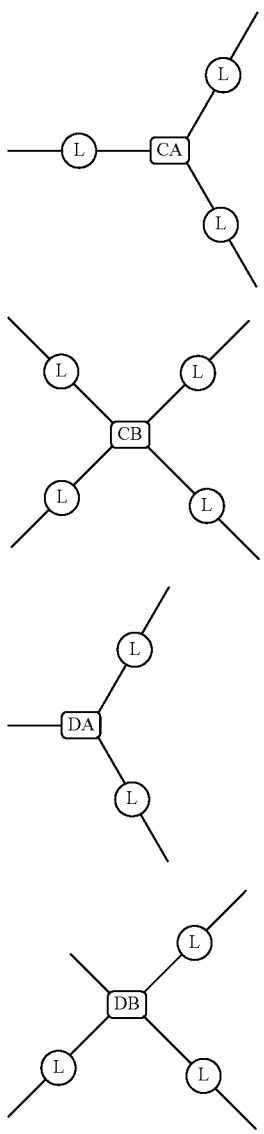

(1-3)

(1-4)

(3)

(4)

wherein a unit CA, a unit CB, a unit CC and a unit CD each independently represent an aromatic ring, a metal complex structure, a structure represented by the following formula (5):

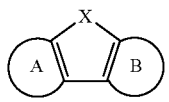

(5)

wherein a ring A and a ring B each independently represent an aromatic ring, X represents —O—, —S—, —S(=O)—, —SO$_2$—, —B(R$_1$)—, —Si(R$_2$)(R$_3$)—, —P(R$_4$)— or —PR$_5$ (=O)—, and R$_1$, R$_2$, R$_3$, R$_4$ and R$_5$ each independently represent a substituent selected from an alkyl group, an alkoxy group, an alkylthio group, an aryl group, an aryloxy group, an arylthio group, an arylalkyl group, an arylalkoxy group, an arylalkylthio group, an arylalkenyl group, arylalkynyl group, an amino group, a substituted amino group and a monovalent heterocyclic group, or a structure in which two or more structures selected from an aromatic ring, a metal complex structure and a structure represented by the following formula (5), which may be the same or different, are bonded directly or via a divalent group shown in the following (L-1):

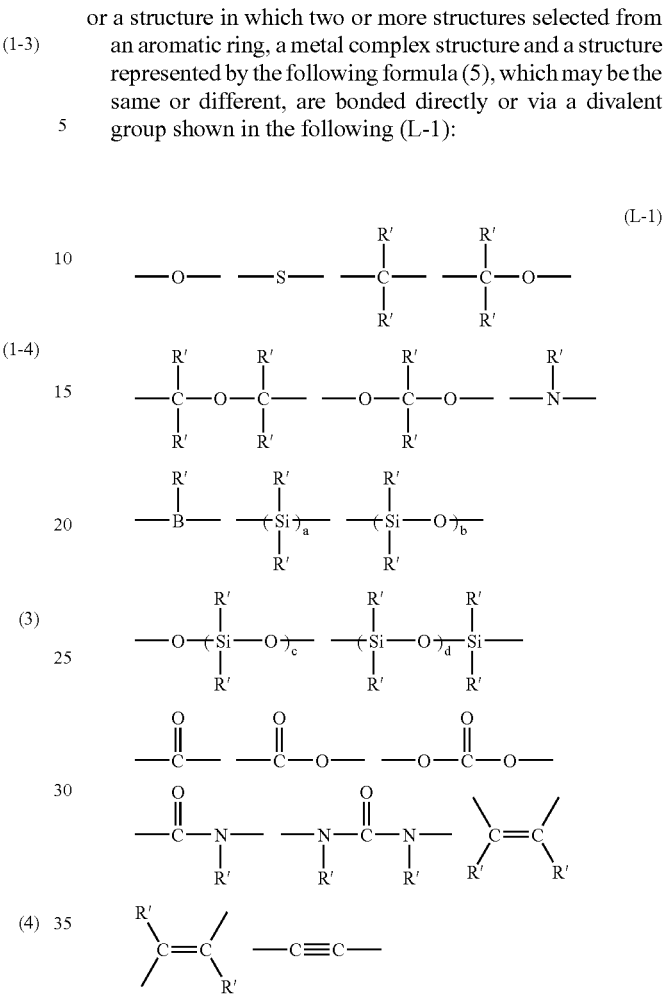

(L-1)

wherein R' represents a group selected from a hydrogen atom, an alkyl group, an alkoxy group, an aryl group and an aryloxy group, and when a plurality of R's are present, R's may be the same or different; a, b and c each independently represent an integer of 1 to 12; and d represents an integer of 1 to 11;

a unit DA and a unit DB each independently represent an aromatic ring, a metal complex structure, a structure represented by the following formula (5), or a structure in which two or more structures selected from an aromatic ring, a metal complex structure and a structure represented by the following formula (5), which may be the same or different, are bonded; at least one of the core and the dendritic structure contains a structure represented by the formula (5), and L is a direct bond or a linking group selected from the following (L-2):

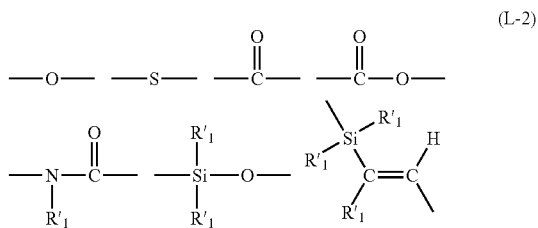

(L-2)

-continued

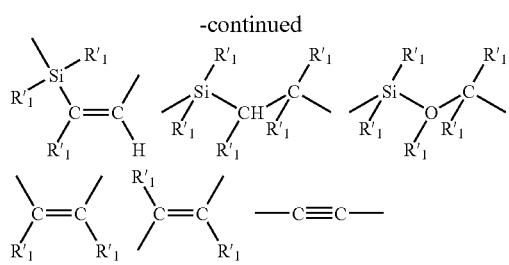

wherein $R_1'$ represents a hydrogen atom, an alkyl group, an alkoxy group, an aryl group or an aryloxy group, and when a plurality of $R_1$'s are present, $R_1$'s may be the same or different.

(ii) The dendrimer compound according to the above (i), wherein the unit CC contains a metal complex structure.

(iii) The dendrimer compound according to the above (i), wherein the unit CD contains a metal complex structure.

(iv) The dendrimer compound according to the above (i), wherein the unit CA or the unit CB contains a metal complex structure.

(v) The dendrimer compound according to any one of the above (i) to (iv), whose number of generations is 1 to 5.

(vi) The dendrimer compound according to any one of the above (i) to (v), comprising a chemical structure in which at least one dendritic structure selected from dendritic structures represented by the formula (3) and the formula (4) is regularly repeated.

(vii) The dendrimer compound according to any one of the above (i) to (vi), wherein the core represented by the formula (1-2) is represented by the following formula (6-1), (6-2) or (6-3):

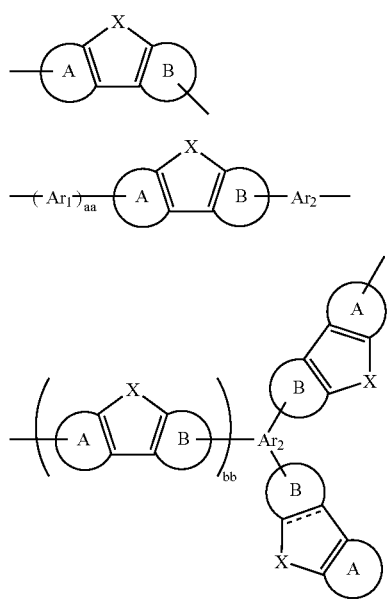

wherein the ring A, the ring B and X are as defined above; $Ar_1$ represents a divalent aromatic ring or a divalent metal complex structure; $Ar_2$ represents a trivalent aromatic ring or a trivalent metal complex structure; and aa and bb each independently represent 0 or 1.

(viii) The dendrimer compound according to any one of the above (i) to (vi), wherein the core represented by the formula (1-3) is represented by the following formula (7-1), (7-2) or (7-3):

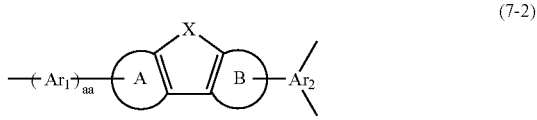

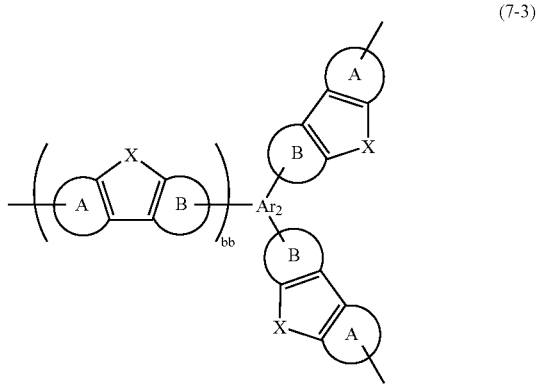

wherein the ring A, the ring B and X are as defined above; $Ar_1$ represents a divalent aromatic ring or a divalent metal complex structure; $Ar_2$ represents a trivalent aromatic ring or a trivalent metal complex structure; and aa and bb each independently represent 0 or 1.

(ix) The dendrimer compound according to any one of the above (i) to (vi), wherein the core represented by the formula (1-4) is represented by the following formula (8-1), (8-2), (8-3) or (8-4):

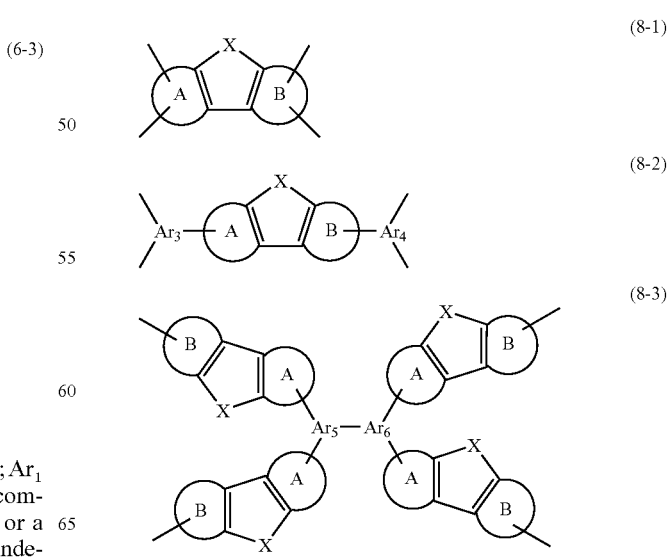

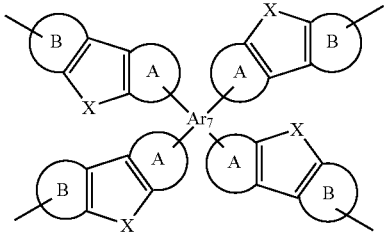

(8-4)

wherein the ring A, the ring B and X are as defined above; $Ar_3$, $Ar_4$, $Ar_5$ and $Ar_6$ each independently represent a trivalent aromatic ring or a trivalent metal complex structure; and $Ar_7$ represents a tetravalent aromatic ring or a tetravalent metal complex structure.

(x) The dendrimer compound according to any one of the above (i) to (ix), wherein the dendritic structure represented by the formula (3) is represented by the formula (7-1), (7-2) or (7-3).

(xi) The dendrimer compound according to any one of the above (i) to (ix), wherein the dendritic structure represented by the formula (4) is represented by the formula (7-1), (7-2), (7-3) or (7-4).

(xii) The dendrimer compound according to any one of the above (i) to (xi), wherein the ring A and the ring B are an aromatic hydrocarbon ring.

(xiii) The dendrimer compound according to any one of the above (i) to (xii), wherein at least one of the core and the dendritic structure contains a metal complex structure.

(xiv) The dendrimer compound according to any one of the above (i) to (xiii), further comprising a surface group in addition to the core and the dendritic structure.

(xv) A composition comprising at least one material selected from a hole transport material, an electron transport material and a luminescent material, and the dendrimer compound according to any one of the above (i) to (xiv).

(xvi) A composition characterized by comprising the dendrimer compound according to any one of the above (i) to (xiv) and a conjugated polymer compound containing an aromatic ring in the main chain.

(xvii) The composition according to the above (xvi), further comprising at least one material selected from a hole transport material, an electron transport material and a luminescent material.

(xviii) An ink composition characterized by comprising the dendrimer compound or the composition according to any one of the above (i) to (xvii).

(xix) The ink composition according to the above (xviii), having a viscosity of 1 to 100 mPa·s at 25° C.

(xx) A luminescent thin film characterized by comprising the dendrimer compound or the composition according to any one of the above (i) to (xvii).

(xxi) A conductive thin film characterized by comprising the dendrimer compound or the composition according to any one of the above (i) to (xvii).

(xxii) An organic semiconductor thin film characterized by comprising the dendrimer compound or the composition according to any one of the above (i) to (xvii).

(xxiii) An organic luminescent device characterized by comprising a layer containing the dendrimer compound or the composition according to any one of the above (i) to (xvii) between electrodes of an anode and a cathode.

(xxiv) The organic luminescent device according to the above (xxiii), wherein the layer containing the dendrimer compound or the composition according to any one of the above (i) to (xvii) is a luminescent layer.

(xxv) A planar light source characterized by comprising the organic luminescent device according to the above (xxiii) or (xxiv).

(xxvi) A segment display device characterized by comprising the organic luminescent device according to the above (xxiii) or (xxiv).

(xxvii) A dot matrix display device characterized by comprising the organic luminescent device according to the above (xxiii) or (xxiv).

(xxviii) A liquid crystal display device characterized by comprising the organic luminescent device according to the above (xxiii) or (xxiv) as a backlight.

(xxix) An illumination characterized by comprising the organic luminescent device according to the above (xxiii) or (xxiv).

Advantages of the Invention

The dendrimer compound of the present invention is a novel dendrimer compound useful as a luminescent material or a charge transport material.

BEST MODE FOR CARRYING OUT THE INVENTION

The dendrimer compound of the present invention comprises a core represented by the above formula (1-1), (1-2), (1-3) or (1-4) and at least one dendritic structure selected from dendritic structures represented by the above formula (3) or (4).

Dendrimer compounds are described in, for example, JP-A-11-140180, JP-A-2002-220468, "Dendritic Molecules" published by VCH Publishers, 1996, "Dendorima no Bunshisekkei (Molecular Design of Dendrimers)" and "Dendorima no Tasaina Kino (Dendrimers and Their Various Functions)", pp.20-40, Chemistry today, June 1998, and "Dendrima no Hisenkeikogakuzairyo heno Oyo (Dendrimers, Application to Nonlinear Optical Materials)" in Kobunshi Vol. 47, November (1998). In the present invention, the dendrimer compound refers to a dendritic compound having a chemical structure composed of a core (nucleus) and a dendritic structure containing a branched unit. The dendritic structure as used herein refers to a branched unit of DA or DB and three or four branched portions containing a linking group. The dendritic structure and repeated part thereof are called dendron.

To describe the size of dendrimers, a notion of generation is used. In the present invention, the core, which is the most central part, refers to the central structure including 1, 2, 3 or 4 branched portions containing a linking group. The first dendritic structure or branched unit next to the core including its terminal is defined as the first generation. When there is another dendritic structure outside the dendritic structure of the first generation, the succeeding dendritic structure or branched unit including its terminal is defined as the second generation. Likewise, for the third and the following generations, a subsequent dendritic structure or branched unit including its terminal is defined as the next generation.

In the dendrimer of the present invention, a preferred number of generations is in the range of 1 to 5, more preferably 1 to 3.

Examples of structures of dendrimer compounds include structures containing a dendron in which one kind of dendritic structure is regularly repeated, which are represented by the following formula (18-1), (18-2), (18-3) or (18-4).

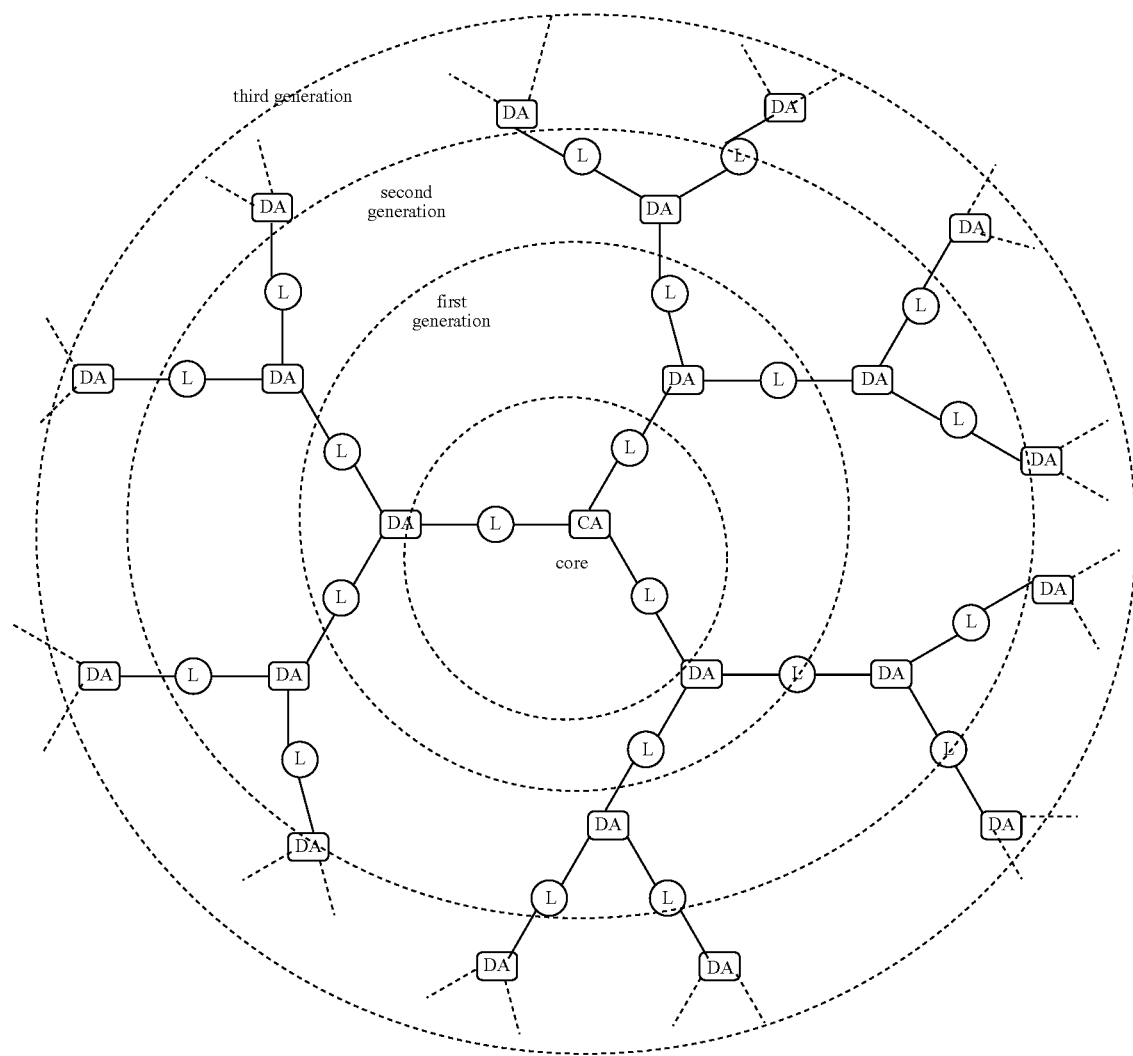

-continued
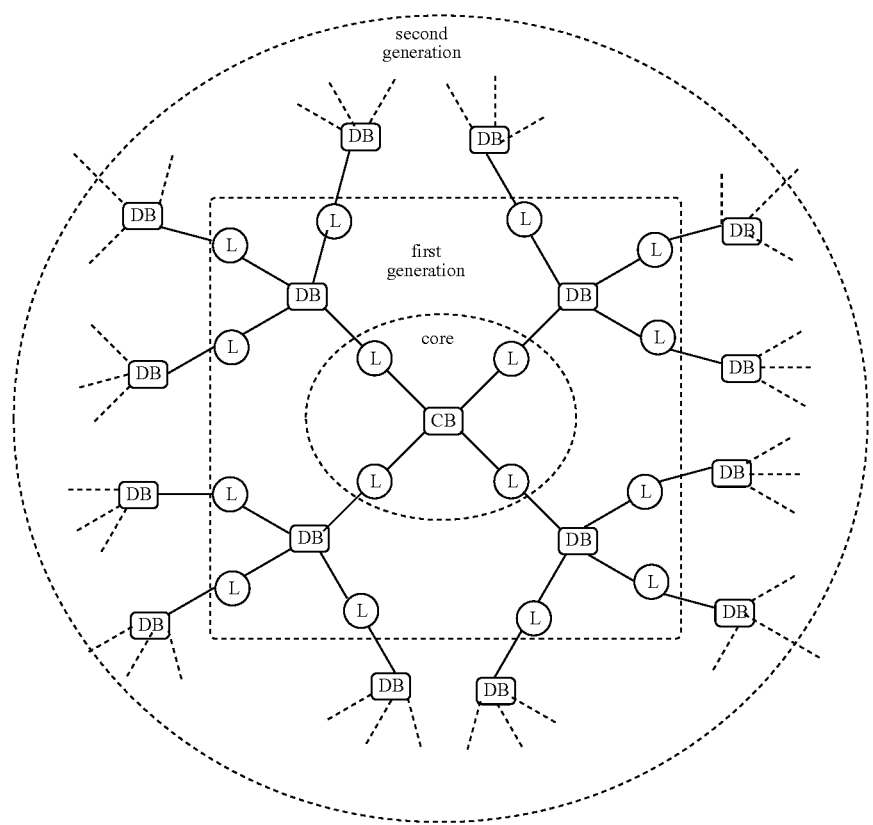
(18-2)

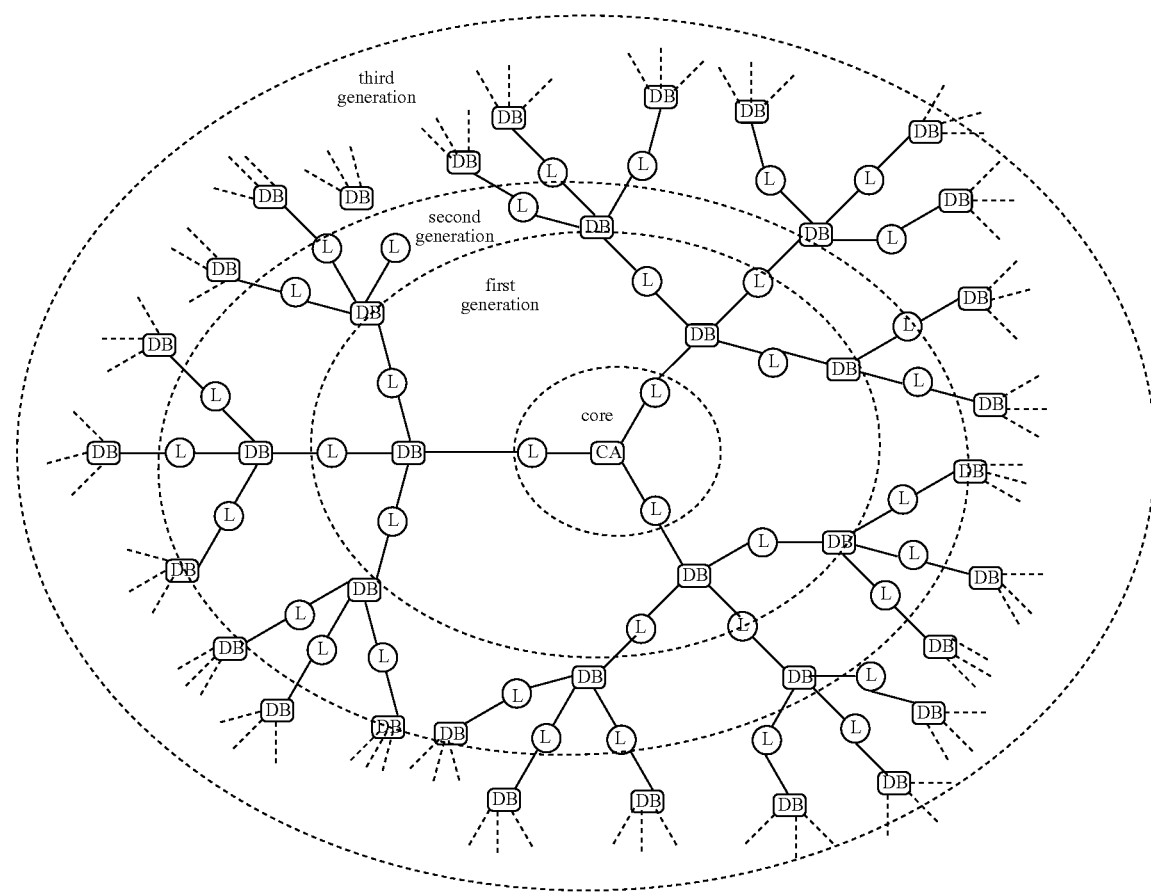
(18-3)

(18-4)

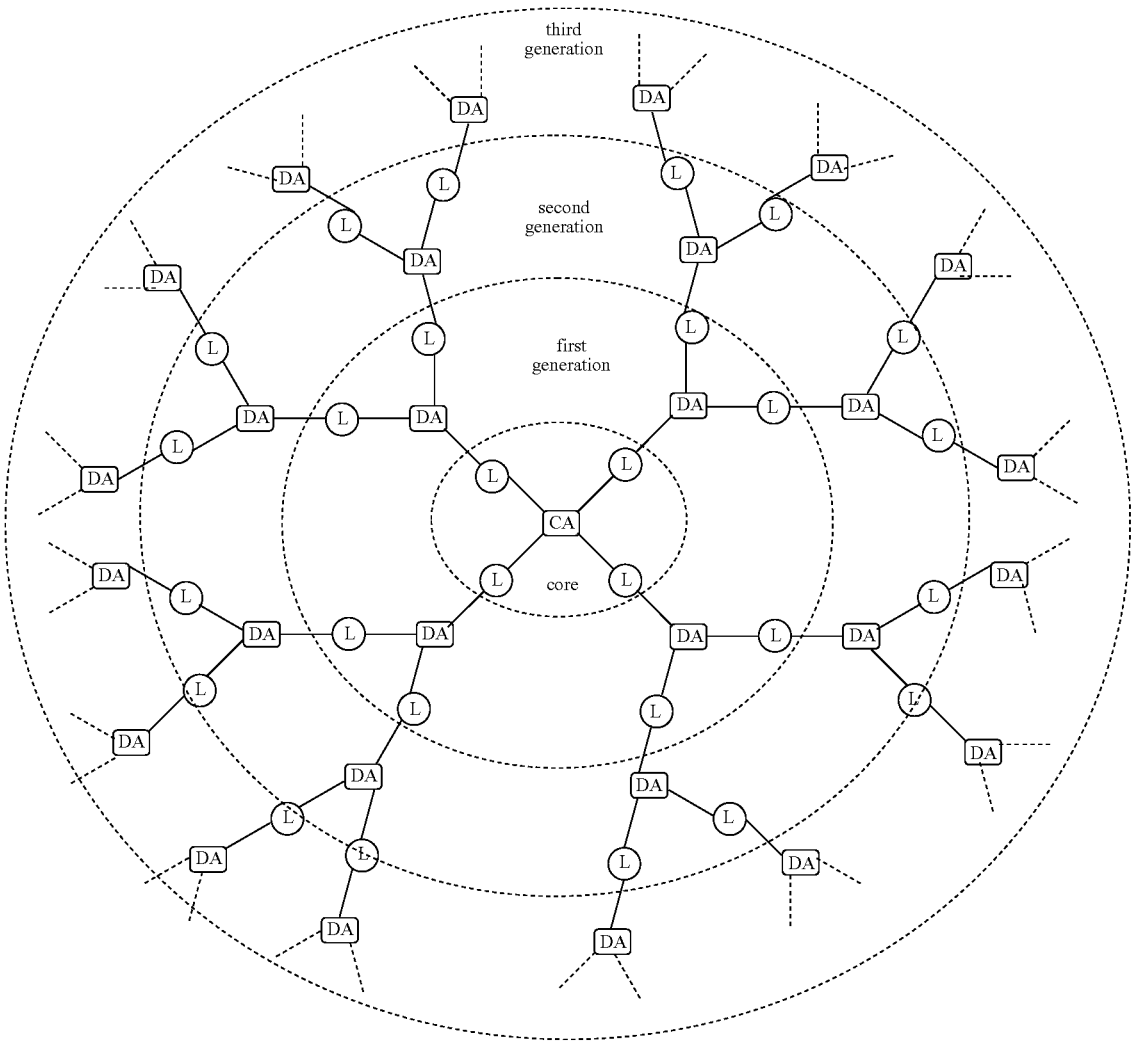

Examples of structures of the dendrimer compounds of the present invention also include structures which contain an identical dendritic structure within one dendron but contain two types of dendrons having a different number of branches in one generation represented by the following formula (18-5); structures which contain an identical dendritic structure within one dendron and contain two or more kinds of dendrons having the same number of branches but a different kind of branched unit in one generation represented by the following formula (18-6); structures which contain one kind of dendron whose dendritic structure is different in each generation represented by the following formula (18-7); and structures represented by the formula (18-8) in which the above are combined.

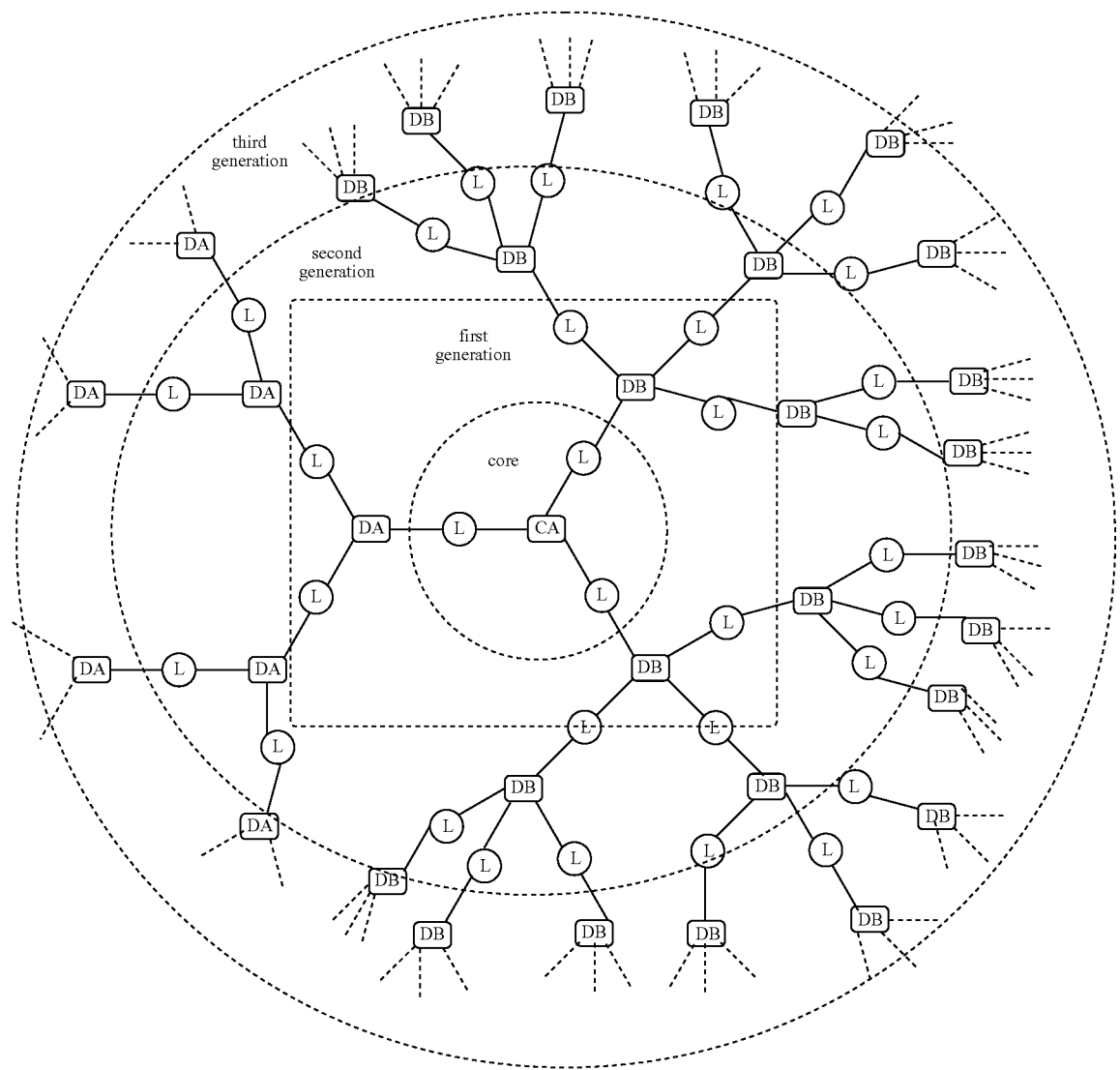

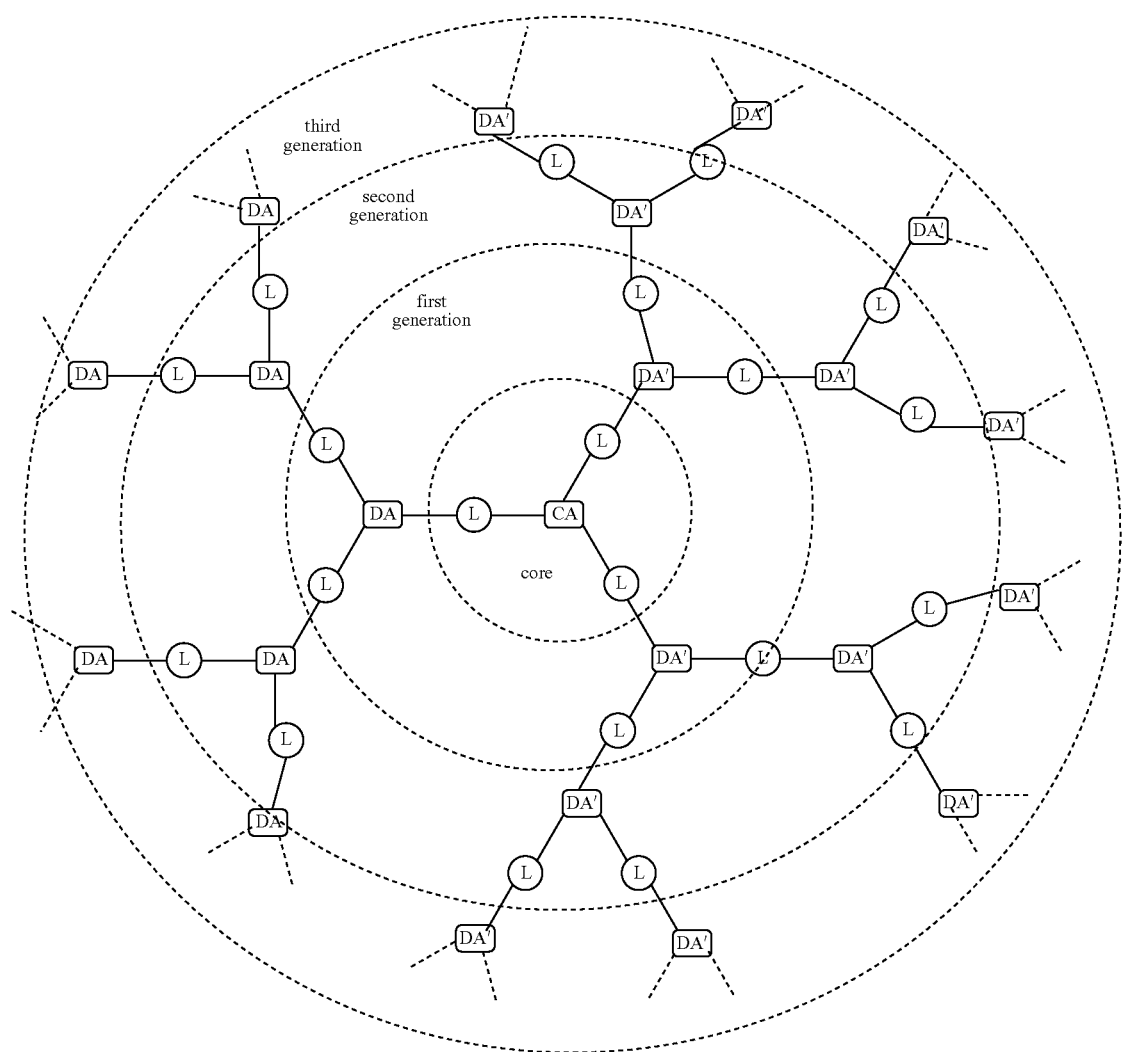
(18-6)

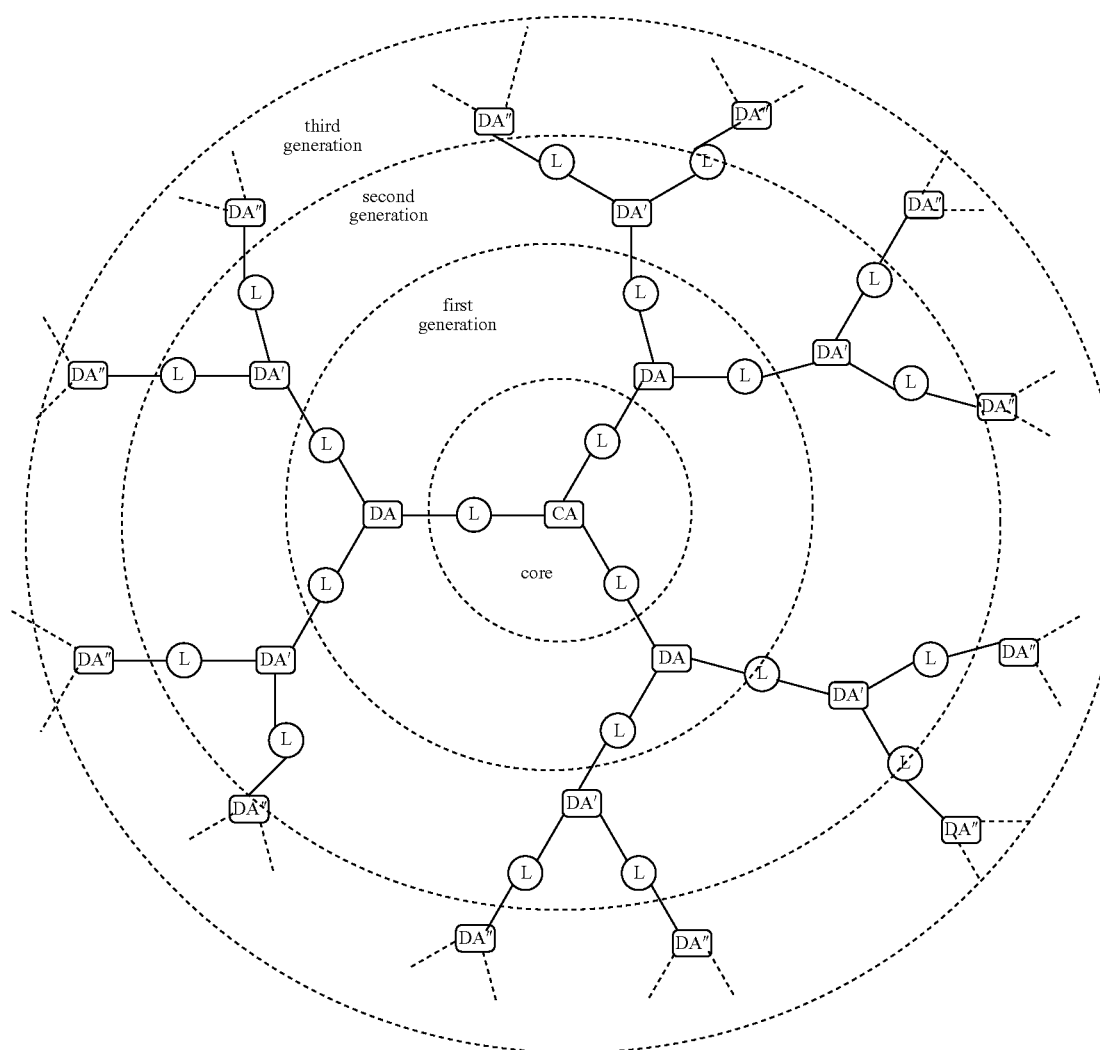
(18-7)

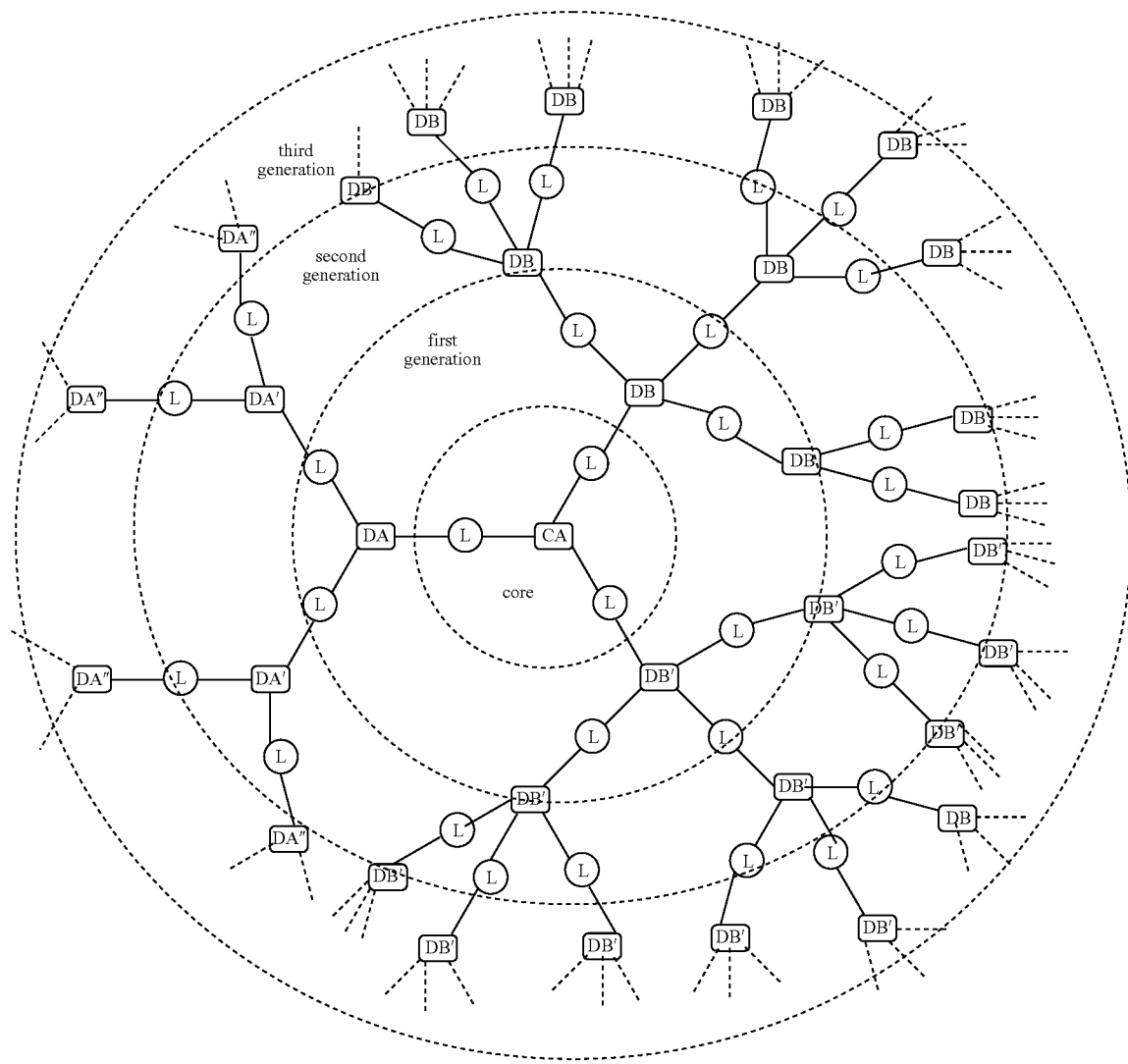
(18-8)
Examples of structures of dendrimer compounds also include structures represented by the following formula (18-9), (18-9-1), (18-9-2), (18-9-3) or (18-9-4) in which part of the dendrons has a regular repeat structure.

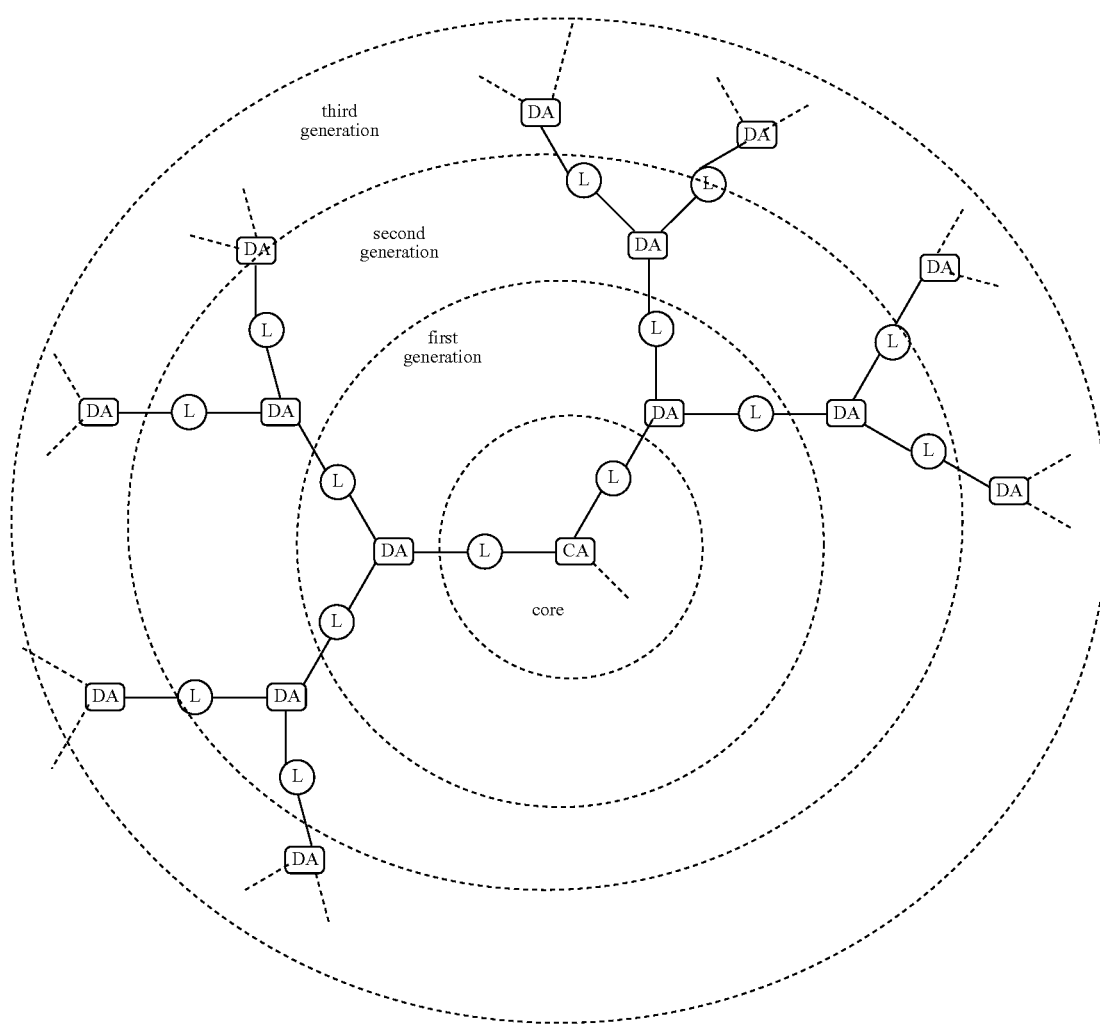

(18-9-1)
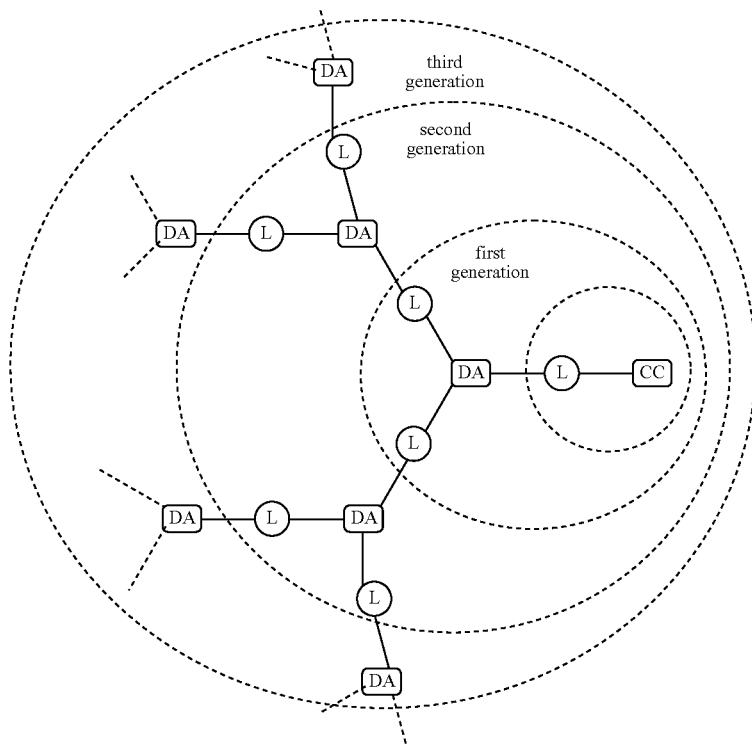
(18-9-2)
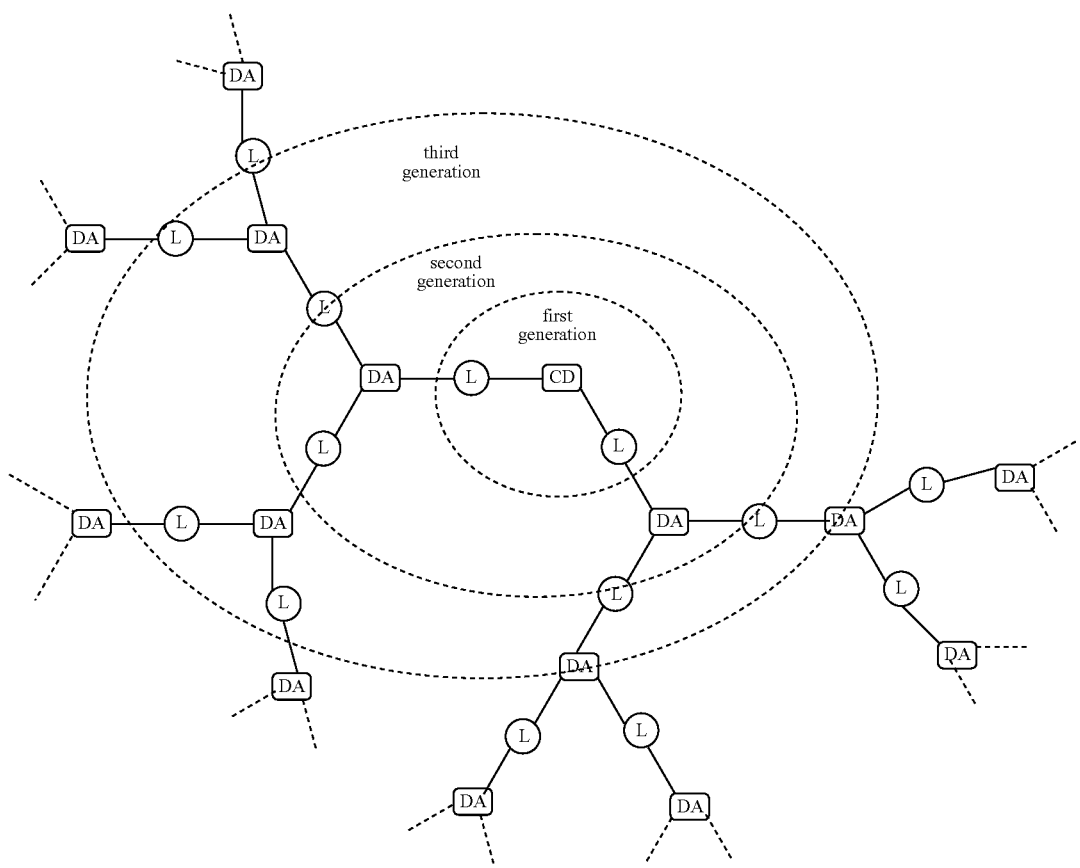

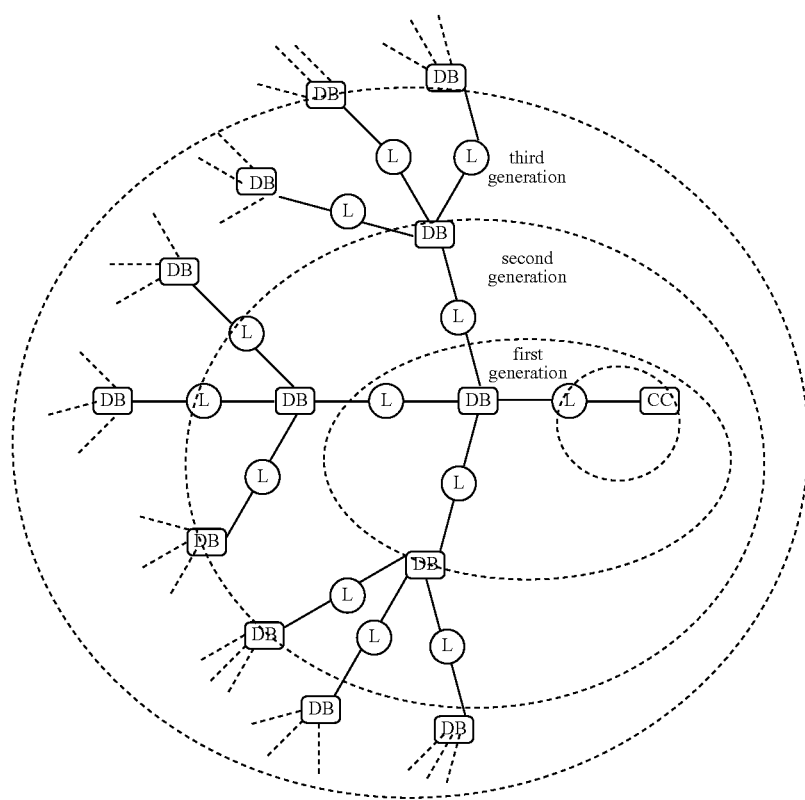
(18-9-3)

(18-9-4)

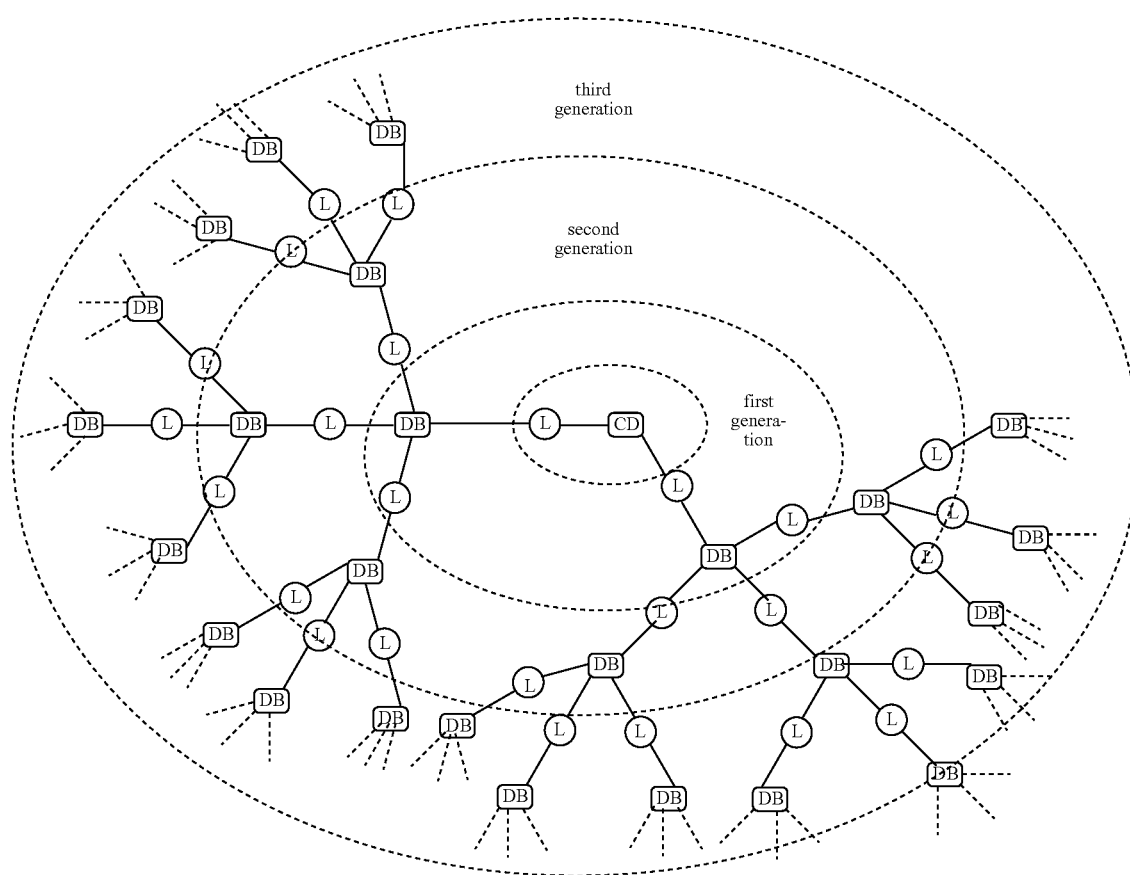

Examples of structures of dendrimer compounds also include those in which L in the formulas (18-1) to (18-9), (18-9-1), (18-9-2), (18-9-3) and (18-9-4) is different in each generation or dendron.

In view of ease in synthesis while it depends on the synthesis method, preferred structures of dendrimer compounds are structures containing a dendron in which one kind of dendritic structure is regularly repeated represented by the above formula (18-1), (18-2), (18-3) or (18-4); structures which contain an identical dendritic structure within one dendron but contain two types of dendrons having a different number of branches in one generation represented by the above formula (18-5); and structures which contain an identical dendritic structure within one dendron and contain two or more kinds of dendrons having the same number of branches but a different kind of branched unit in one generation represented by the above formula (18-6). Particularly preferred are structures containing a dendron in which one kind of dendritic structure is regularly repeated represented by the above formula (18-1), (18-2), (18-3) or (18-4).

Herein, the unit CA, the unit CB, the unit CC and the unit CD each independently represent an aromatic ring, a metal complex structure, a structure represented by the following formula (5), or a structure in which two or more structures selected from an aromatic ring, a metal complex structure and a structure represented by the following formula (5), which may be the same or different, are bonded directly or via a divalent group shown in the following (L-1). The following group in the formula (1-1):

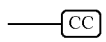

is a monovalent group. The following group in the formula (1-2):

is a divalent group. The following group in the formula (1-3):

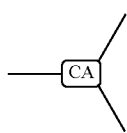

is a trivalent group. And the following group in the formula (1-4):

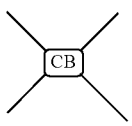

is a tetravalent group.

The unit DA and the unit DB each independently represent an aromatic ring, a metal complex structure, a structure represented by the following formula (5), or a structure in which two or more structures selected from an aromatic ring, a metal complex structure and a structure represented by the following formula (5), which may be the same or different, are bonded.

The following group in the formula (3):

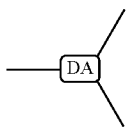

is a trivalent group, and the following group in the formula (4):

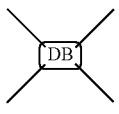

is a tetravalent group.

In the above formulas (18-6), (18-7) and (18-8), the unit DA' and the unit DA" have the same definition as the unit DA. The unit DA', the unit DA" and the unit DA represent a unit different from each other. The unit DB' has the same definition as the unit DB, and the unit DB' and the unit DB represent a ring different from each other.

Examples of aromatic rings include aromatic hydrocarbon rings such as a benzene ring, a naphthalene ring, an anthracene ring, a tetracene ring, a pentacene ring, a pyrene ring and a phenanthrene ring; and heteroaromatic rings such as a pyridine ring, a phenanthroline ring, a quinoline ring, an isoquinoline ring, a thiophene ring, a furan ring and a pyrrole ring.

The metal complex structure is a metal complex containing an organic ligand. Examples of organic ligands include 8-quinolinol and derivatives thereof, benzoquinolinol and derivatives thereof, 2-phenylpyridine and derivatives thereof, 2-phenylbenzothiazole and derivatives thereof, 2-phenylbenzoxazole and derivatives thereof, porphyrin and derivatives thereof, acetylacetone and derivatives thereof, phthalocyanine and derivatives thereof, salen and derivatives thereof, 1,10-phenanthroline and derivatives thereof and 2,6-di(2-pyridyl)-pyridine and derivatives thereof. Examples of central metal of the complex include aluminum, zinc, beryllium, ruthenium, rhodium, rhenium, iridium, platinum, gold, europium and terbium.

Examples of metal complexes include tris(8-quinolinol) aluminum and triplet luminescence complexes such as Ir(ppy)$_3$ and Btp$_2$Ir(acac) in which the central metal is iridium, PtOEP in which the central metal is platinum and Eu(TTA)$_3$phen in which the central metal is europium.

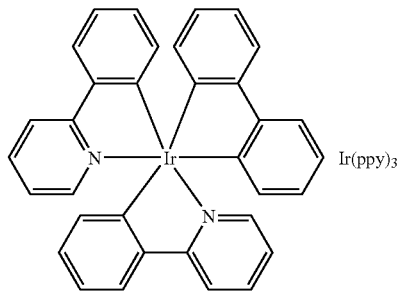

Ir(ppy)$_3$

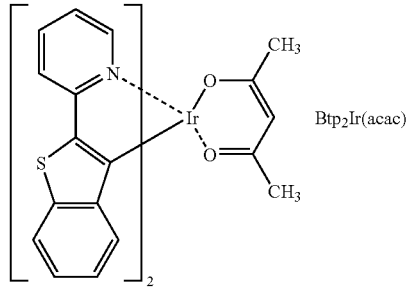

Btp$_2$Ir(acac)

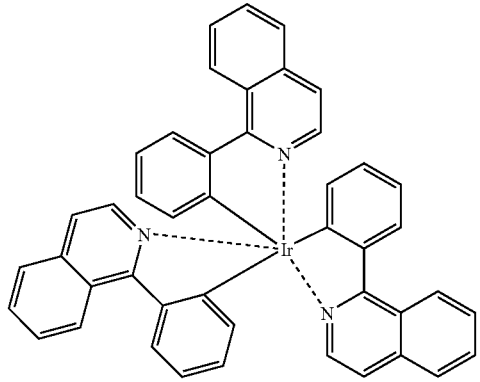

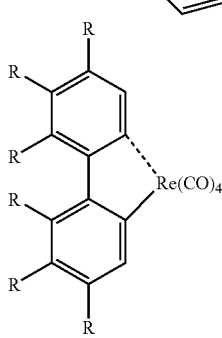

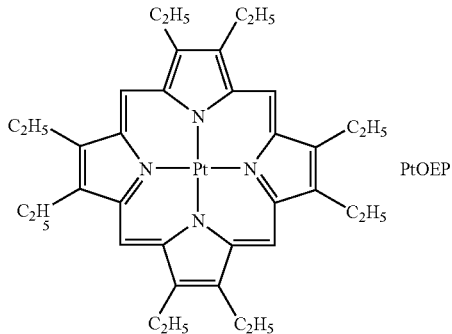

PtOEP

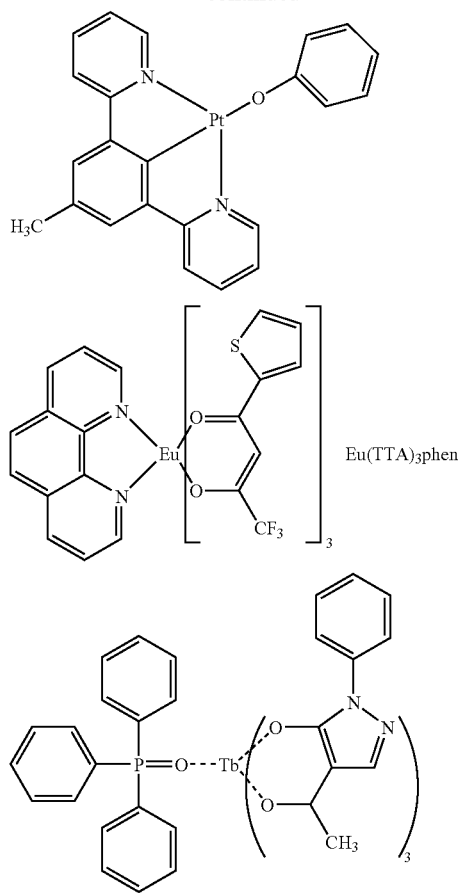
In the aforementioned formula (5), the ring A and the ring B each independently represent an aromatic ring. The aromatic ring is as defined above. The aromatic rings of the ring A and the ring B may be the same or different.
Specific examples of unsubstituted structures of the formula (5) are as follows.
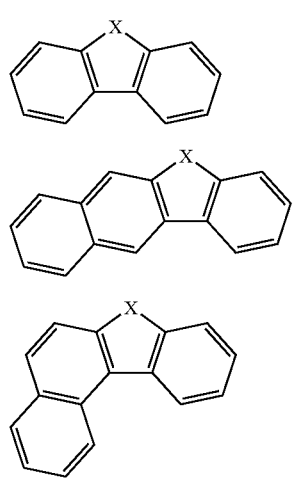
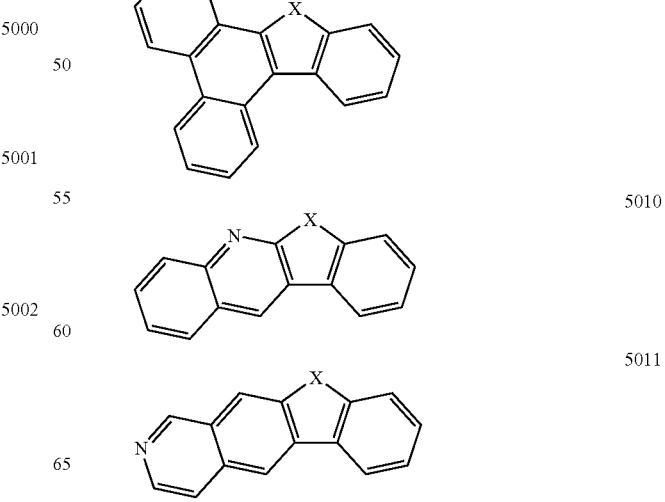

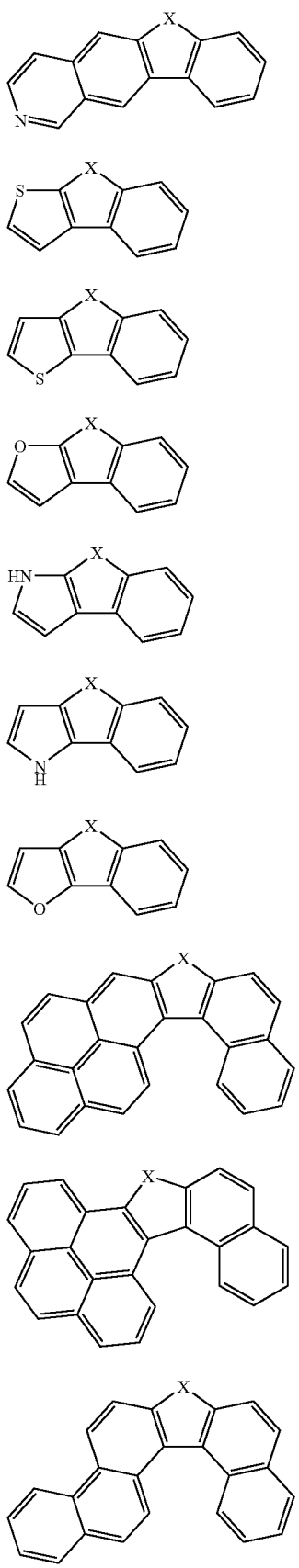
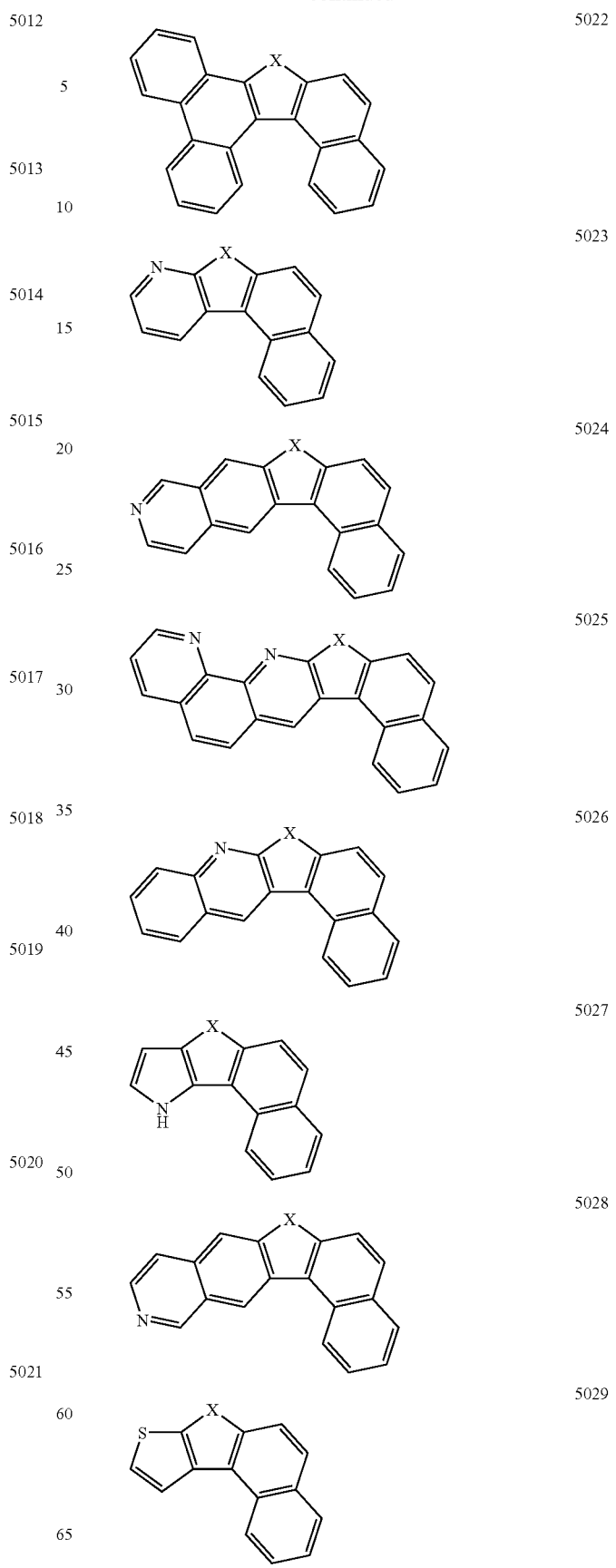

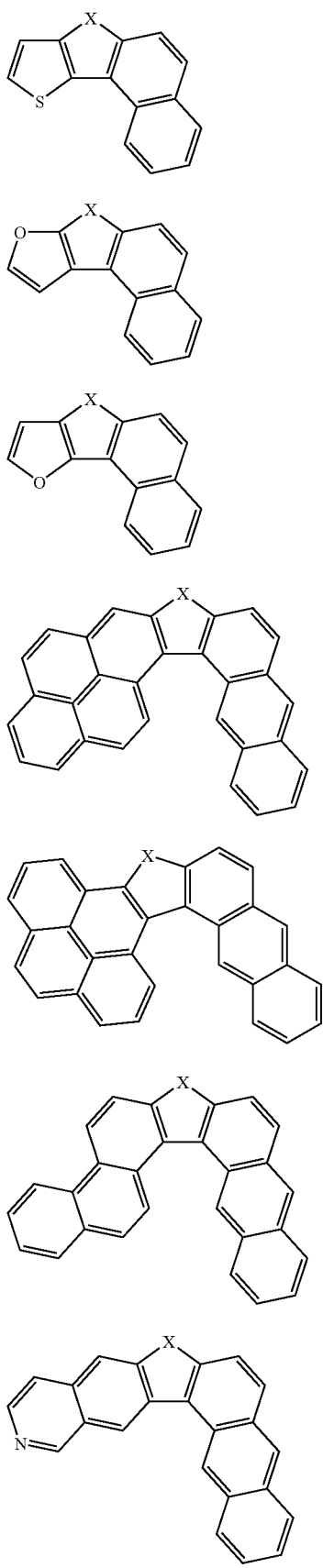
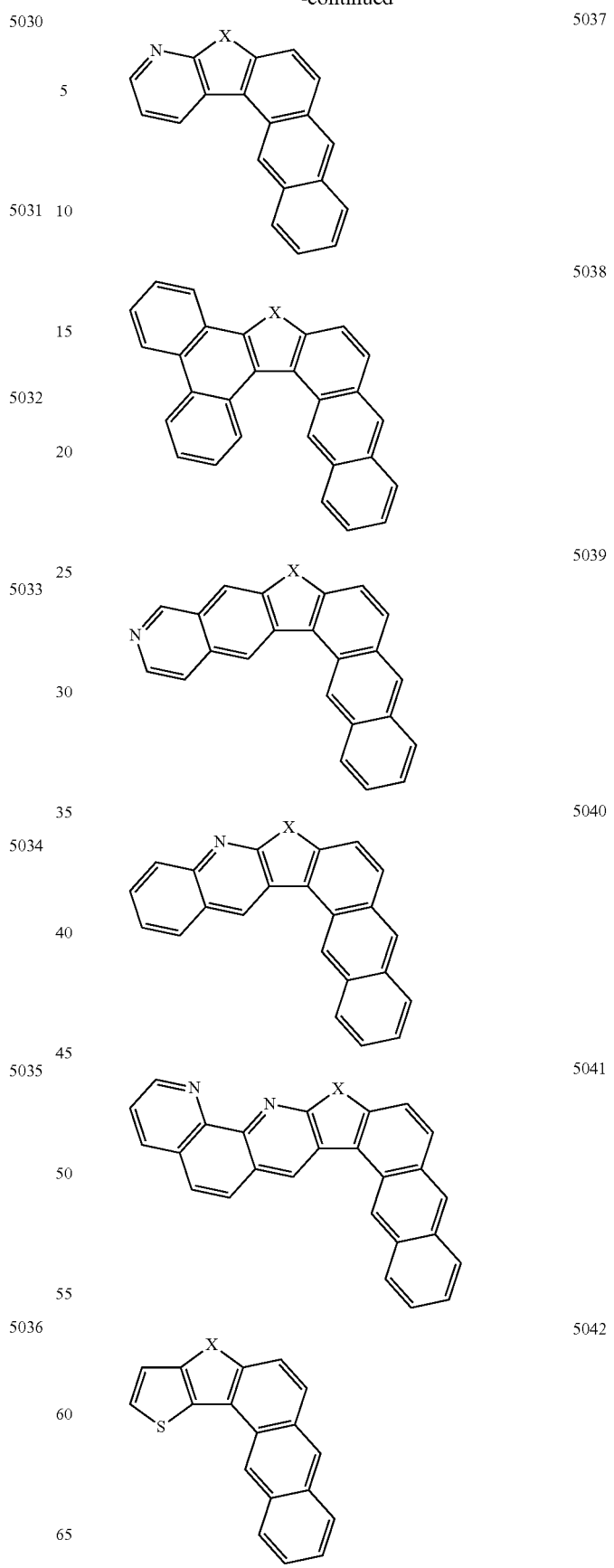

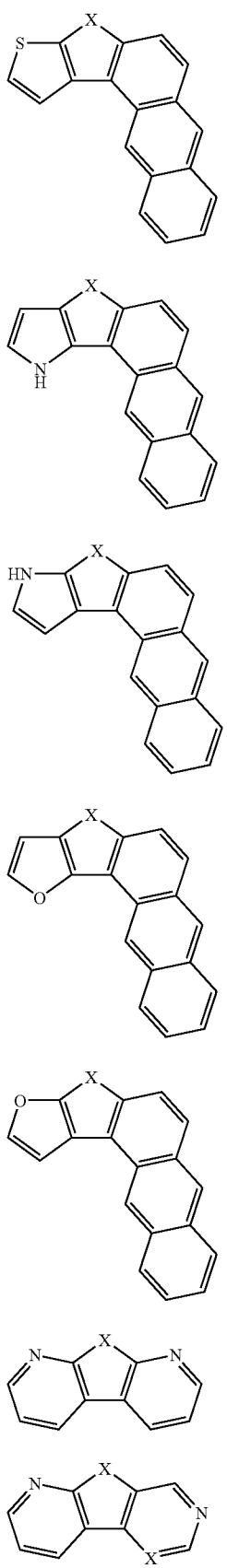
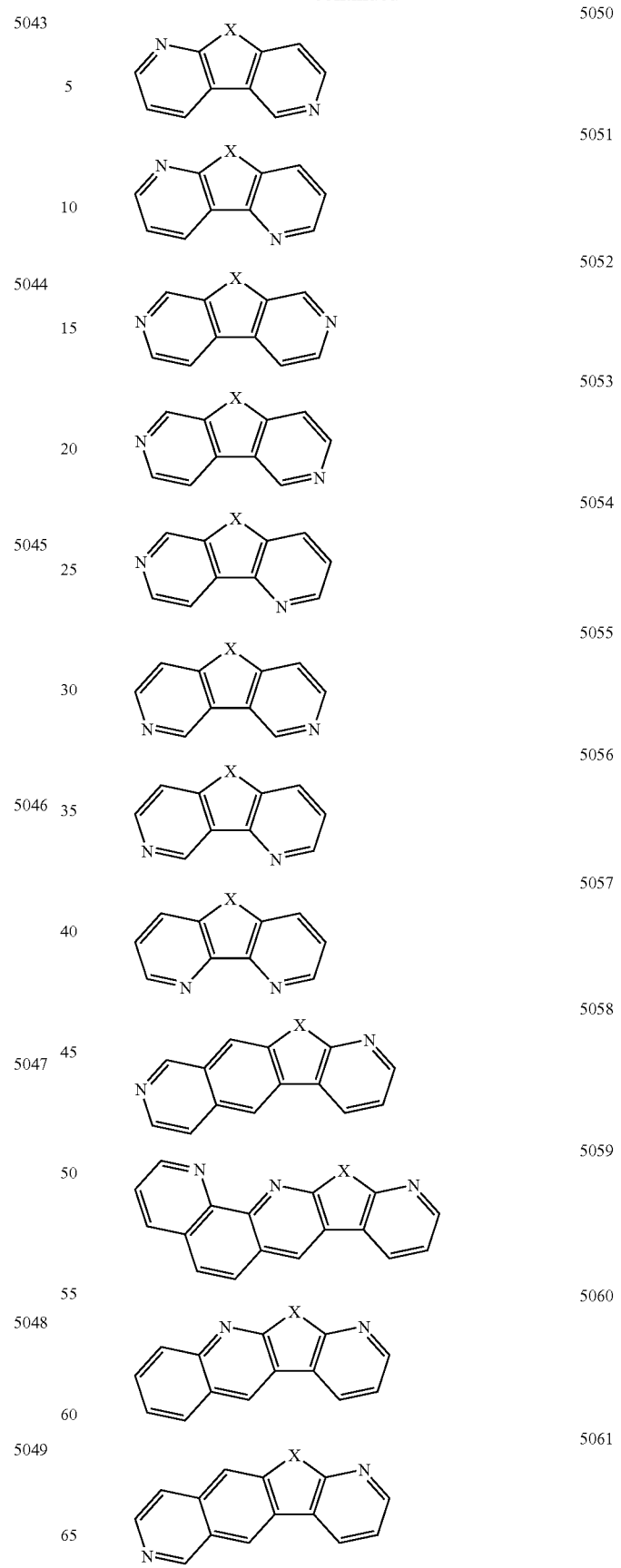

-continued

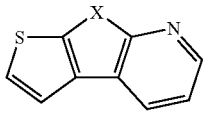
5062

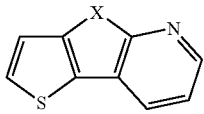
5063

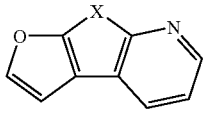
5064

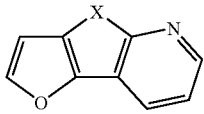
5065

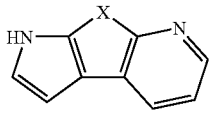
5066

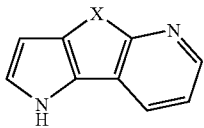
5067

X represents —O—, —S—, —S(=O)—, —SO$_2$—, —B(R$_1$)—, —Si(R$_2$)(R$_3$)—, —P(R$_4$)— or —PR$_5$(=O)—, and R$_1$, R$_2$, R$_3$, R$_4$ and R$_5$ each independently represent a substituent selected from an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group and a monovalent heterocyclic group.

The aromatic ring, the metal complex structure and the structure represented by the formula (5) described above may have a substituent Q. Examples of substituents Q include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a halogen atom, an acyl group, an acyloxy group, imine residue, an amide group, an acid imide group, a monovalent heterocyclic group, a carboxyl group, a substituted carboxyl group and a cyano group. Preferred are an alkyl group, an alkoxy group, an alkylthio group, an aryl group, an aryloxy group, an arylthio group, a substituted amino group, a substituted silyl group, a substituted silyloxy group and a monovalent heterocyclic group. An unsubstituted aromatic ring generally has 6 to 60 carbon atoms, preferably 6 to 20 carbon atoms.

Herein, the alkyl group may be linear, branched or cyclic. An alkyl group generally has 1 to 20 carbon atoms. Specific examples thereof include a methyl group, an ethyl group, a propyl group, an i-propyl group, a butyl group, an i-butyl group, a t-butyl group, a pentyl group, a hexyl group, a cyclohexyl group, a heptyl group, an octyl group, a 2-ethylhexyl group, a nonyl group, a decyl group, a 3,7-dimethyloctyl group, a lauryl group, a trifluoromethyl group, a pentafluoroethyl group, a perfluorobutyl group, a perfluorohexyl group and a perfluorooctyl group. Preferred are a pentyl group, a hexyl group, an octyl group, 2-ethyl hexyl group, a decyl group and a 3,7-dimethyloctyl group.

The alkoxy group may be linear, branched or cyclic. An alkoxy group generally has 1 to 20 carbon atoms. Specific examples thereof include a methoxy group, an ethoxy group, a propyloxy group, an i-propyloxy group, a butoxy group, an i-butoxy group, a t-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexyl group, a perfluorooctyl group, a methoxymethyloxy group, a 2-methoxyethyloxy group. Preferred are a pentyloxy group, a hexyloxy group, an octyloxy group, a 2-ethylhexyloxy group, a decyloxy group and a 3,7-dimethyloctyloxy group.

The alkylthio group may be linear, branched or cyclic. An alkylthio group generally has 1 to 20 carbon atoms. Specific examples thereof include a methylthio group, an ethylthio group, a propylthio group, an i-propylthio group, a butylthio group, an i-butylthio group, a t-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and a trifluoromethylthio group. Preferred are a pentylthio group, a hexylthio group, an octylthio group, a 2-ethylhexylthio group, a decylthio group and a 3,7-dimethyloctylthio group.

An aryl group generally has 6 to 60 carbon atoms. Specific examples thereof include a phenyl group, a $C_1$-$C_{12}$ alkoxyphenyl group ($C_1$-$C_{12}$ means having 1 to 12 carbon atoms; the same applies below), a $C_1$-$C_{12}$ alkylphenyl group, a 1-naphthyl group, a 2-naphthyl group, a 1-anthracenyl group, a 2-anthracenyl group, a 9-anthracenyl group and a pentafluorophenyl group. Preferred are a $C_1$-$C_{12}$ alkoxyphenyl group and a $C_1$-$C_{12}$ alkylphenyl group. Herein, the aryl group refers to an atomic group in which a hydrogen atom is missing from aromatic hydrocarbon. Aromatic hydrocarbons include those containing a benzene ring or a fused ring and those in which two or more independent benzene rings or fused rings are bonded directly or via a group such as vinylene.

Specific examples of $C_1$-$C_{12}$ alkoxy include methoxy, ethoxy, propyloxy, i-propyloxy, butoxy, i-butoxy, t-butoxy, pentyloxy, hexyloxy, cyclohexyloxy, heptyloxy, octyloxy, 2-ethylhexyloxy, nonyloxy, decyloxy, 3,7-dimethyloctyloxy and lauryloxy.

Specific examples of $C_1$-$C_{12}$ alkyl include methyl, ethyl, propyl, i-propyl, butyl, i-butyl, t-butyl, pentyl, hexyl, cyclohexyl, heptyl, octyl, 2-ethylhexyl, nonyl, decyl, 3,7-dimethyloctyl and lauryl.

An aryloxy group generally has 6 to 60 carbon atoms. Specific examples thereof include a phenoxy group, a $C_1$-$C_{12}$ alkoxyphenoxy group, a $C_1$-$C_{12}$ alkylphenoxy group, a 1-naphthyloxy group, a 2-naphthyloxy group and a pentafluorophenyloxy group. Preferred are a $C_1$-$C_{12}$ alkoxyphenoxy group and a $C_1$-$C_{12}$ alkylphenoxy group.

The arylthio group usually has about 6 to 60 carbon atoms. Specific examples include a phenylthio group, $C_1$-$C_{12}$ alkoxyphenylthio group, $C_1$-$C_{12}$ alkylphenylthio group, 1-naphthylthio group, 2-naphthylthio group, pentafluorophenylthio group and the like, wherein the $C_1$-$C_{12}$ alkoxyphenylthio group and $C_1$-$C_{12}$ alkylphenylthio group are preferable.

The arylalkyl group usually has about 7 to 60 carbon atoms. Specific examples include phenyl-$C_1$-$C_{12}$ alkyl groups, such as a phenylmethyl group, phenylethyl group, phenylbutyl group, phenylpentyl group, phenylhexyl group, phenylheptyl group, and phenyloctyl group; $C_1$-$C_{12}$ alkoxyphenyl-$C_1$-$C_{12}$ alkyl group, $C_1$-$C_{12}$ alkylphenyl-$C_1$-$C_{12}$ alkyl group, 1-naphthyl-$C_1$-$C_{12}$ alkyl group, 2-naphthyl-$C_1$-$C_{12}$ alkyl group and the like, wherein the $C_1$-$C_{12}$ alkoxyphenyl-$C_1$-$C_{12}$ alkyl group, and $C_1$-$C_{12}$ alkylphenyl-$C_1$-$C_{12}$ alkyl group are preferable.

The arylalkoxy group usually has about 7 to 60 carbon atoms. Specific examples include phenyl-$C_1$-$C_{12}$ alkoxy groups, such as a phenylmethoxy group, phenylethoxy group, phenylbutoxy group, phenylpentyloxy group, phenylhexyloxy group, phenylheptyloxy group, and phenyloctyloxy group; $C_1$-$C_{12}$ alkoxyphenyl-$C_1$-$C_{12}$ alkoxy group, $C_1$-$C_{12}$ alkylphenyl-$C_1$-$C_{12}$ alkoxy group, 1-naphthyl-$C_1$-$C_{12}$ alkoxy group, 2-naphthyl-$C_1$-$C_{12}$ alkoxy group and the like, wherein the $C_1$-$C_{12}$ alkoxyphenyl-$C_1$-$C_{12}$ alkoxy group and $C_1$-$C_{12}$ alkylphenyl-$C_1$-$C_{12}$ alkoxy group are preferable.

The arylalkylthio group usually has about 7 to 60 carbon atoms. Specific examples include a phenyl-$C_1$-$C_{12}$ alkylthio group, $C_1$-$C_{12}$ alkoxyphenyl-$C_1$-$C_{12}$ alkylthio group, $C_1$-$C_{12}$ alkylphenyl-$C_1$-$C_{12}$ alkylthio group, 1-naphthyl-$C_1$-$C_{12}$ alkylthio group, 2-naphthyl-$C_1$-$C_{12}$ alkylthio group and the like, wherein the $C_1$-$C_{12}$ alkoxyphenyl-$C_1$-$C_{12}$ alkylthio group and $C_1$-$C_{12}$ alkylphenyl-$C_1$-$C_{12}$ alkylthio group are preferable.

The arylalkenyl group usually has about 8 to 60 carbon atoms. Specific examples include a phenyl-$C_2$-$C_{12}$ alkenyl group, $C_1$-$C_{12}$ alkoxyphenyl-$C_2$-$C_{12}$ alkenyl group, $C_1$-$C_{12}$ alkylphenyl-$C_2$-$C_{12}$ alkenyl group, 1-naphthyl-$C_2$-$C_{12}$ alkenyl group, 2-naphthyl-$C_2$-$C_{12}$ alkenyl group and the like, wherein the $C_1$-$C_{12}$ alkoxyphenyl-$C_2$-$C_{12}$ alkenyl group and $C_1$-$C_{12}$ alkylphenyl-$C_2$-$C_{12}$ alkenyl group are preferable.

The arylalkynyl group usually has about 8 to 60 carbon atoms. Specific examples include a phenyl-$C_2$-$C_{12}$ alkynyl group, $C_1$-$C_{12}$ alkoxyphenyl-$C_2$-$C_{12}$ alkynyl group, $C_1$-$C_{12}$ alkylphenyl-$C_2$-$C_{12}$ alkynyl group, 1-naphthyl-C2-$C_{12}$ alkynyl group, 2-naphthyl-$C_2$-$C_{12}$ alkynyl group and the like, wherein the $C_1$-$C_{12}$ alkoxyphenyl-$C_2$-$C_{12}$ alkynyl group and $C_1$-$C_{12}$ alkylphenyl-$C_2$-$C_{12}$ alkynyl group are preferable.

Examples of the substituted amino group include amino groups having one or two substituents selected from an alkyl group, aryl group, arylalkyl group, or a monovalent heterocyclic group. The substituted amino group usually has about 1 to 60 carbon atoms. Specific examples include a methylamino group, dimethylamino group, ethylamino group, diethylamino group, propylamino group, dipropylamino group, i-propylamino group, diisopropylamino group, butylamino group, i-butylamino group, t-butylamino group, pentylamino group, hexylamino group, cyclohexylamino group, heptylamino group, octylamino group, 2-ethylhexylamino group, nonylamino group, decylamino group, 3,7-dimethyloctylamino group, laurylamino group, cyclopentylamino group, dicyclopentylamino group, cyclohexylamino group, dicyclohexylamino group, pyrrolidyl group, piperidyl group, ditrifluoromethylamino group, phenyl amino group, diphenylamino group, $C_1$-$C_{12}$ alkoxyphenylamino group, di($C_1$-$C_{12}$ alkoxyphenyl) amino group, di($C_1$-$C_{12}$ alkylphenyl) amino group, 1-naphthylamino group, 2-naphthylamino group, pentafluorophenylamino group, pyridylamino group, pyridazinylamino group, pyrimidylamino group, pyrazylamino group, triazylamino group phenyl-$C_1$-$C_{12}$ alkylamino group, $C_1$-$C_{12}$ alkoxyphenyl-$C_1$-$C_{12}$ alkylamino group, $C_1$-$C_{12}$ alkyl phenyl-$C_1$-$C_{12}$ alkylamino group, di($C_1$-$C_{12}$ alkoxyphenyl-$C_1$-$C_{12}$ alkyl) amino group, di($C_1$-$C_{12}$ alkylphenyl-$C_1$-$C_{12}$ alkyl)amino group, 1-naphthyl-$C_1$-$C_{12}$ alkylamino group, 2-naphthyl-$C_1$-$C_{12}$ alkylamino group, carbazolyl group, and the like.

Examples of the substituted silyl group include silyl groups having 1, 2 or 3 substituents selected from an alkyl group, aryl group, arylalkyl group, and monovalent heterocyclic group. The substituted silyl group usually has about 1 to 60 carbon atoms.

Specific examples include a trimethylsilyl group, triethylsilyl group, tripropylsilyl group, tri-i-propylsilyl group, dimethyl-i-propylsilyl group, diethyl-i-propylsilyl group, t-butyldimethylsilyl group, pentyldimethylsilyl group, hexyldimethylsilyl group, heptyldimethylsilyl group, octyldimethylsilyl group, 2-ethylhexyl-dimethylsilyl group, nonyldimethylsilyl group, decyldimethylsilyl group, 3,7-dimethyloctyl-dimethylsilyl group, lauryldimethylsilyl group, phenyl-$C_1$-$C_{12}$ alkylsilyl group, $C_1$-$C_{12}$ alkoxyphenyl-$C_1$-$C_{12}$ alkylsilyl group, $C_1$-$C_{12}$ alkylphenyl-$C_1$-$C_{12}$ alkylsilyl group, 1-naphthyl-$C_1$-$C_{12}$ alkylsilyl group, 2-naphthyl-$C_1$-$C_{12}$ alkylsilyl group, phenyl-$C_1$-$C_{12}$ alkyldimethylsilyl group, triphenylsilyl group, tri-p-xylylsilyl group, tribenzylsilyl group, diphenylmethylsilyl group, t-butyldiphenylsilyl group, dimethylphenylsilyl group, trimethoxysilyl group, triethoxysilyl group, tripropyloxysilyl group, tri-i-propylsilyl group, dimethyl-i-propylsilyl group, methyldimethoxysilyl group, ethyldimethoxysilyl group and the like.

Examples of the substituted silyloxy group include silyloxy groups having 1, 2 or 3 substituents selected from an alkyl group, aryl group, arylalkyl group, and monovalent heterocyclic group. The substituted silyloxy group usually has about 1 to 60 carbon atoms.

Specific examples include a trimethylsilyloxy group, triethylsilyloxy group, tripropylsilyloxy group, tri-i-propylsilyloxy group, dimethyl-i-propylsilyloxy group, diethyl-i-propylsilyloxy group, t-butyldimethylsilyloxy group, pentyldimethylsilyloxy group, hexyldimethylsilyloxy group, heptyldimethylsilyloxy group, octyldimethylsilyloxy group, 2-ethylhexyl-dimethylsilyloxy group, nonyldimethylsilyloxy group, decyldimethylsilyloxy group, 3,7-dimethyloctyl-dimethylsilyloxy group, lauryldimethylsilyloxy group, phenyl-$C_1$-$C_{12}$ alkylsilyloxy group, $C_1$-$C_{12}$ alkoxyphenyl-$C_1$-$C_{12}$alkylsilyloxy group, $C_1$-$C_{12}$ alkylphenyl-$C_1$-$C_{12}$ alkylsilyloxy group, 1-naphthyl-$C_1$-$C_{12}$ alkylsilyloxy group, 2-naphthyl-$C_1$-$C_{12}$ alkylsilyloxy group, phenyl-$C_1$-$C_{12}$ alkyl dimethylsilyloxy group, triphenylsilyloxy group, tri-p-xylylsilyloxy group, tribenzylsilyloxy group, diphenylmethylsilyloxy group, t-butyldiphenylsilyloxy group, dimethylphenylsilyloxy group, trimethoxysilyloxy group, triethoxysilyloxy group, tripropyloxysilyloxy group, tri-i-propylsilyloxy group, dimethyl-i-propylsilyloxy group, methyldimethoxysilyloxy group, ethyldimethoxysilyloxy group, and the like.

Examples of the halogen atom include a fluorine atom, chlorine atom, bromine atom and iodine atom.

The acyl group usually has about 2 to 20 carbon atoms. Specific examples include an acetyl group, propionyl group, butyryl group, isobutyryl group, pivaloyl group, benzoyl group, trifluoroacetyl group, pentafluorobenzoyl group and the like.

The acyloxy group usually has about 2 to 20 carbon atoms Specific examples include an acetoxy group, propionyloxy group, butyryloxy group, isobutyryloxy group, pivaloyloky group, benzoyloxy group, trifluoro acetyloxy group, pentafluorobenzoyloxy group and the like.

Examples of the imine residue include residues in which one hydrogen atom is removed from an imine compound (referring to an organic compound having —N═C— in the molecule; examples include aldimine, ketamine and compounds thereof whose hydrogen atom on the nitrogen is substituted with an alkyl group or the like). The imine reside group has about 2 to 20 carbon atoms. Specific examples include the following groups.

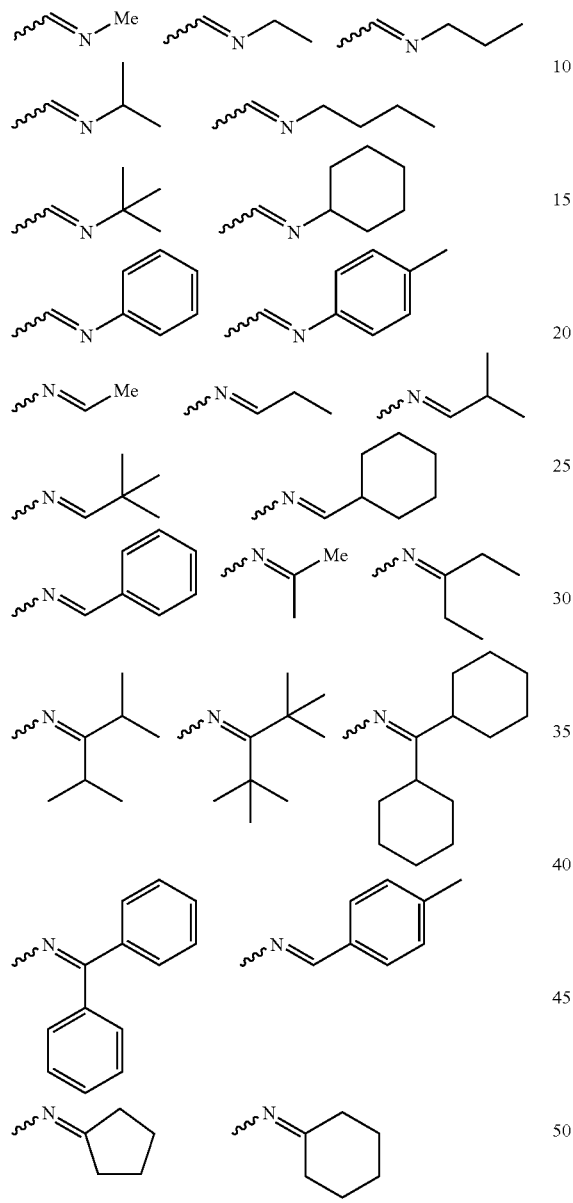

The amide group usually has about 1 to 20 carbon atoms. Specific examples include a formamide group, acetamide group, propioamide group, butyroamide group, benzamide group, trifluoroacetamide group, pentafluorobenzamide group, diformamide group, diacetamide group, dipropioamide group, dibutyroamide group, dibenzamide group, ditrifluoro acetamide group, dipentafluorobenzamide group and the like.

The acid imide group can be a residue obtained by removing a hydrogen atom bound to the nitrogen atom of the acid imide, and have about 4 to 20 carbon atoms. Specific examples include the following groups.

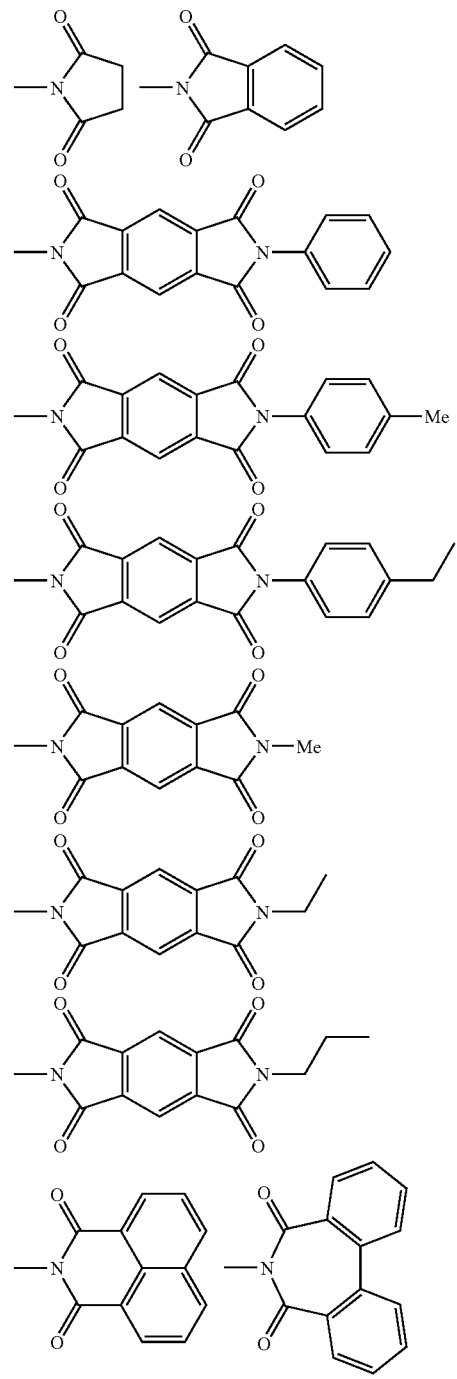

In the above examples, Me represents a methyl group.

The monovalent heterocyclic group is an atomic group in which a hydrogen atom is removed from a heterocyclic compound, which may have a substituent.

An unsubstituted monovalent heterocyclic group usually has about 4 to 60 carbon atoms, and preferably 4 to 20.

Examples of the monovalent heterocyclic group include a thienyl group, $C_1$-$C_{12}$ alkylthienyl group, pyroryl group, furyl group, pyridyl group, $C_1$-$C_{12}$ alkylpyridyl group and the like, wherein the thienyl group, $C_1$-$C_{12}$ alkylthienyl group, pyridyl group, and $C_1$-$C_{12}$ alkylpyridyl group are preferable.

The substituted carboxyl group usually has about 2 to 60 carbon atoms, and refers to a carboxyl group substituted with an alkyl group, aryl group, arylalkyl group, or monovalent heterocyclic group. Examples thereof include a methoxycarbonyl group, ethoxycarbonyl group, propoxycarbonyl group, i-propoxycarbonyl group, butoxycarbonyl group, i-butoxycarbonyl group, t-butoxycarbonyl group, pentyloxycarbonyl group, hexyloxycarbonyl group, cyclohexyloxycarbonyl group, heptyloxycarbonyl group, octyloxycarbonyl group, 2-ethylhexyloxycarbonyl group, nonyloxycarbonyl group, decyloxycarbonyl group, 3,7-dimethyloctyloxycarbonyl group, dodecyloxycarbonyl group, trifluoromethoxycarbonyl group, pentafluoroethoxycarbonyl group, perfluorobutoxycarbonyl group, perfluorohexyloxycarbonyl group, perfluorooctyloxycarbonyl group, phenoxycarbonyl group, naphthoxycarbonyl group, pyridyloxycarbonyl group and the like.

While the below example possesses a plurality of Rs contained in the one structural formula, these Rs may be the same or different. Here R is a hydrogen atom, or, as mentioned above, is defined in the same manner as the substituent Q which can have an aromatic ring, a metal complex structure, and the structure represented by the above formula (5). To improve solubility into a solvent, it is preferable that at least one of the Rs in one structural formula is other than a hydrogen atom. In the present invention, Rs other than a hydrogen atom are referred to as a "surface group". In addition, it is preferable that the form of the repeating unit including the substituent has little symmetry. Moreover, it is preferable that at least one of the Rs in one structural formula contains a cyclic or branched alkyl group. A plurality of Rs may be connected to form a ring.

In the above formula, when R is a substituent containing an alkyl group, the alkyl group may be linear, branched or cyclic, or may be a combination thereof. Examples of non-linear alkyl chains include an isoamyl group, 2-ethylhexyl group, 3,7-dimethyloctyl group, cyclohexyl group, 4-$C_1$-$C_{12}$ alkylcyclohexyl group and the like.

Furthermore, the alkyl group methyl group or methylene group of the alkyl-group-containing-group may be replaced by a group containing a hetero atom, or a methyl or methylene group which is substituted with one or more fluorine atoms. Examples of the hetero atom include an oxygen atom, sulfur atom, nitrogen atom and the like.

For the of the following group in formula (1-1),

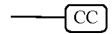

specific examples include the below monovalent aromatic hydrocarbon cyclic groups.

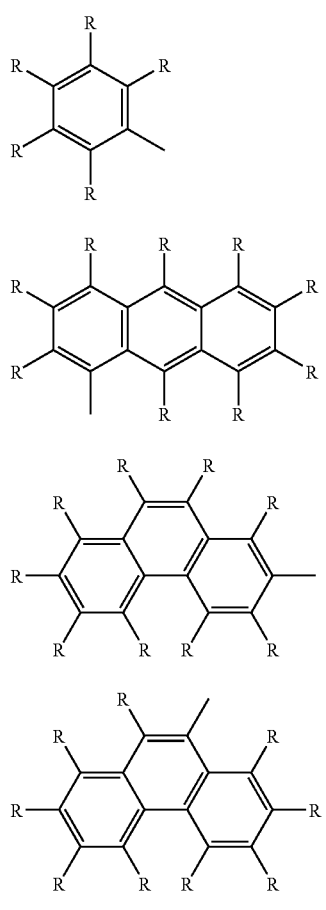

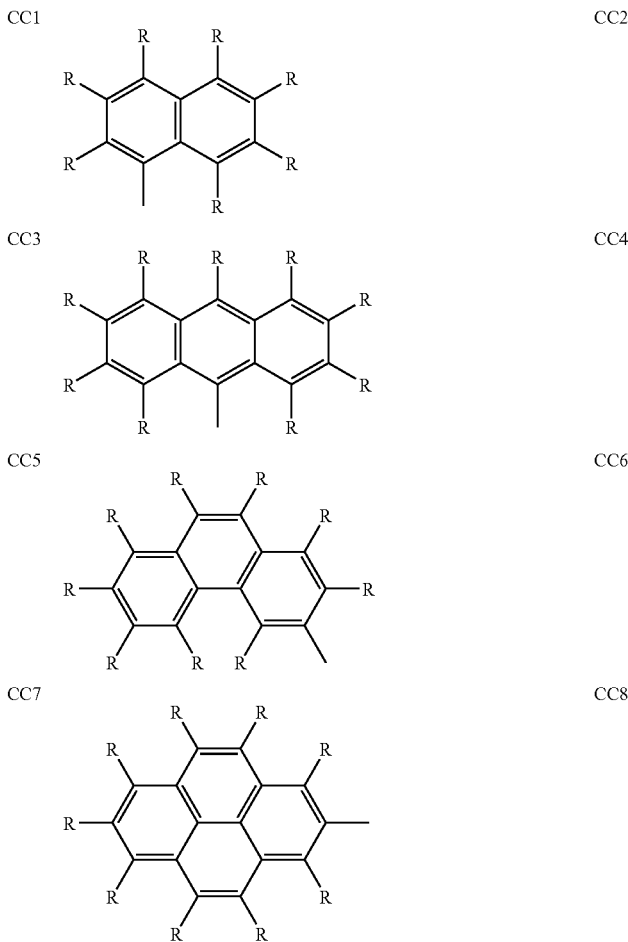

-continued
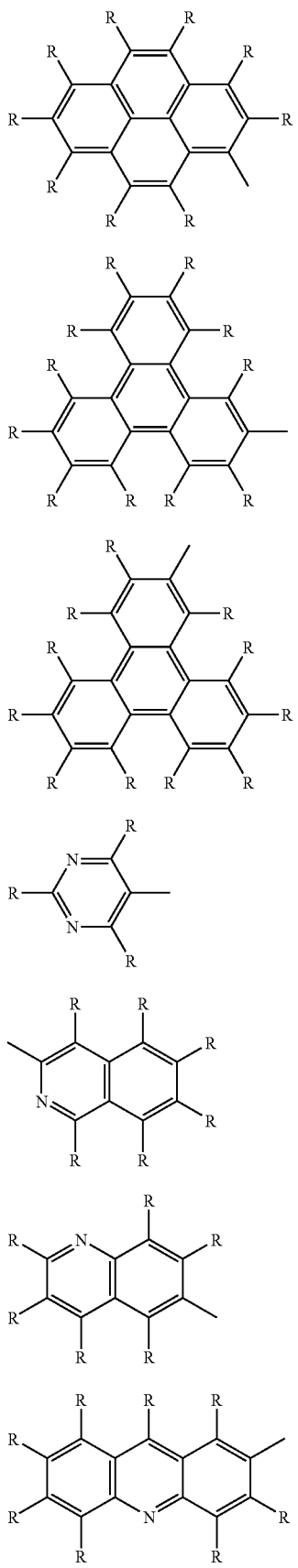
CC9
CC11
CC13
CC15
CC17
CC19
CC21
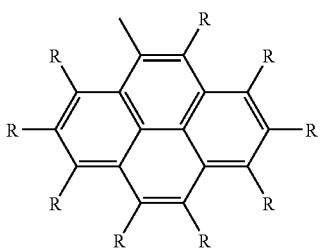
CC10
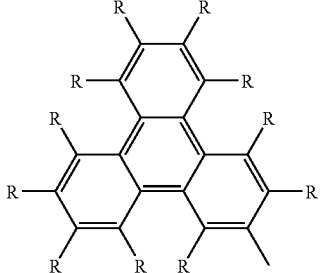
CC12
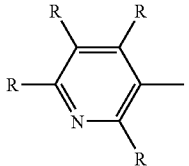
CC14
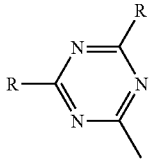
CC16
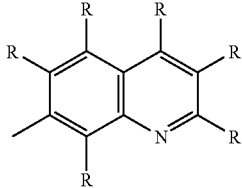
CC18
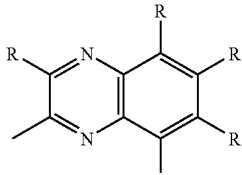
CC20
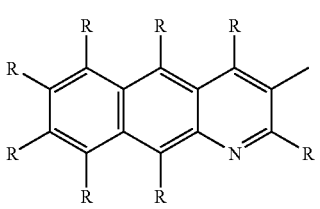
CC22

-continued
| CC23 | CC24 |
|---|---|
| 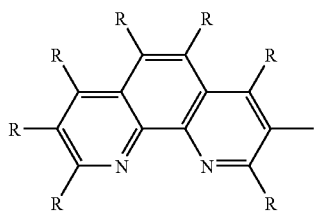 | 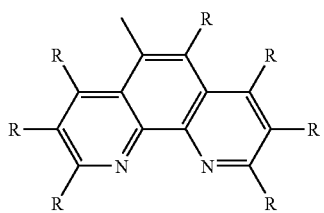 |
| CC25 | CC26 |
|---|---|
| 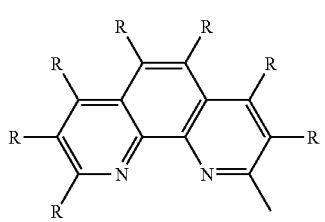 | 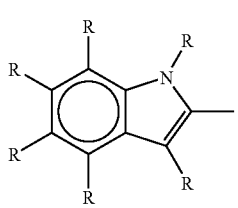 |
| CC27 | CC28 |
|---|---|
| 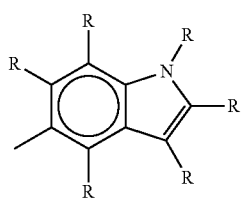 | 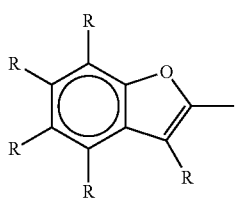 |
| CC29 | CC30 |
|---|---|
| 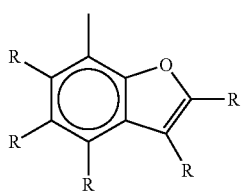 | 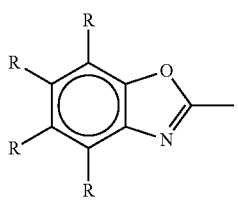 |
CC31
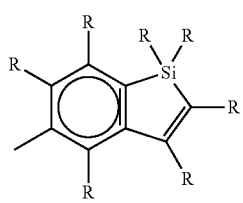
CC32
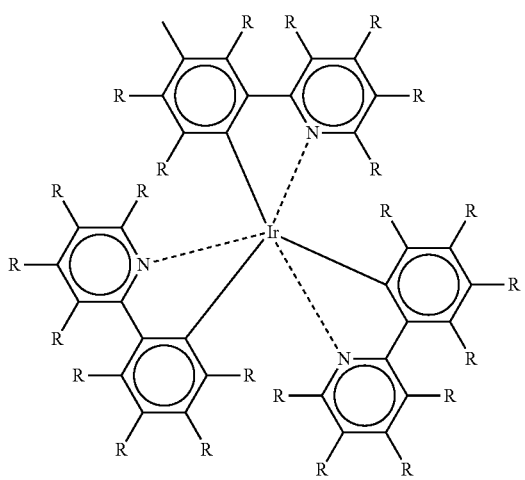

-continued
CC33
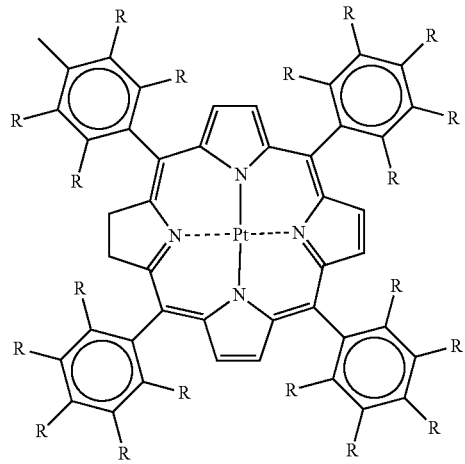
CC34
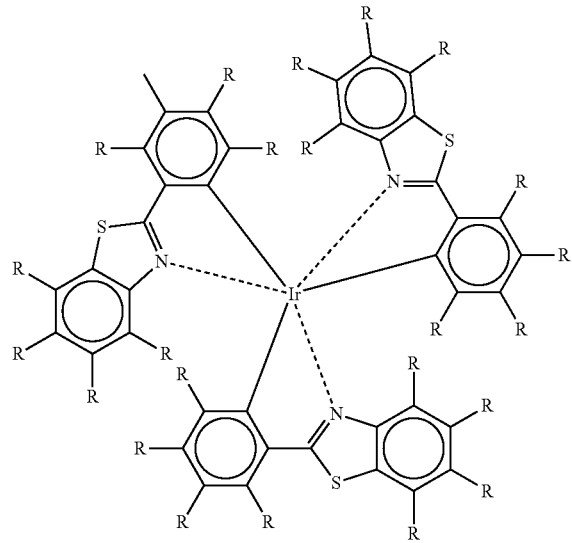
CC35
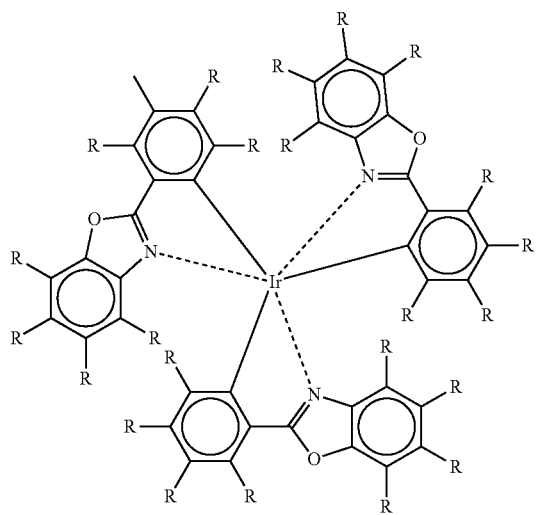
CC36
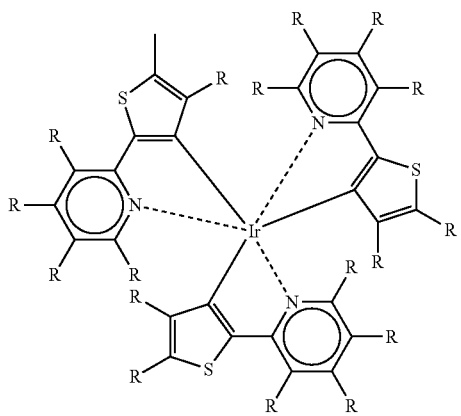
CC37
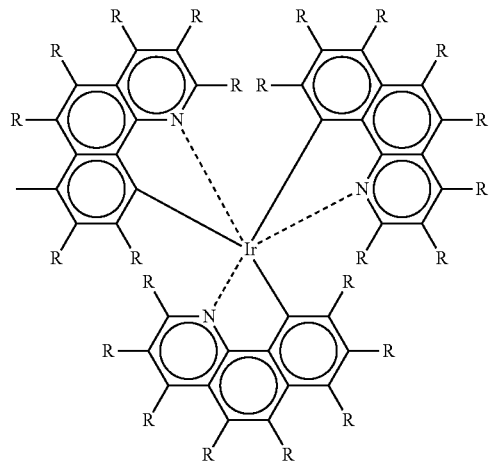
CC38
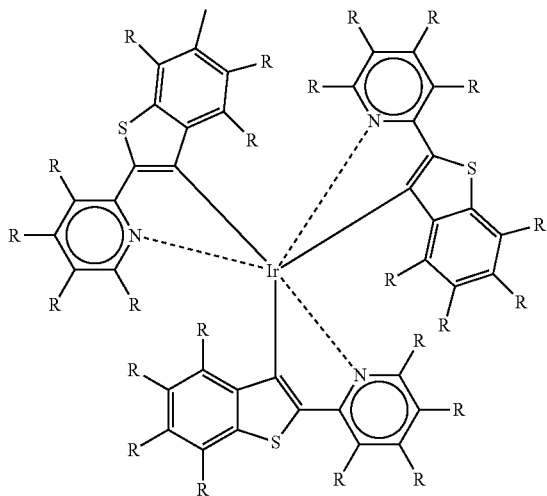

-continued
CC39
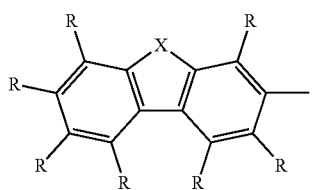
CC40
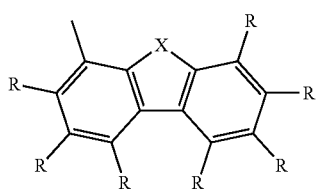
CC41
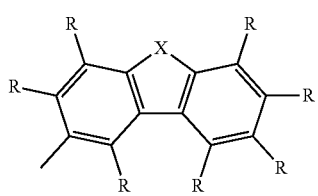
CC42
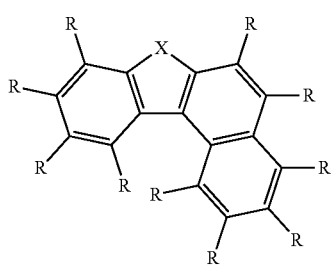
CC43
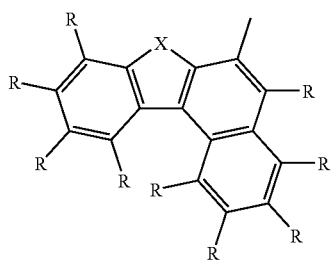
CC44
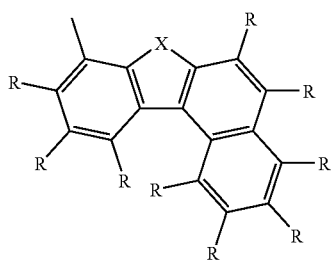
CC45
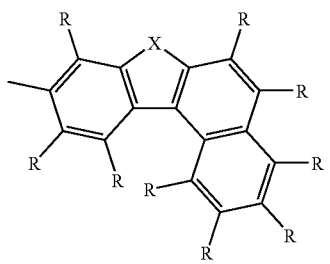
CC46
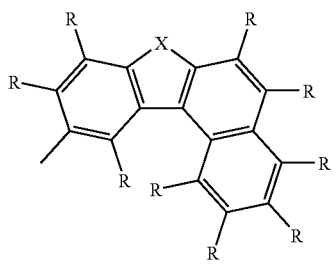
CC47
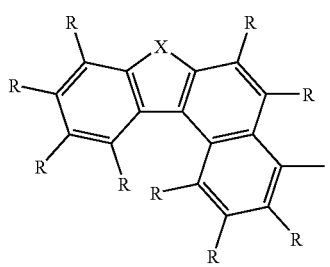
CC48
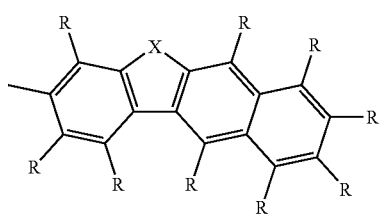
CC49
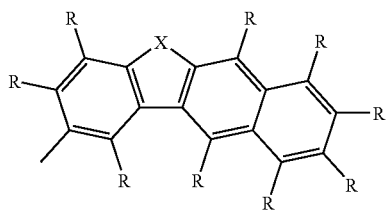
CC50
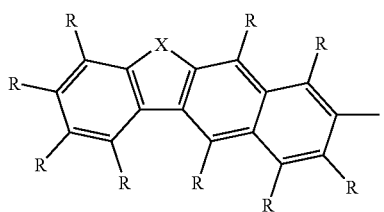

-continued
| | |
|---|---|
| CC51 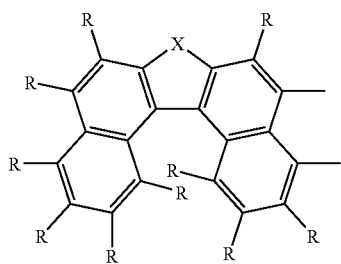 | CC52 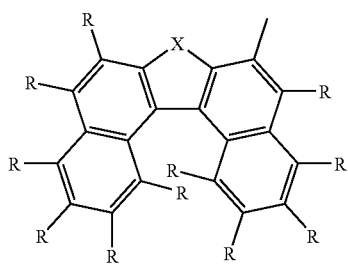 |
| CC53 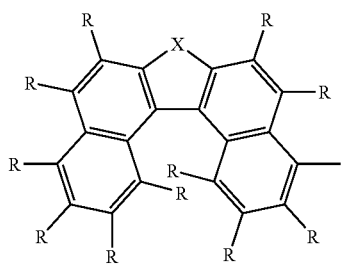 | CC54 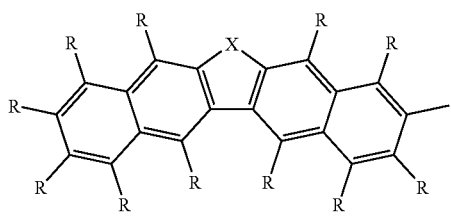 |
| CC55 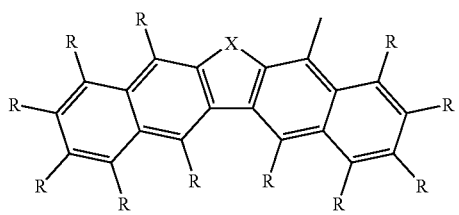 | CC56 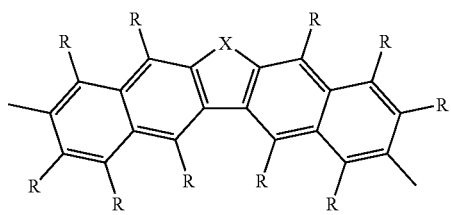 |
| CC57 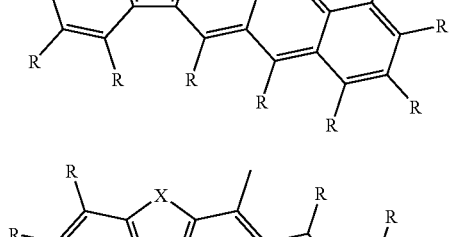 | CC58 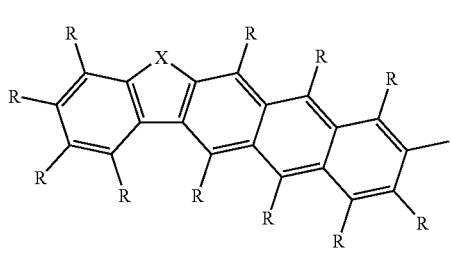 |
| CC59 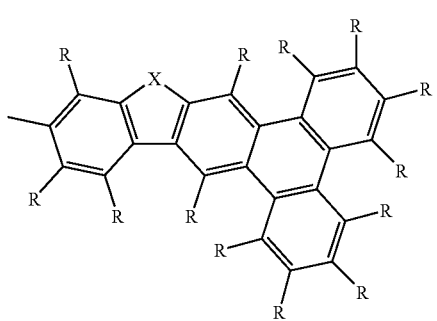 | CC60 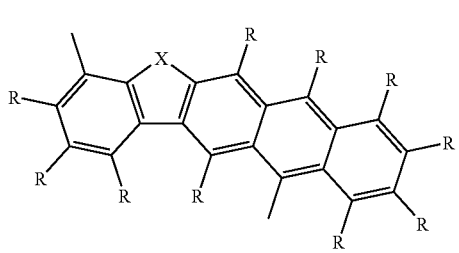 |
| CC61 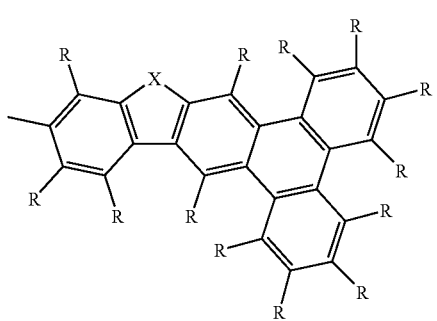 | CC62 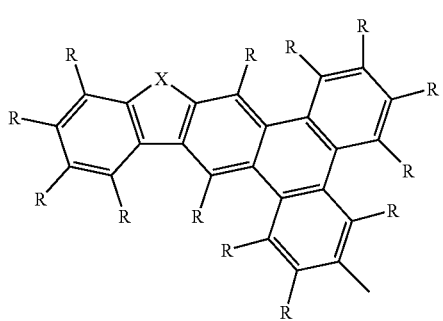 |

-continued
CC63
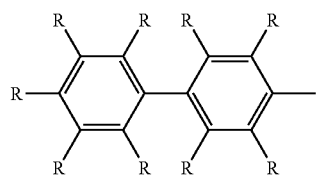
CC64
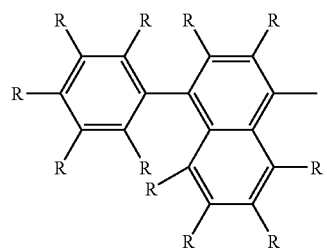
CC65
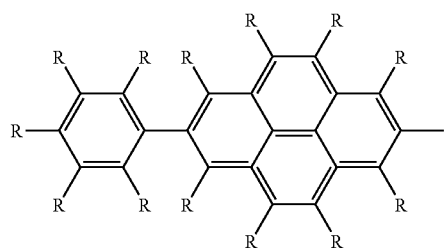
CC66
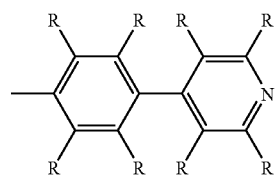
CC67
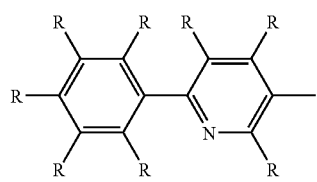
CC68
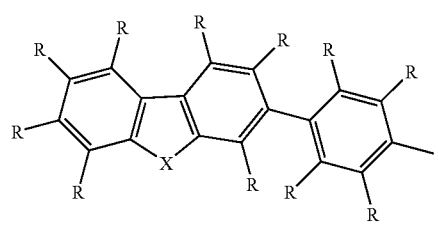
CC69
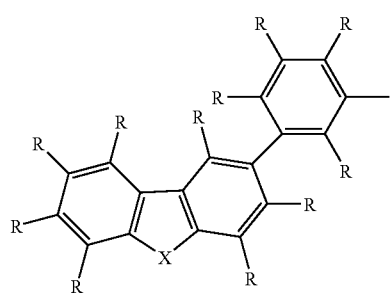
CC70
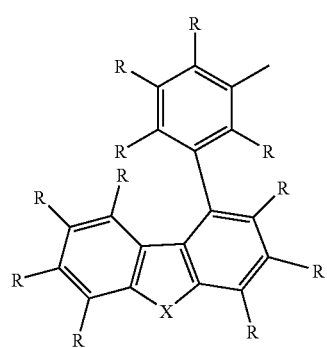
CC71
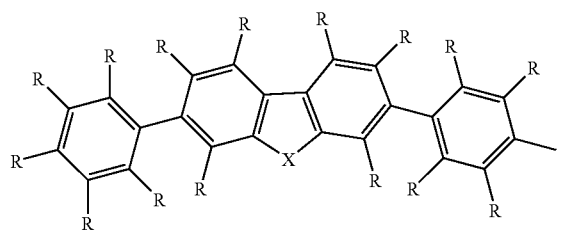
CC72
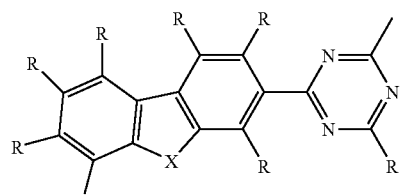
CC73
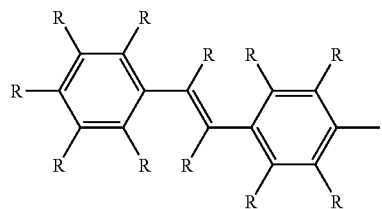
CC74
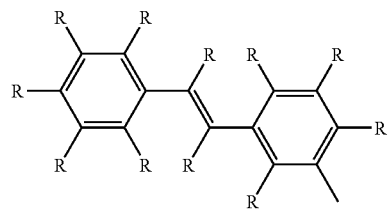

-continued
CC75
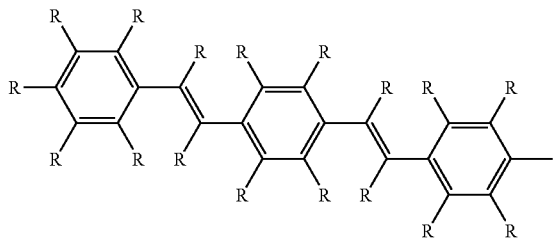
CC76
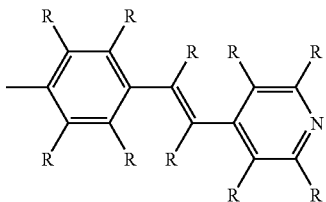
CC77
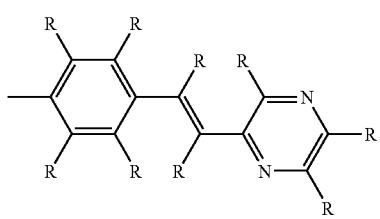
CC78
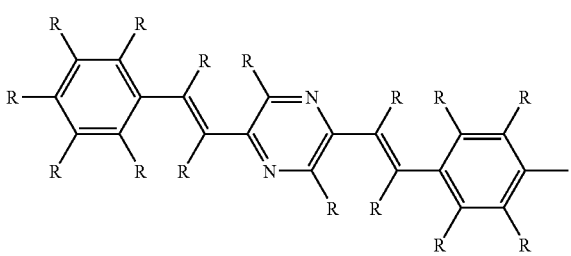
CC79
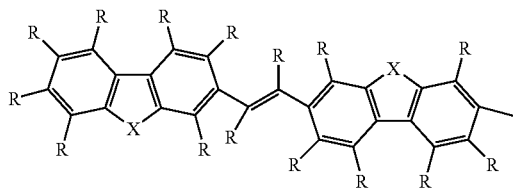
CC80
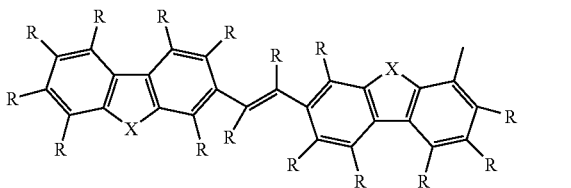
CC81
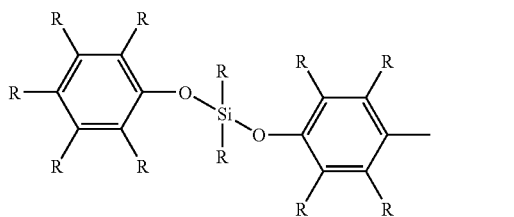
CC82
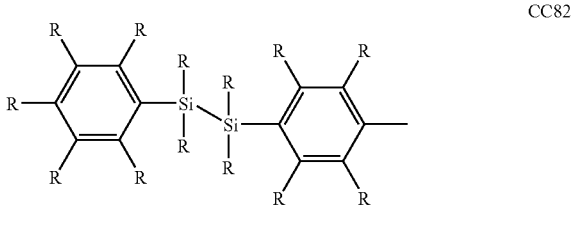
CC83
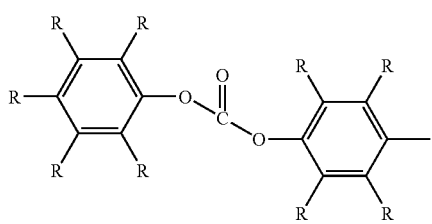
CC84
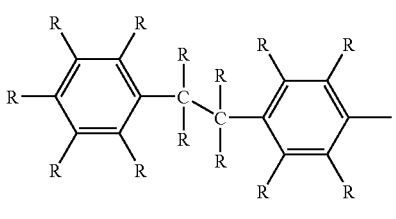
CC85
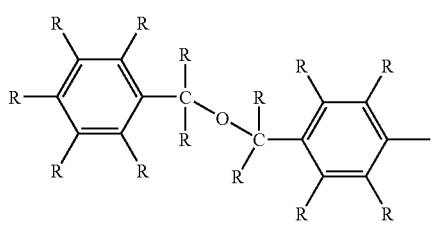
CC86
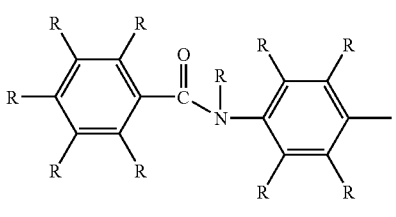
CC87
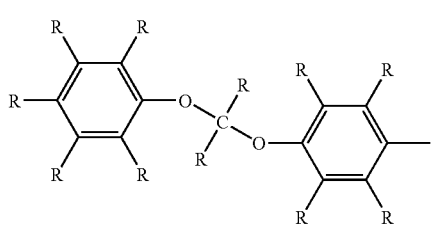
CC87
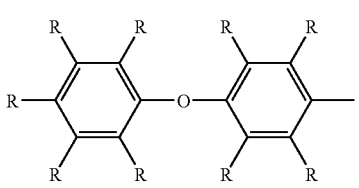

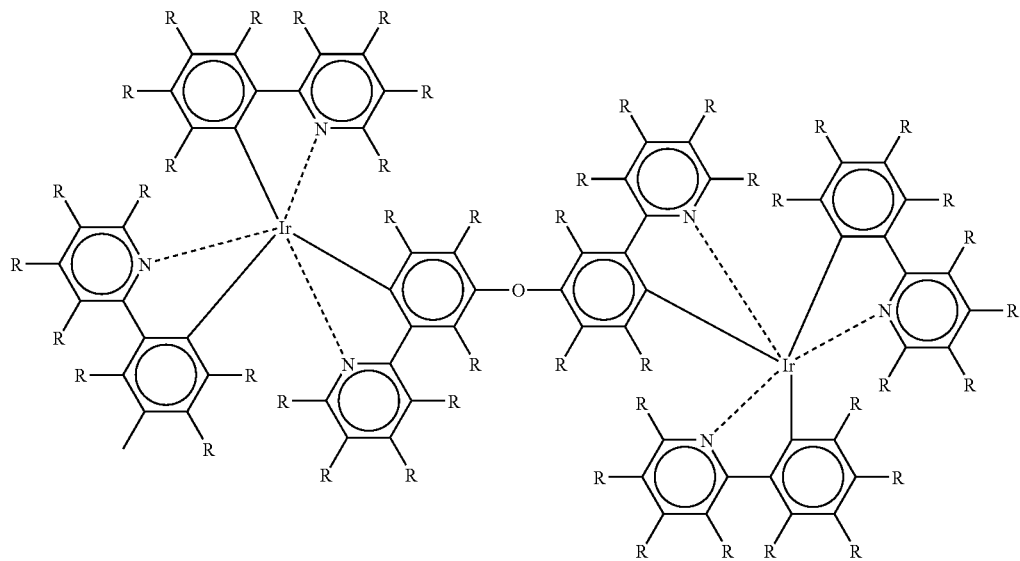
CC88
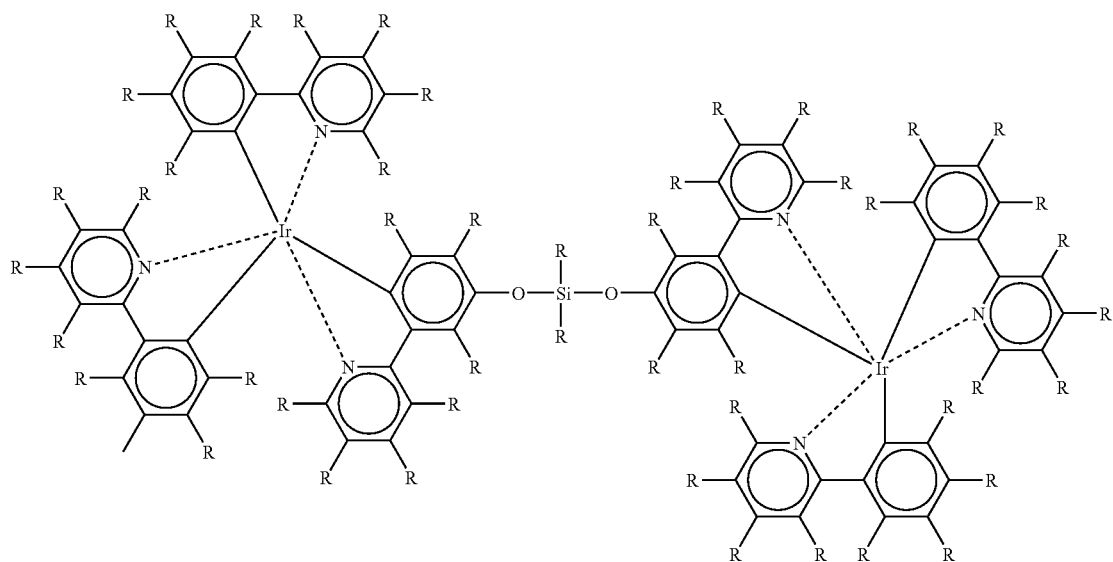
CC89
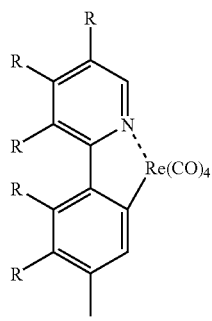
CC90
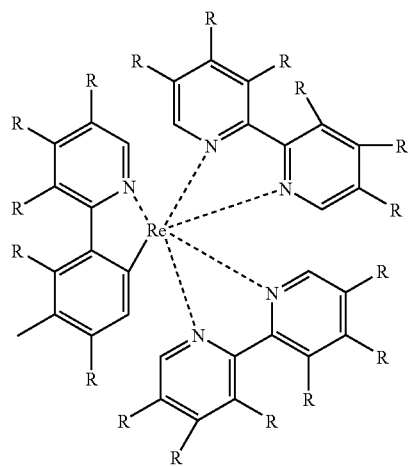
CC91

-continued
CC92
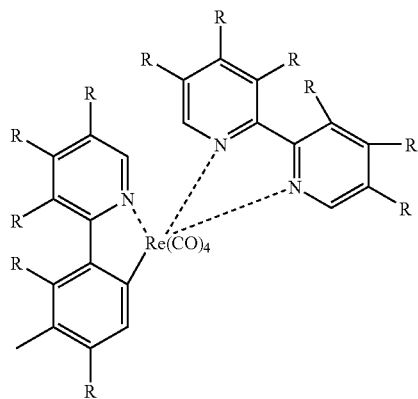
CC93
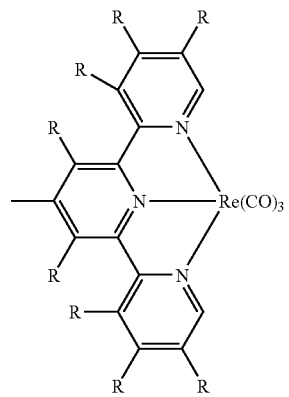
CC94
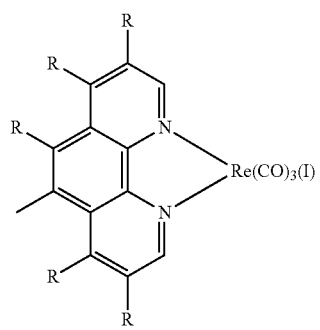
CC95
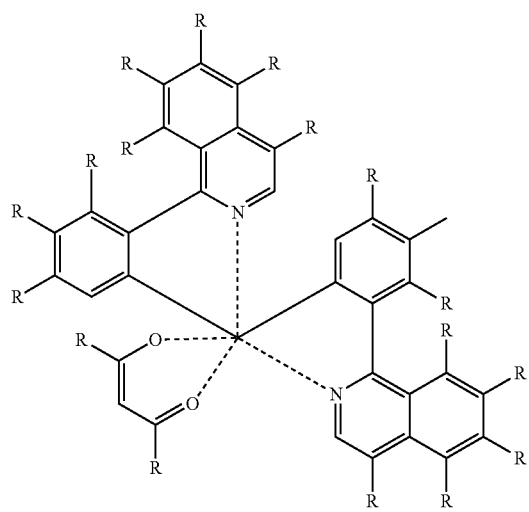
CC96
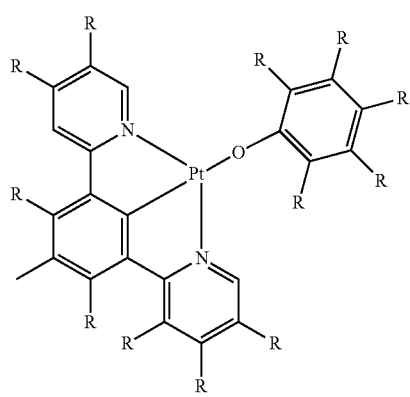
CC97
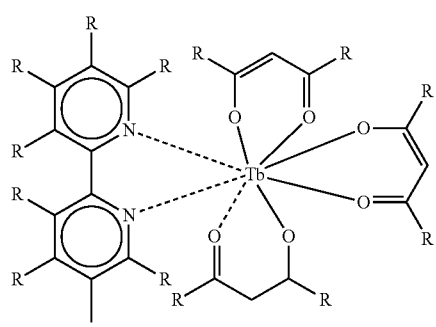

-continued
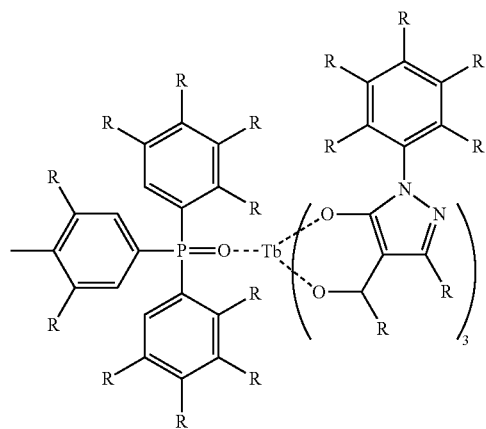
CC98
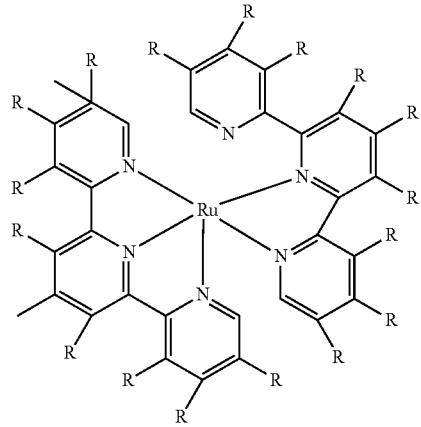
CC99
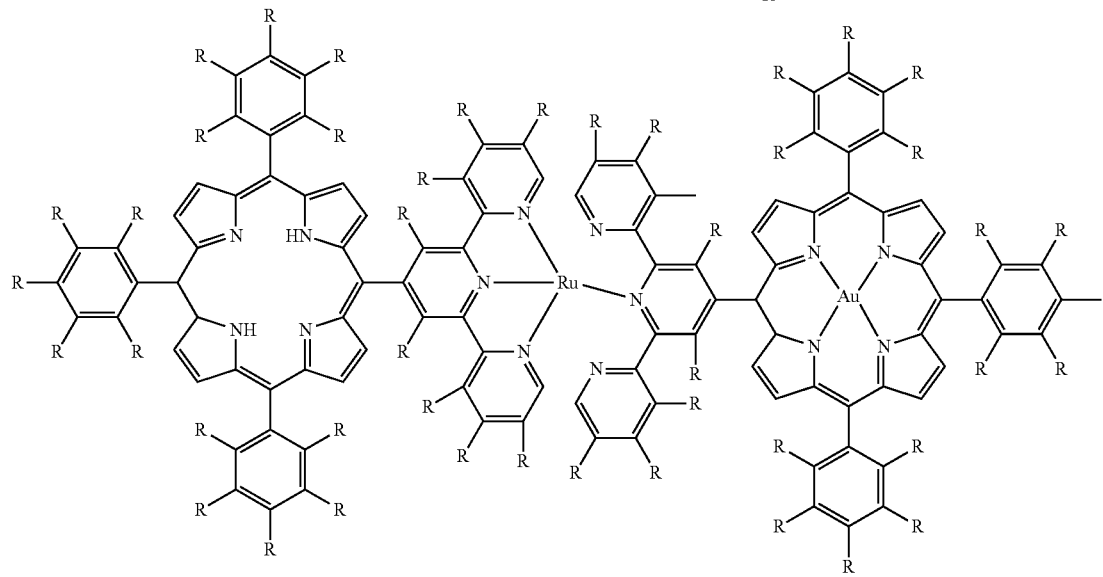
For the following group in formula (1-2),
specific examples include the below divalent aromatic hydrocarbon cyclic groups.
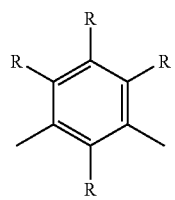
CD1
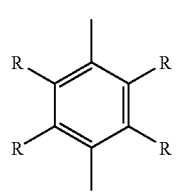
CD2
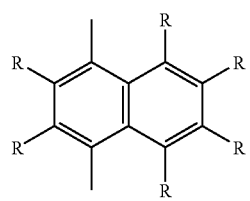
CD3
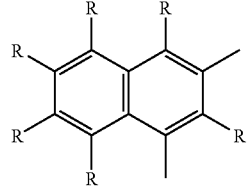
CD4

-continued
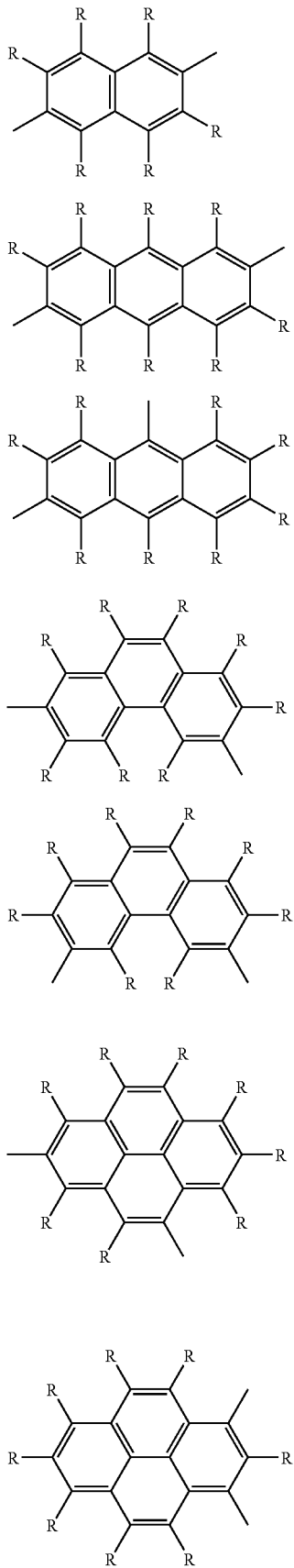
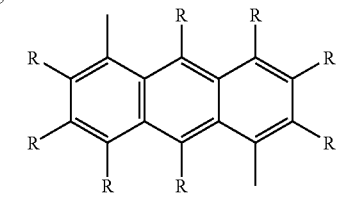
CD5
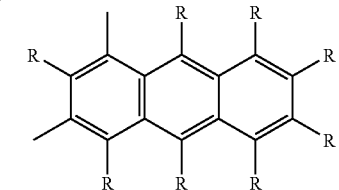
CD6
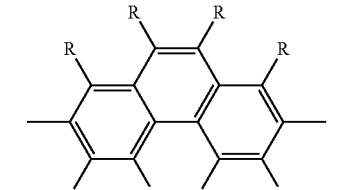
CD7
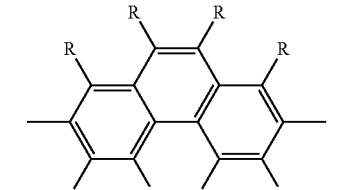
CD8
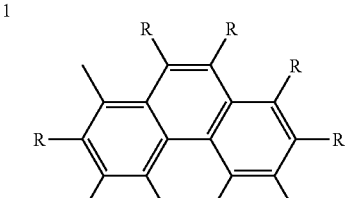
CD9 CD10
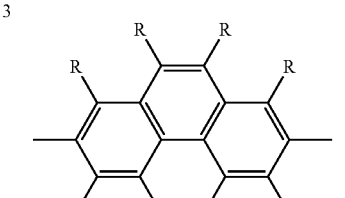
CD11 CD12
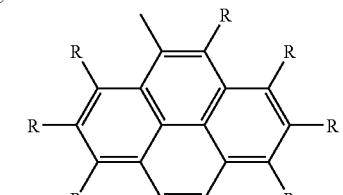
CD13 CD14
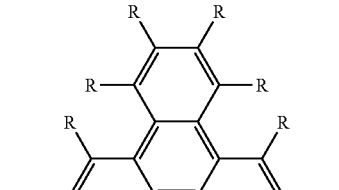
CD15 CD16
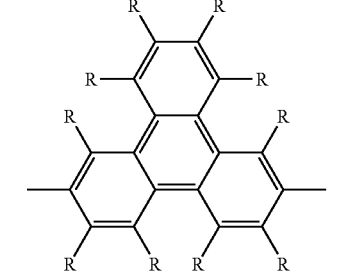
CD17 CD18

-continued
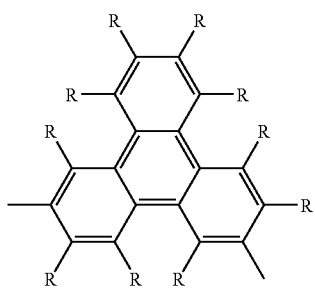
CD19
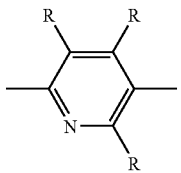
CD20
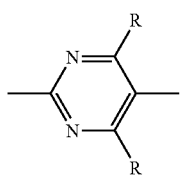
CD21
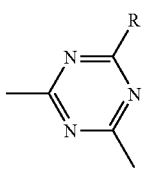
CD22
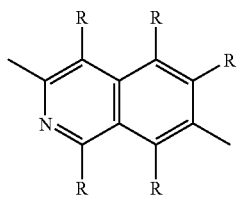
CD23
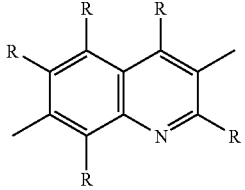
CD24
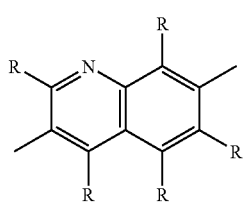
CD25
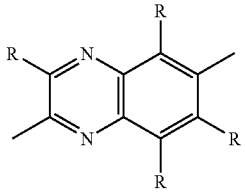
CD26
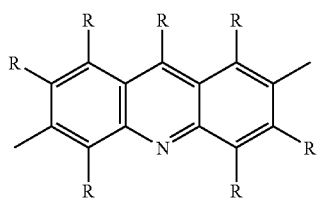
CD27
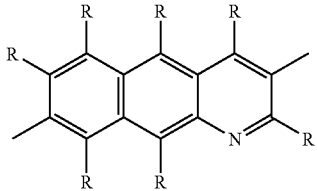
CD28
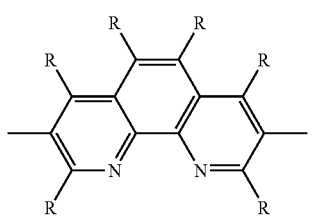
CD29
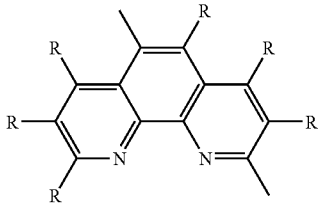
CD30
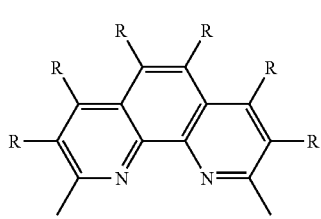
CD31
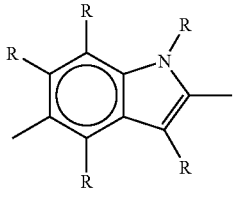
CD32

-continued
CD33 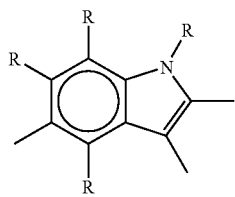
CD34 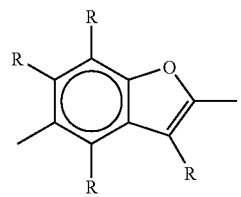
CD35 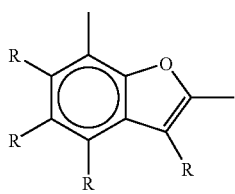
CD36 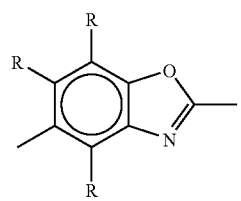
CD37 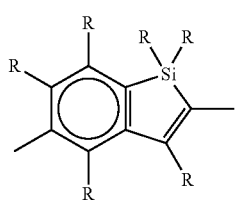
CD38 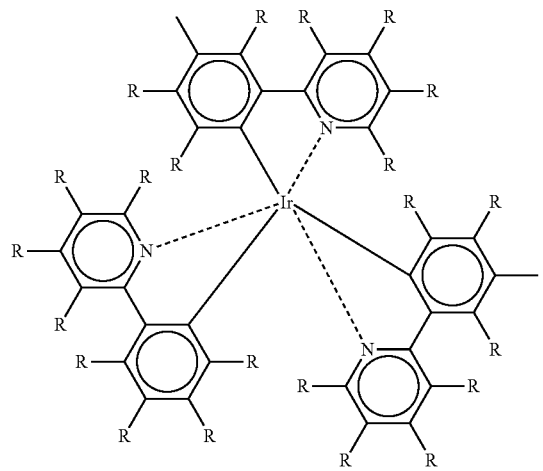
CD39 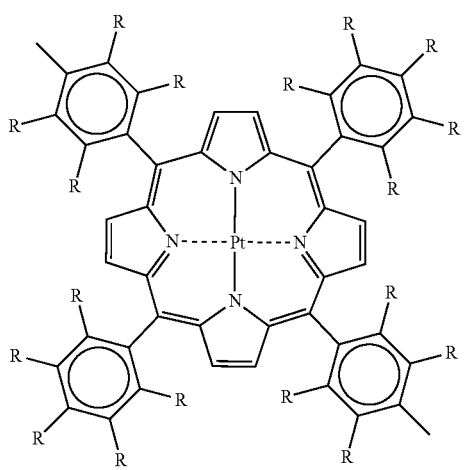
CD40 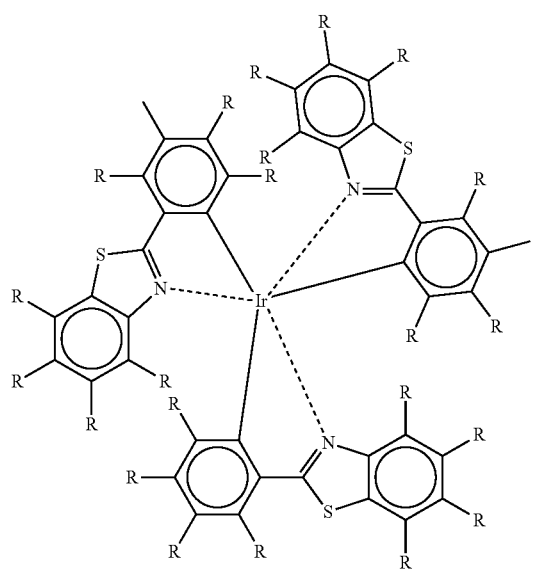

-continued
CD41
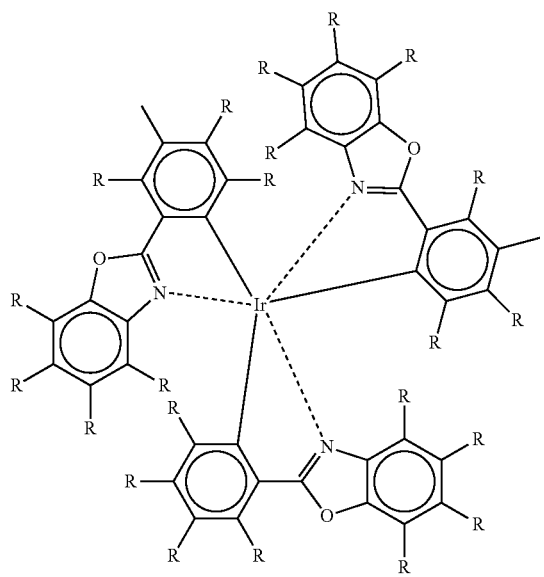
CD42
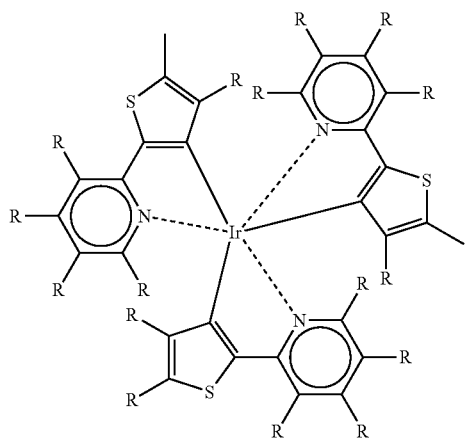
CD43
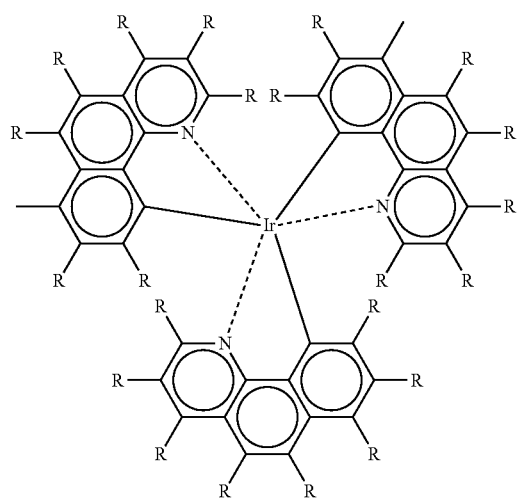
CD44
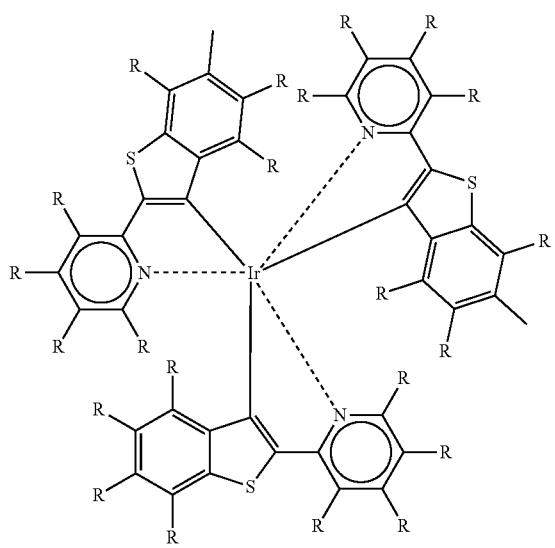
CD45
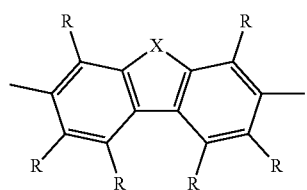
CD46
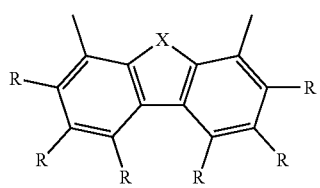
CD47
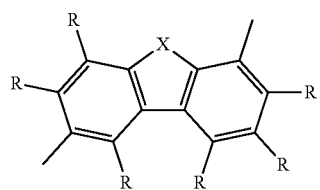
CD48
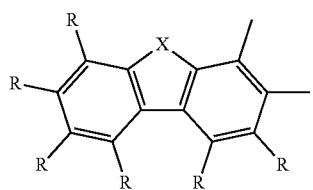

-continued
CD49
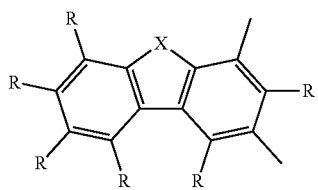
CD50
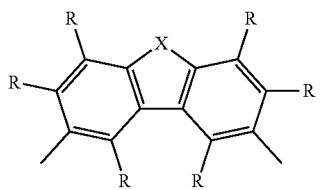
CD51
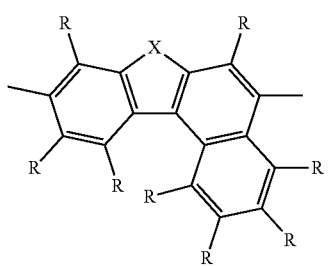
CD52
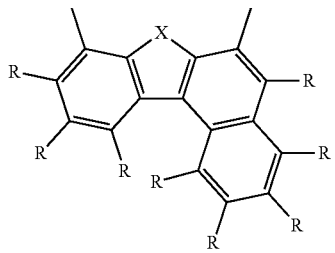
CD53
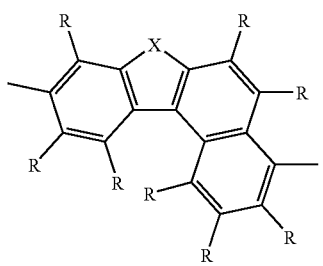
CD54
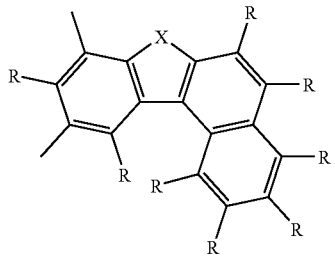
CD55
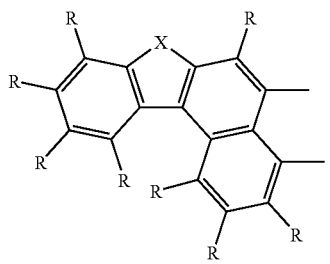
CD56
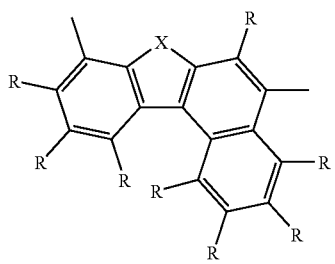
CD57
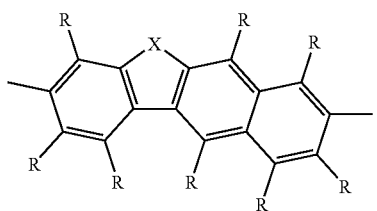
CD58
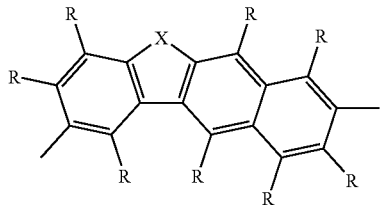
CD59
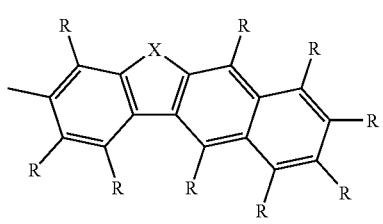
CD60
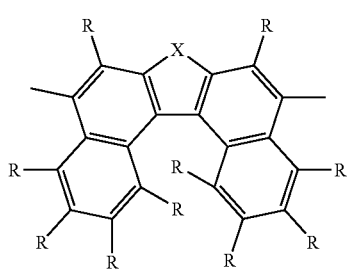

-continued
| | |
|---|---|
| CD61 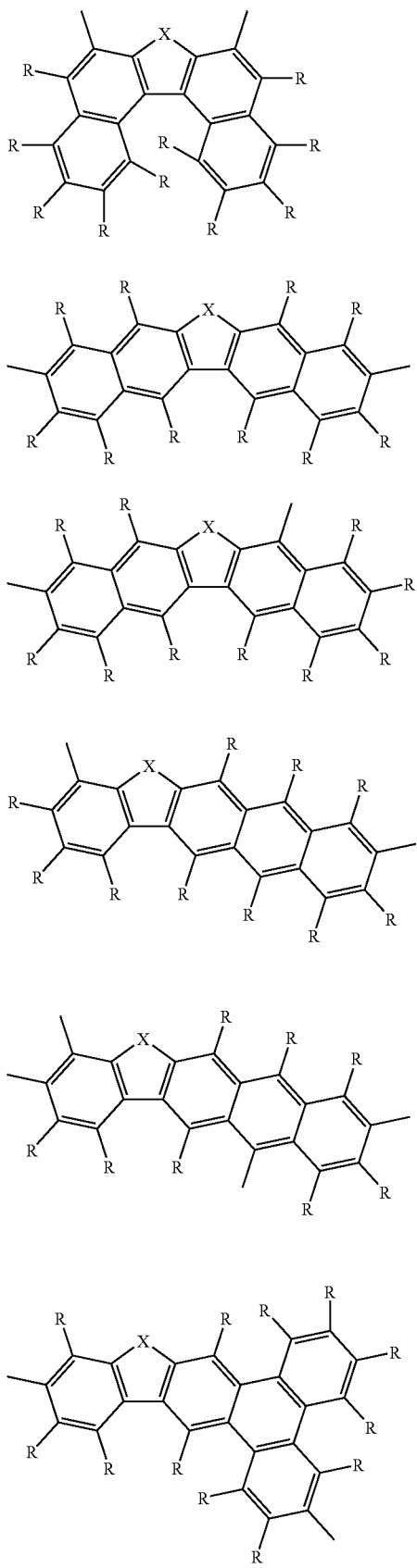 | CD62 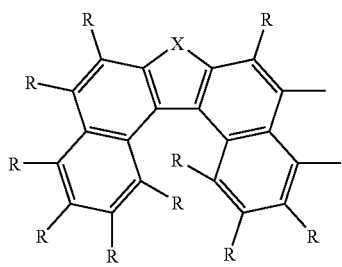 |
| CD63 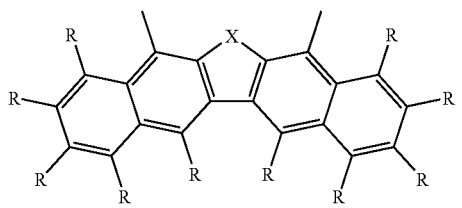 | CD64 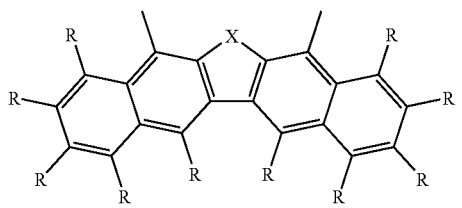 |
| CD65 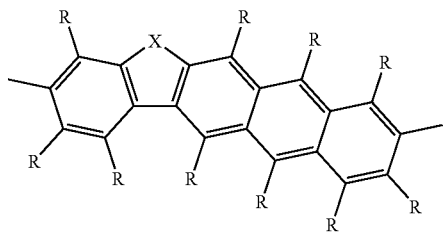 | CD66 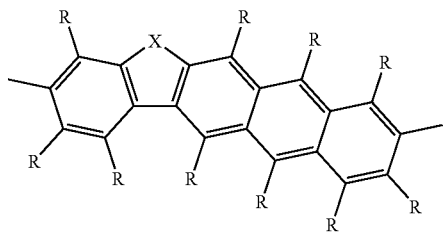 |
| CD67 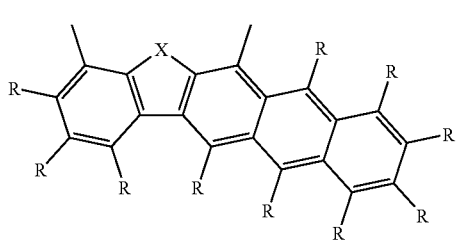 | CD68 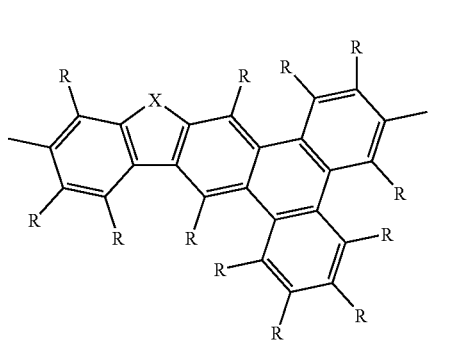 |
| CD69 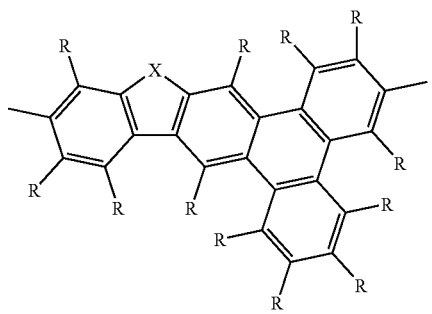 | CD70 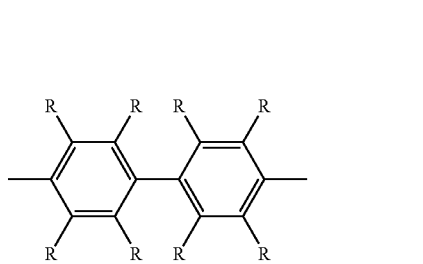 |
| CD71 | CD72 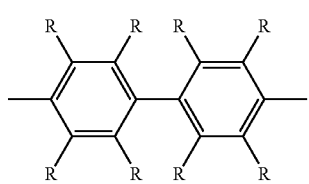 |

-continued
| | |
|---|---|
| CD73 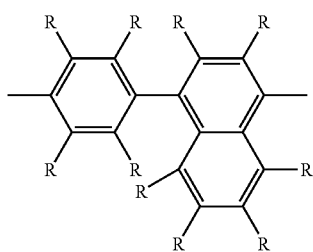 | CD74 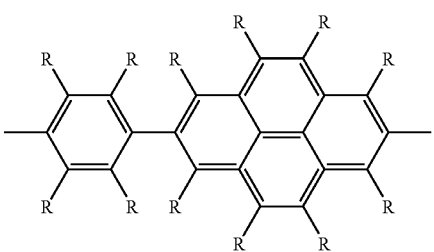 |
| CD75 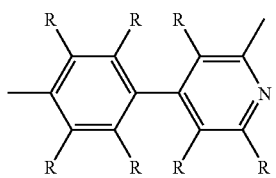 | CD76 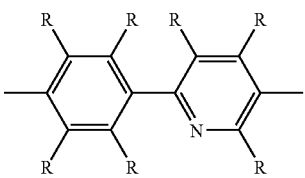 |
| CD77 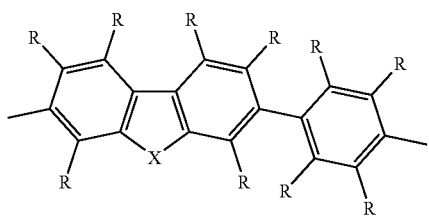 | CD78 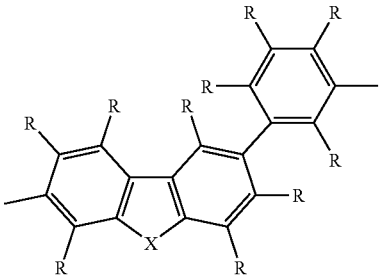 |
| CD79 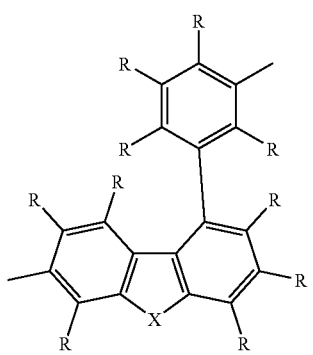 | CD80 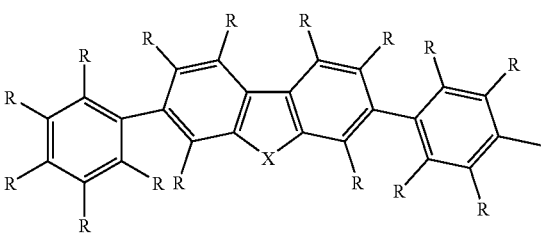 |
| CD81 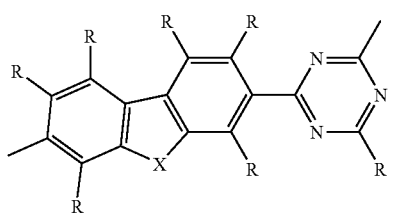 | CD82 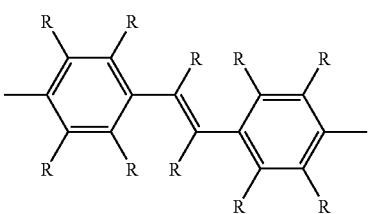 |
| CD83 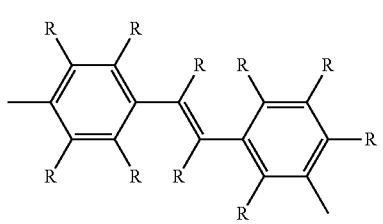 | CD84 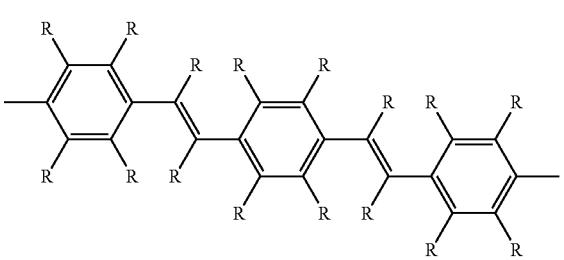 |

-continued
| | |
|---|---|
| CD85 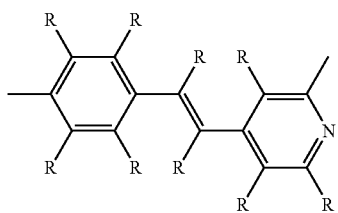 | CD86 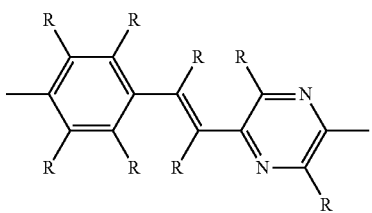 |
| CD87 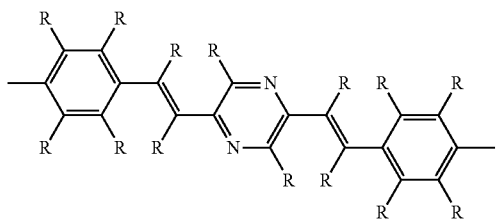 | CD88 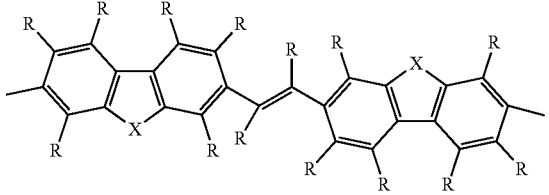 |
| CD89 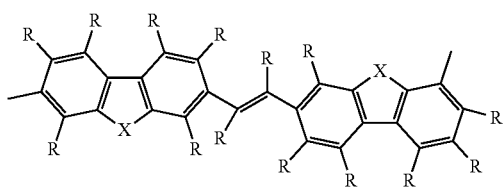 | CD90 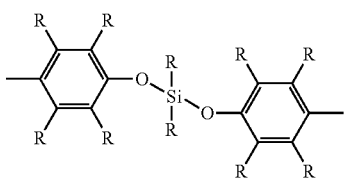 |
| CD91 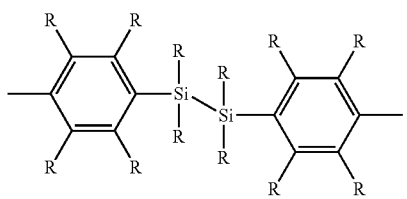 | CD92 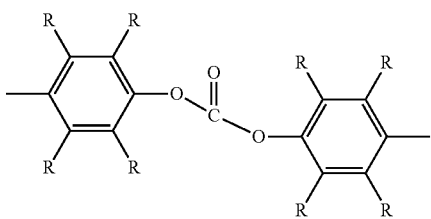 |
| CD93 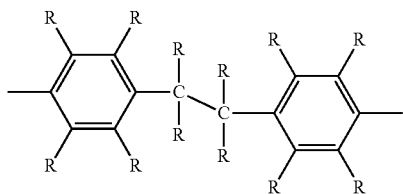 | CD94 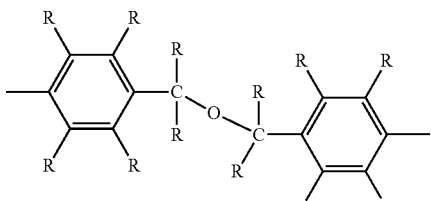 |
| CD95 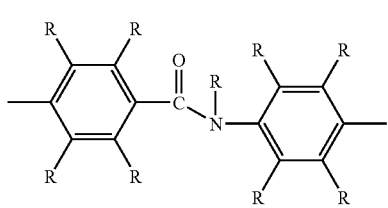 | CD96 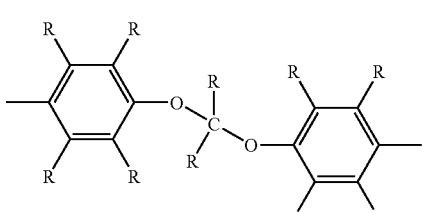 |
| CD97 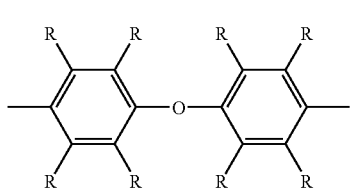 | |

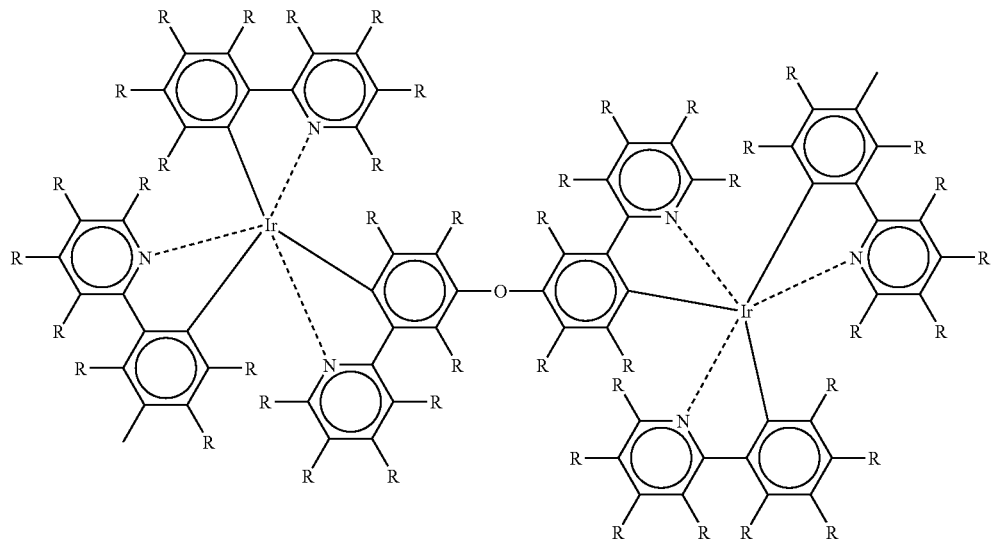
CD98
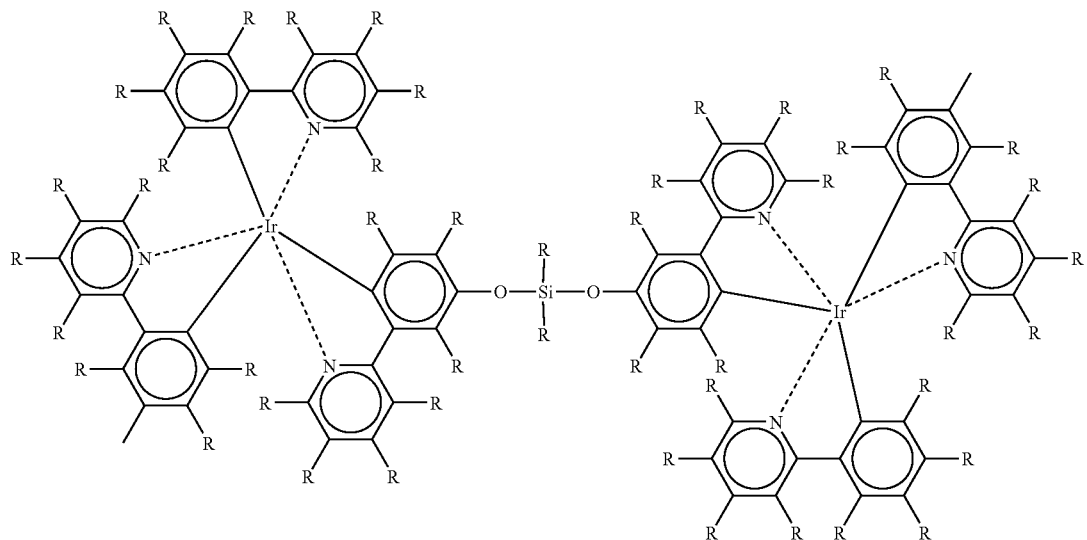
CD99
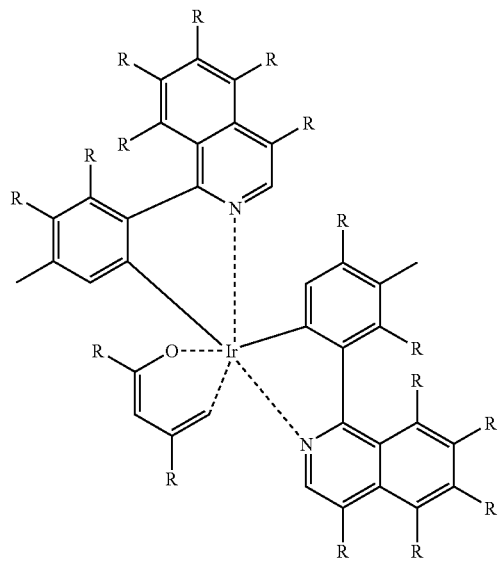
CD100
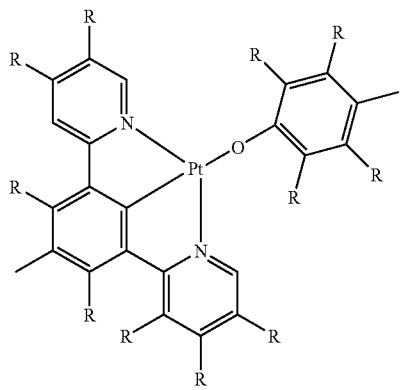
CD101

-continued
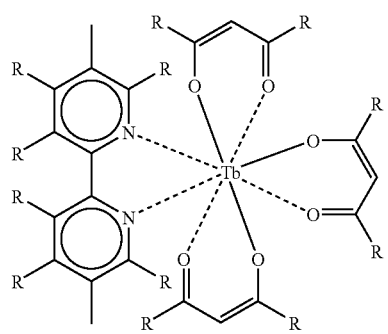
CD102
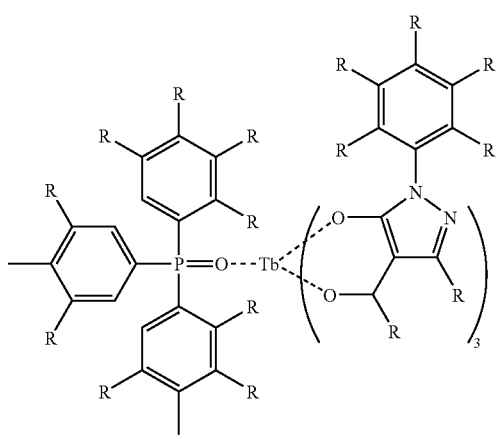
CD103
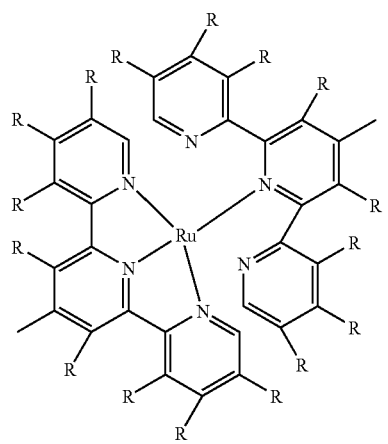
CD104
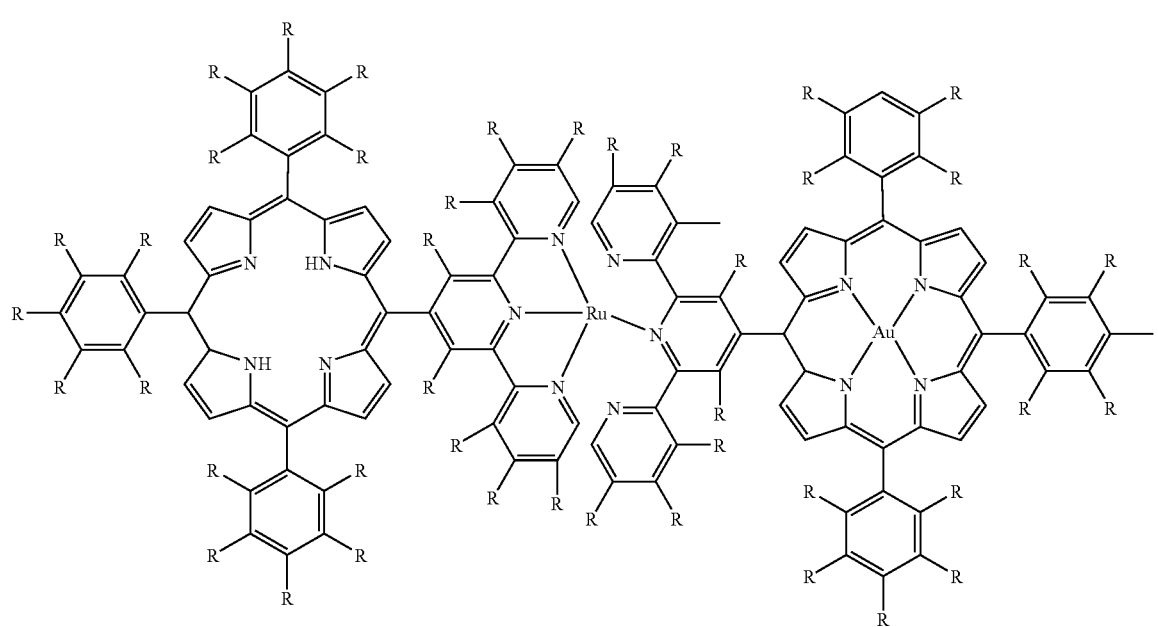
CD105

For the following group in formula (1-3),
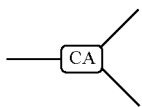
and the following group in formula (3),
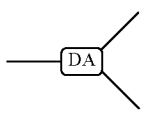
specific examples include the below trivalent aromatic hydrocarbon cyclic groups.
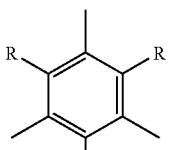
A1
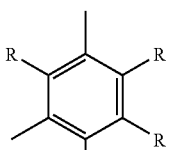
A2
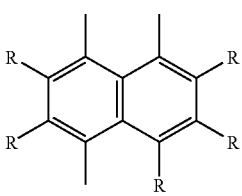
A3
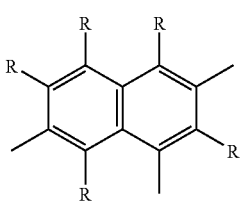
A4
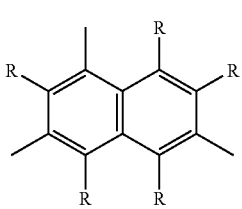
A5
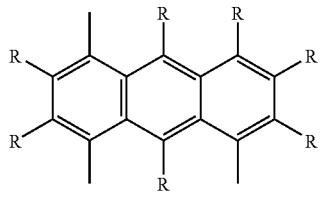
A6
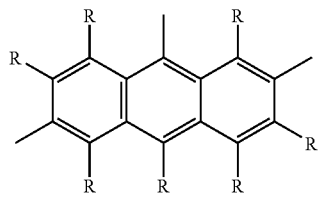
A7
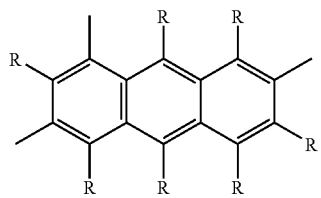
A8
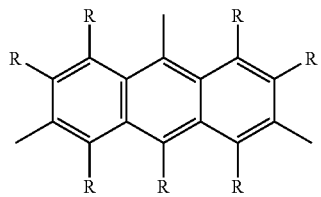
A9
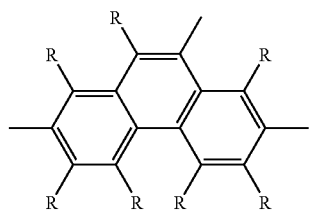
A10
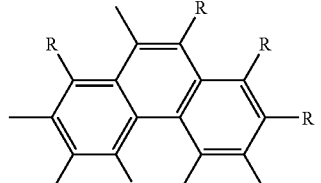
A11
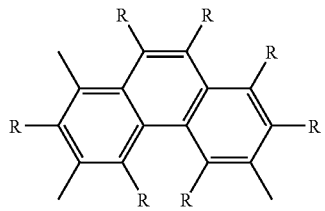
A12

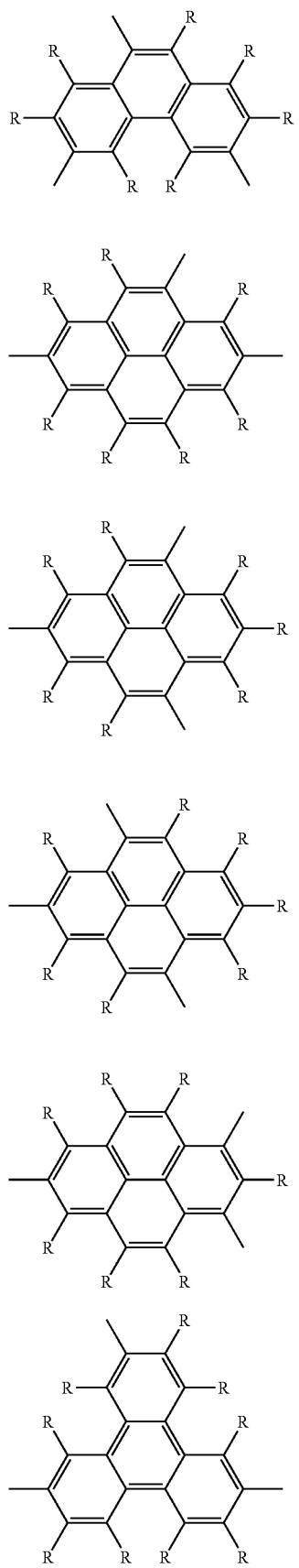
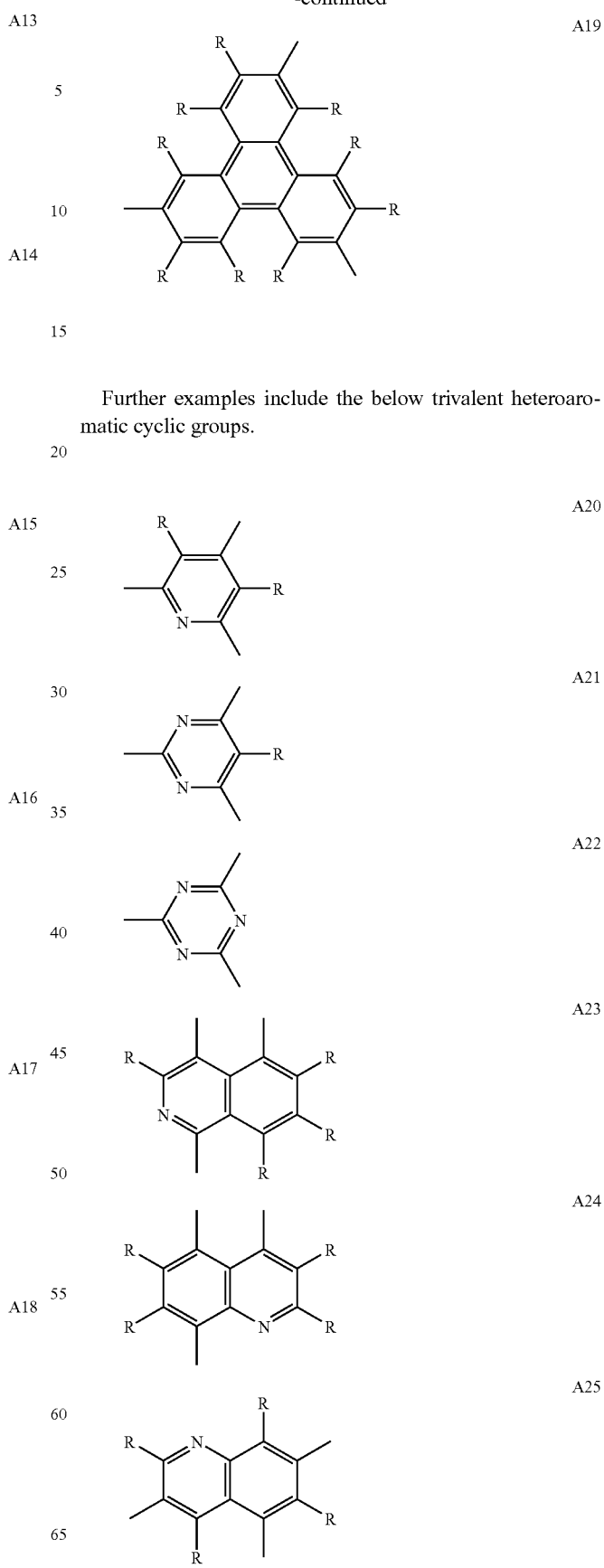
Further examples include the below trivalent heteroaromatic cyclic groups.

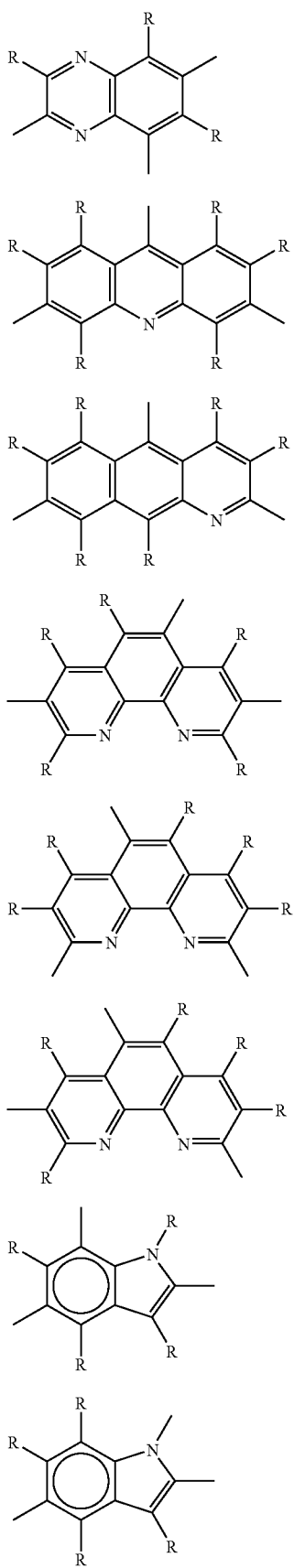
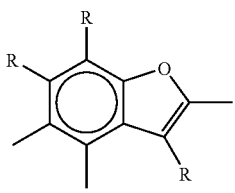
A26
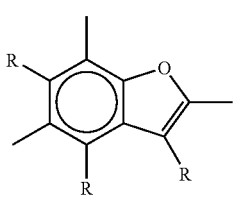
A34
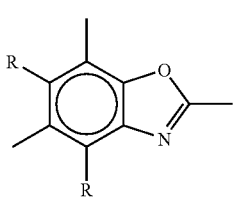
A35
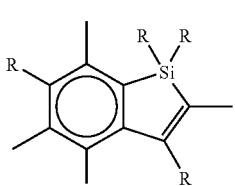
A36
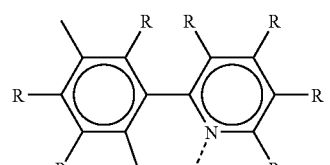
A37
Further examples include the following groups having a trivalent metal complex structure.
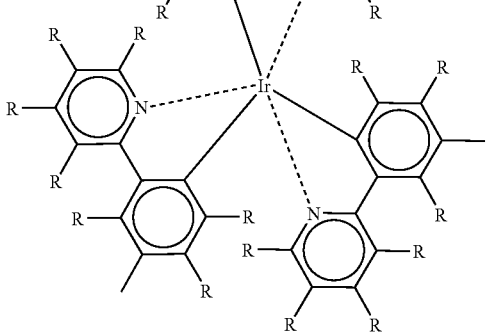
A38

A39
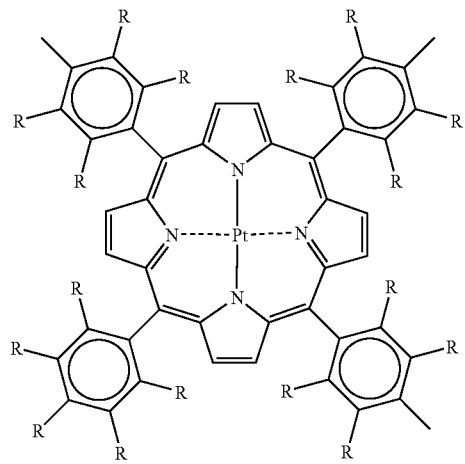
A40
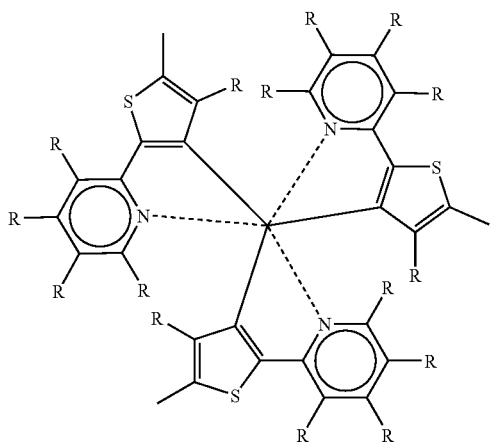
A41
A42
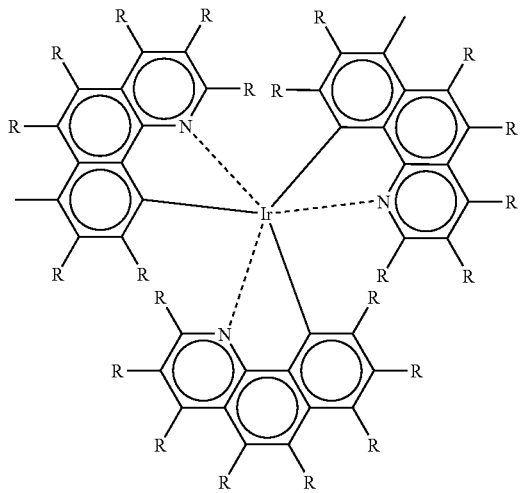
A43
A44
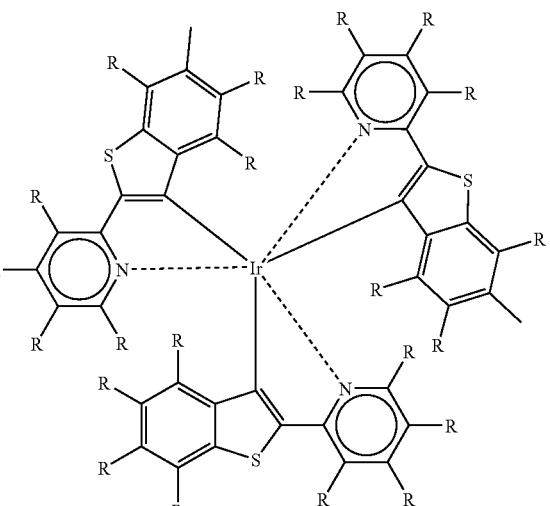
Further examples include the below trivalent groups having a structure represented by the above-described formula (5).

A45 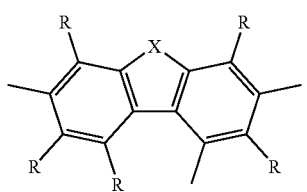
A46 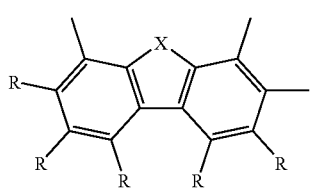
A47 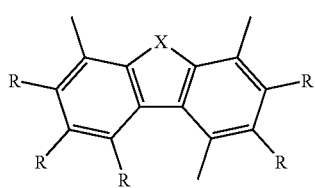
A48 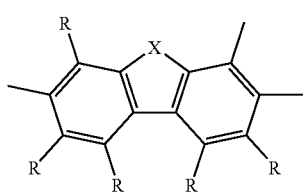
A49 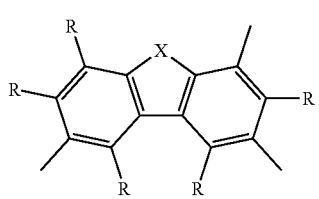
A50 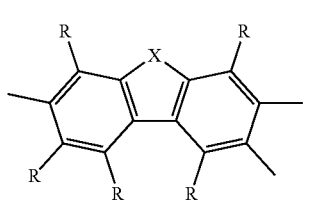
A51 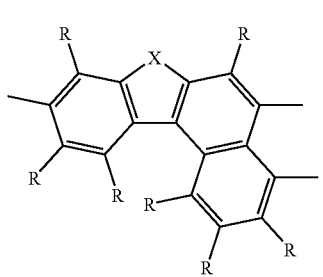
A52 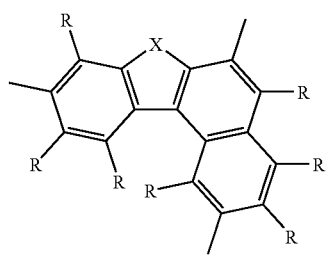
A53 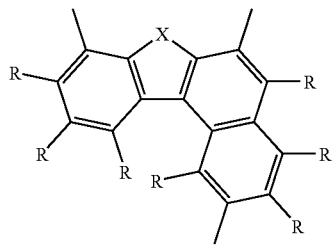
A54 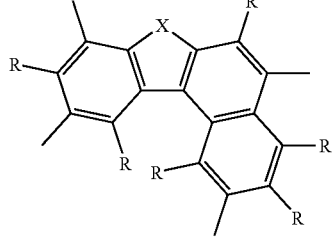
A55 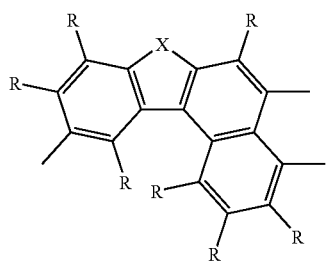
A56 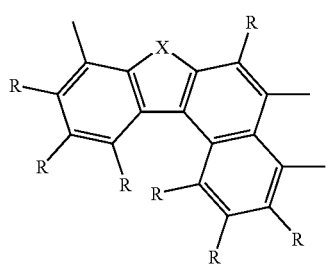
A57 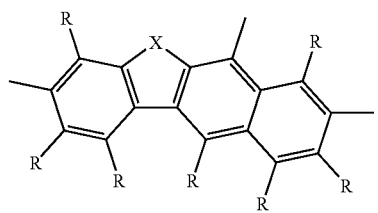

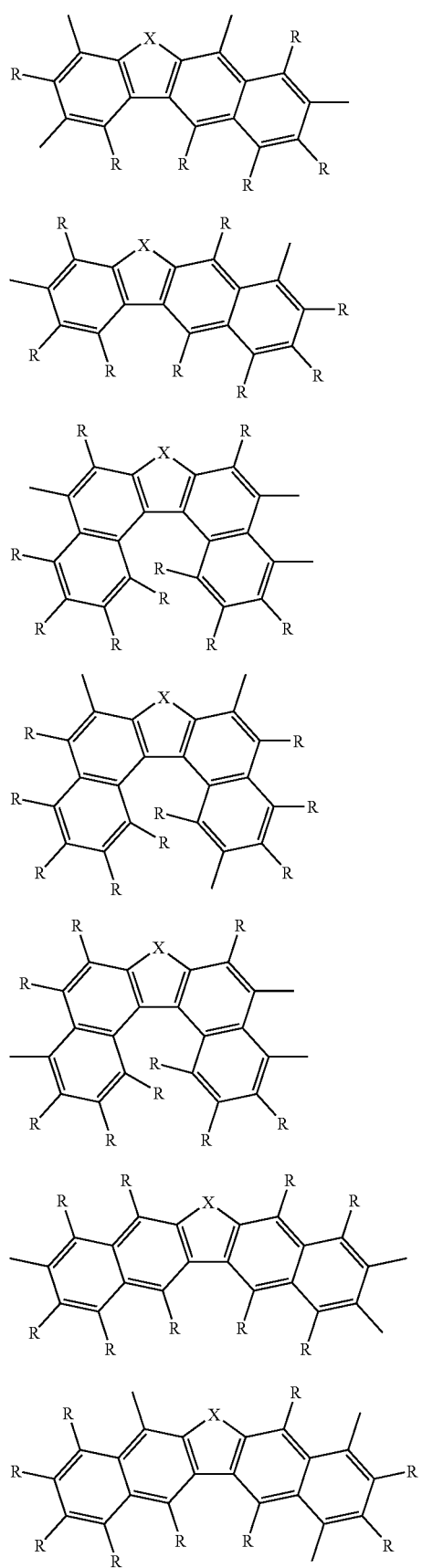
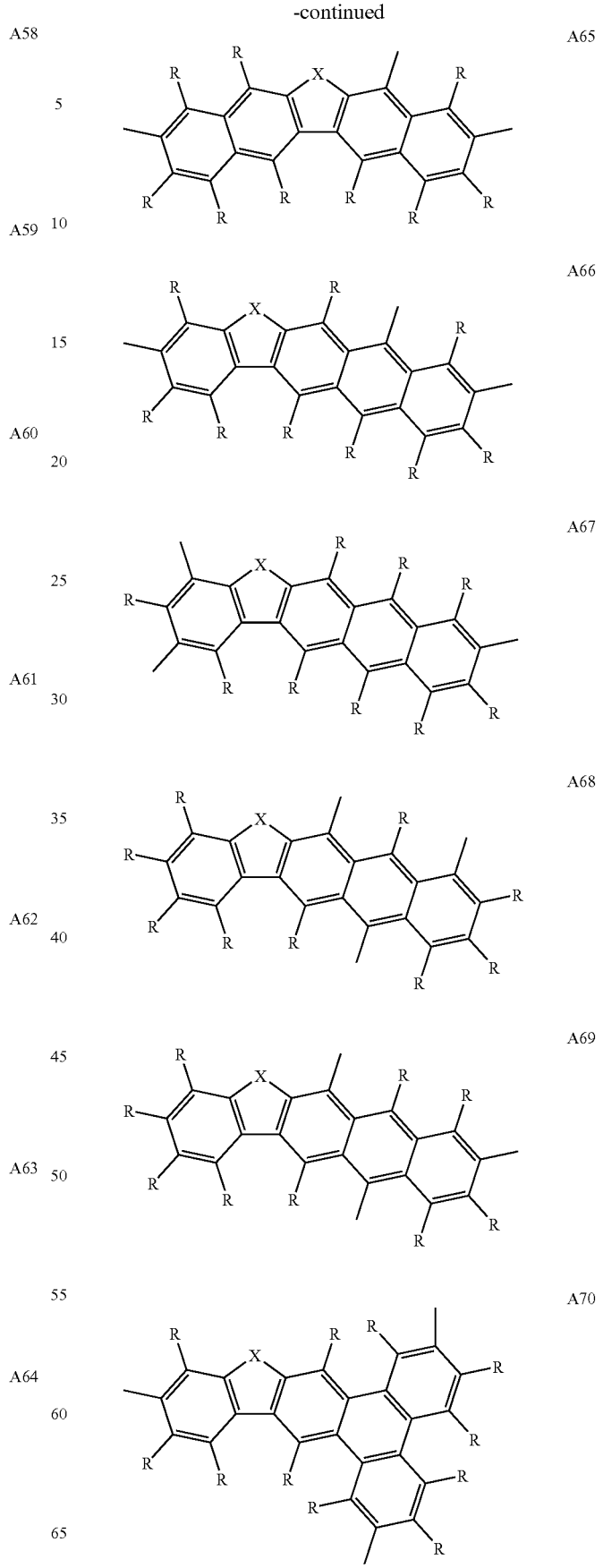

-continued
A71
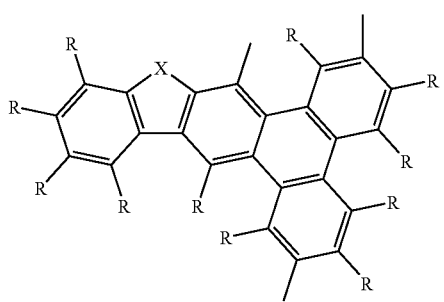
For the following group in formula (1-3),
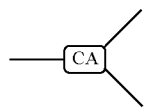
and the following group in formula (3),
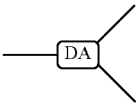
examples include the below trivalent groups in which 2 or more of the same or different structures selected from an aromatic ring, metal complex structure or the structures represented by above formula (5) are connected together.
A72
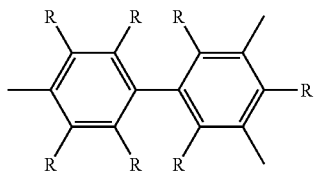
A73
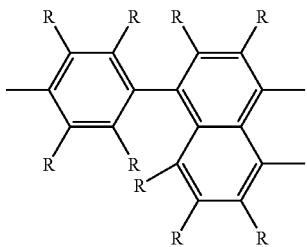
A74
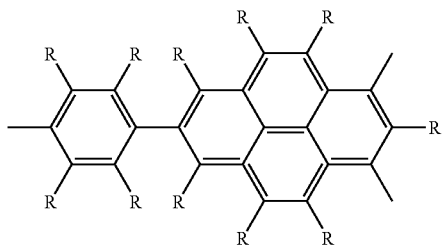
A75
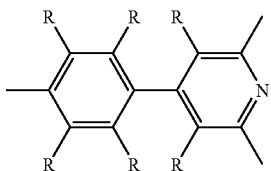
A76
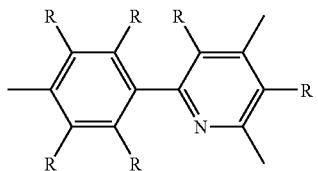
A77
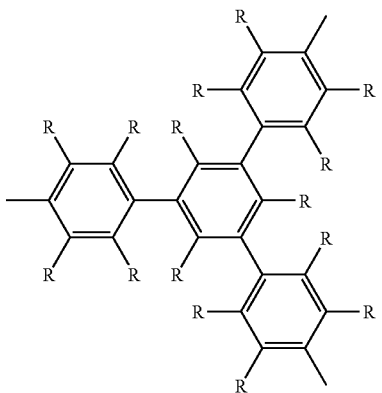

-continued
A78
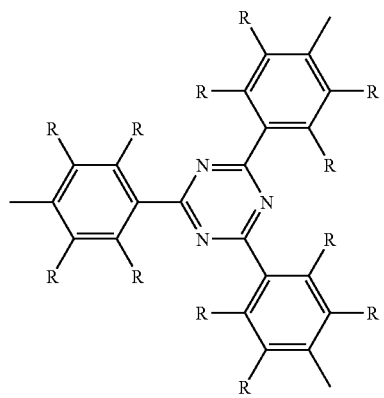
A79
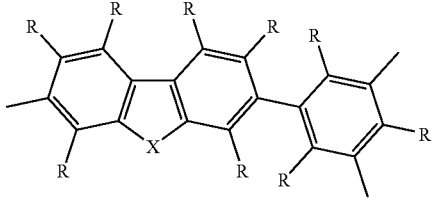
A80
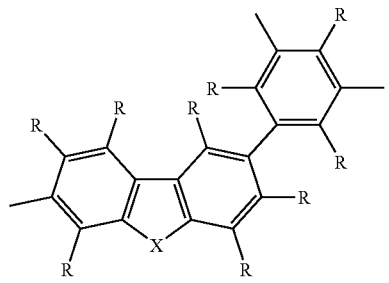
A81
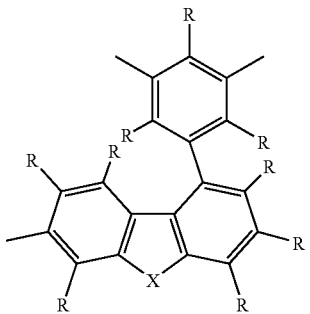
A82
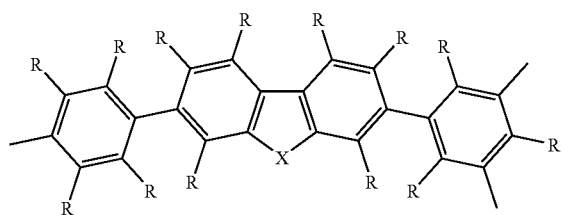
A83
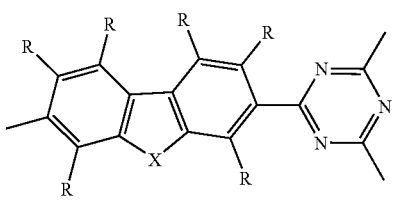
A84
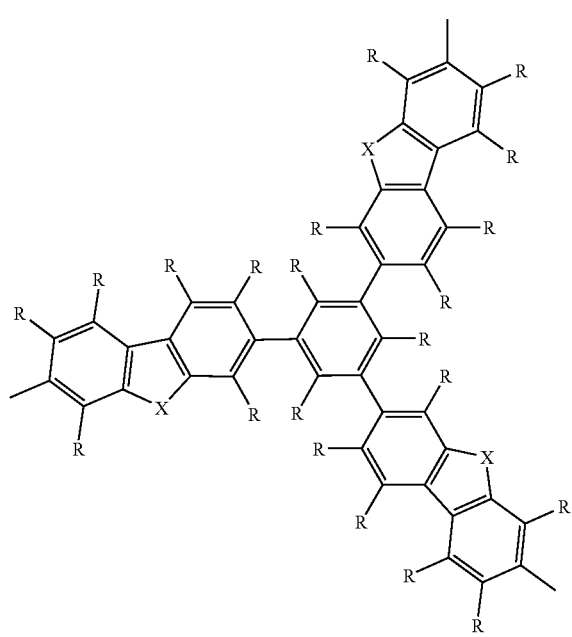

-continued
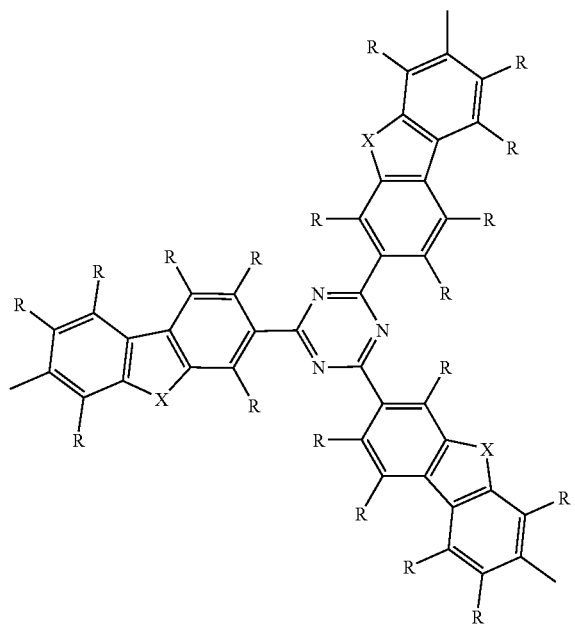
A85
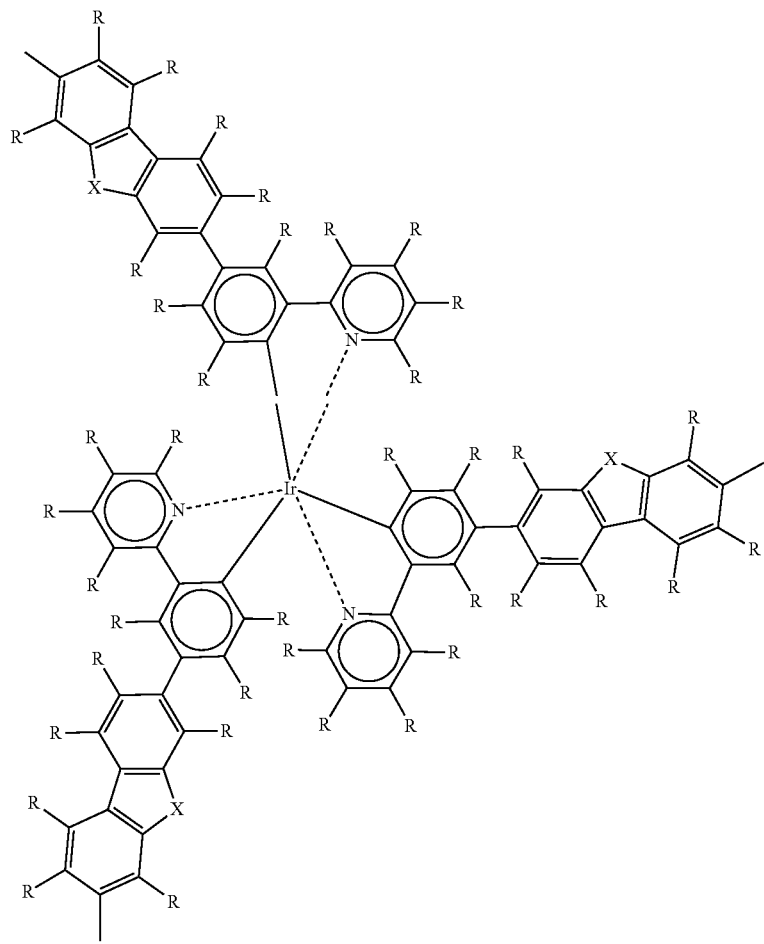
A86

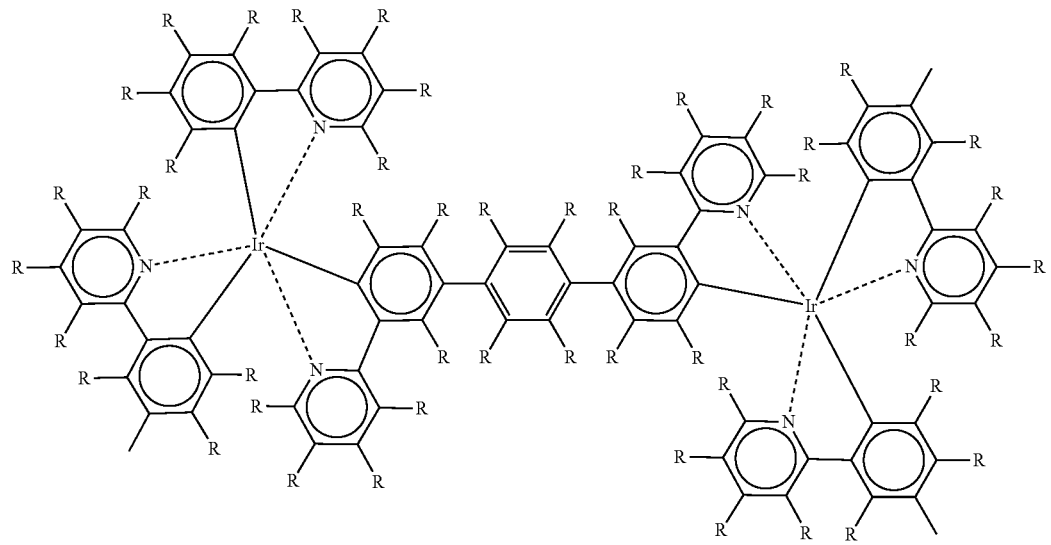
A87
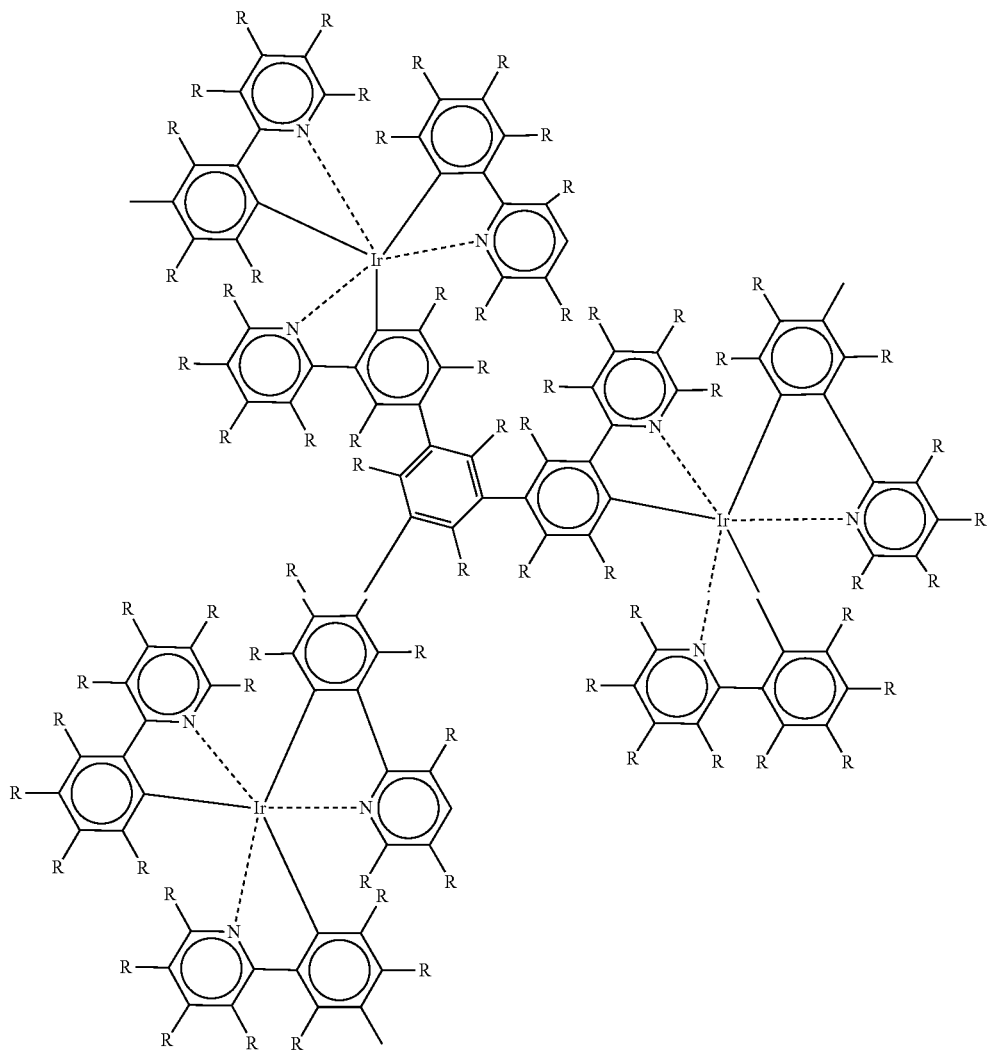
A88

A89
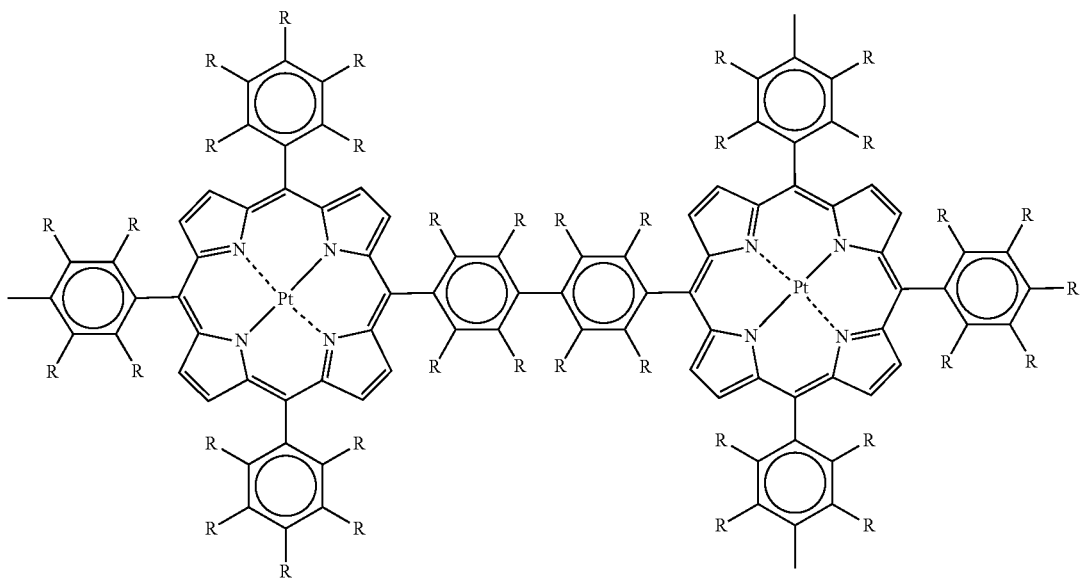
For the following group in formula (1-3),
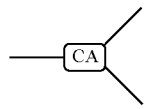
examples include the below trivalent groups in which 2 or more of the same or different structures selected from an aromatic ring, metal complex structure, structures represented by above formula (5) and the like are connected together by a divalent group represented by the above (L-1).

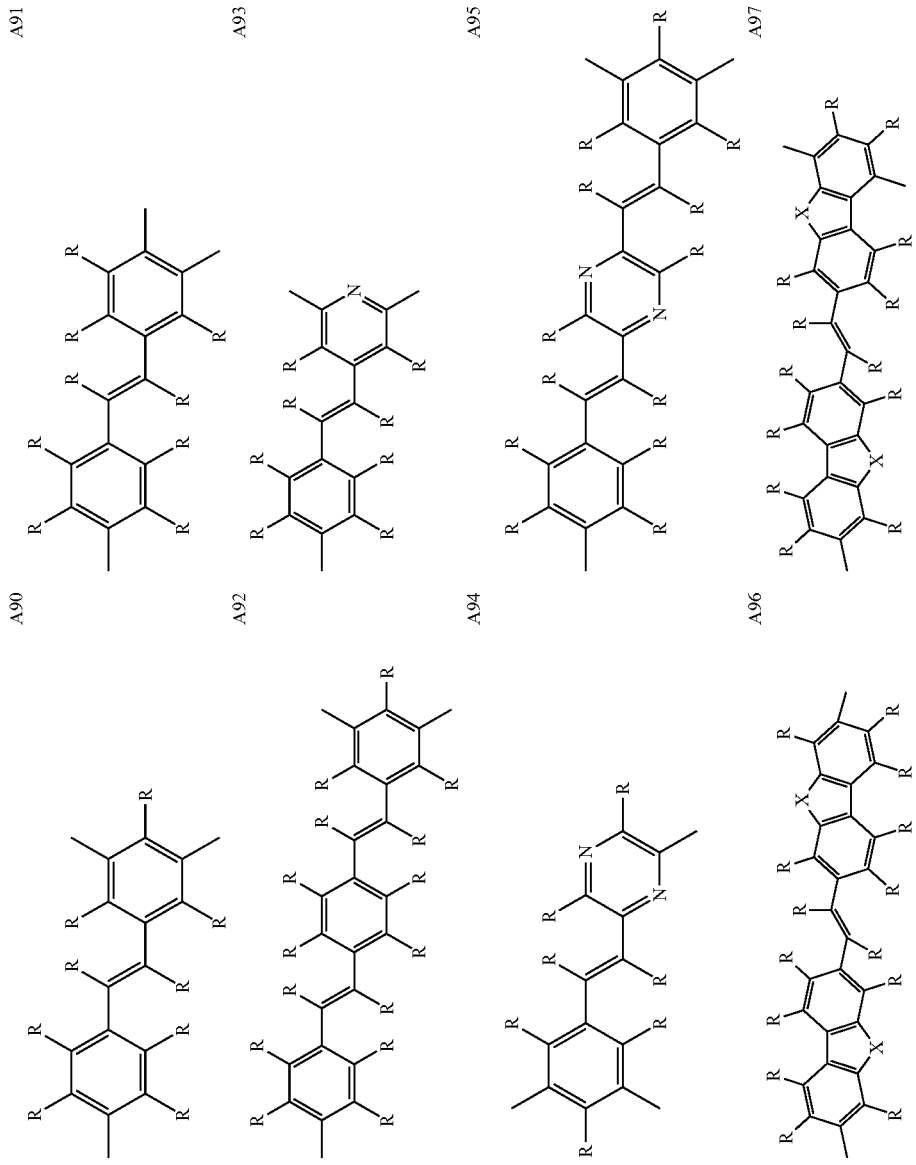

-continued
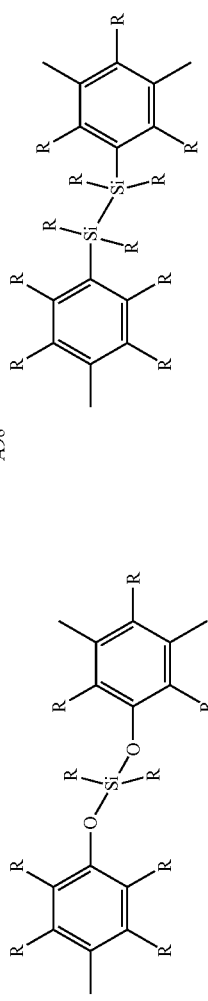
A98
A99
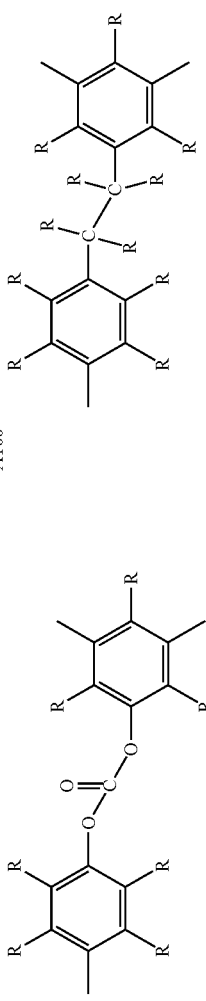
A100
A101
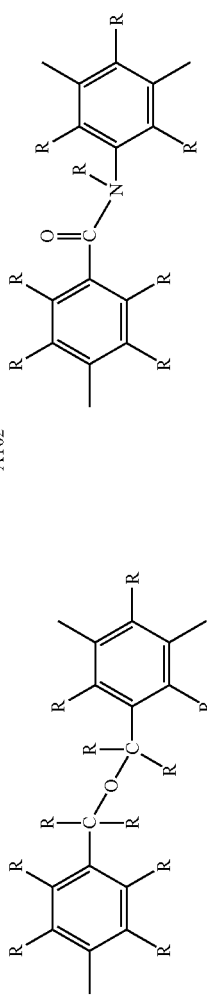
A102
A103
A104
A105

-continued
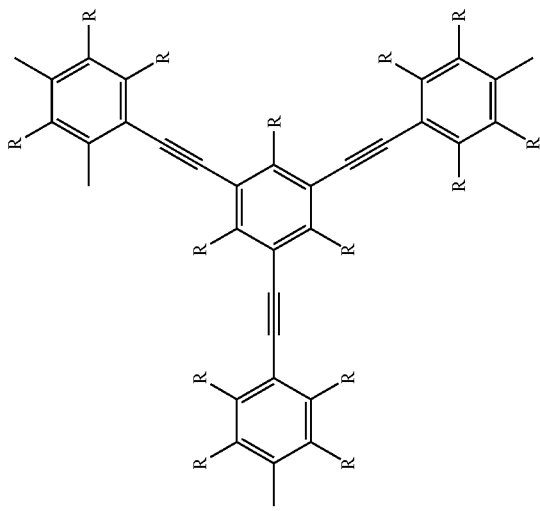
A107
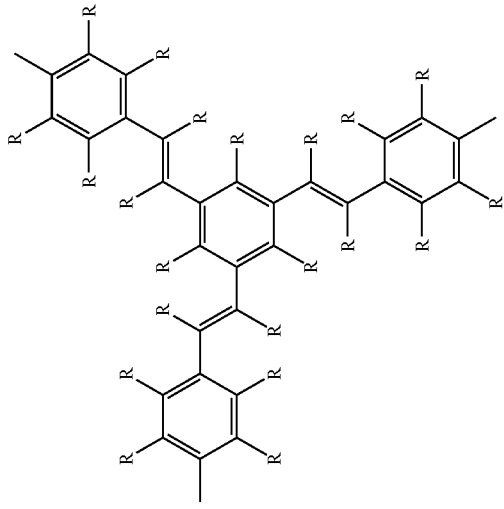
A106
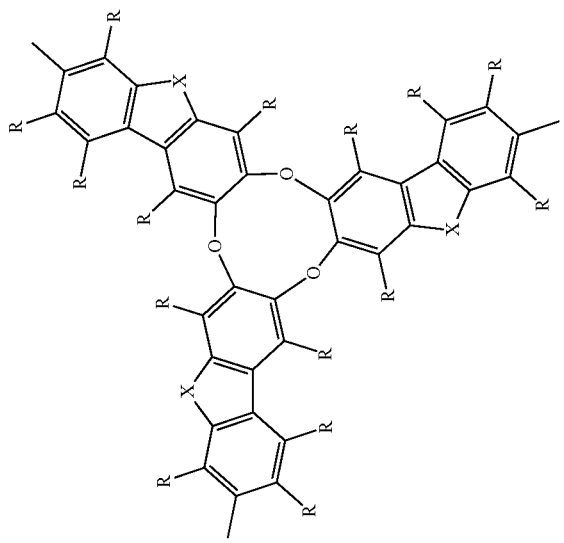
A109
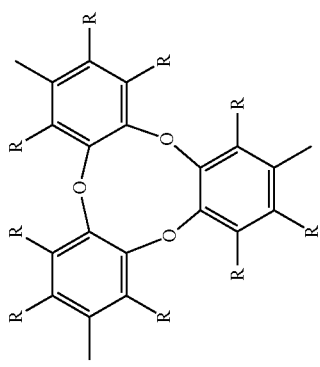
A108

A110
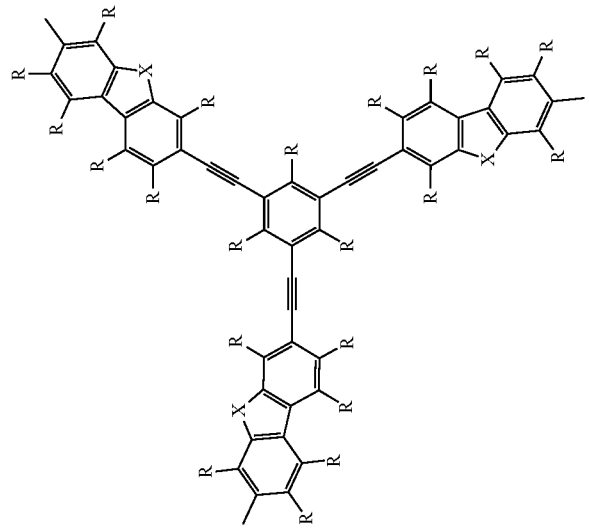
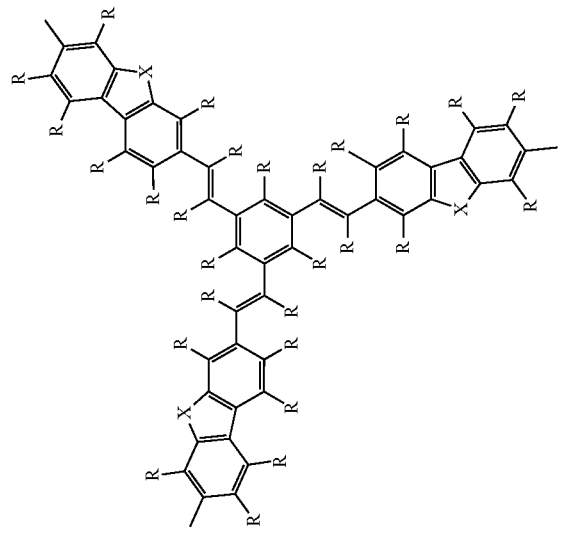

-continued
A112
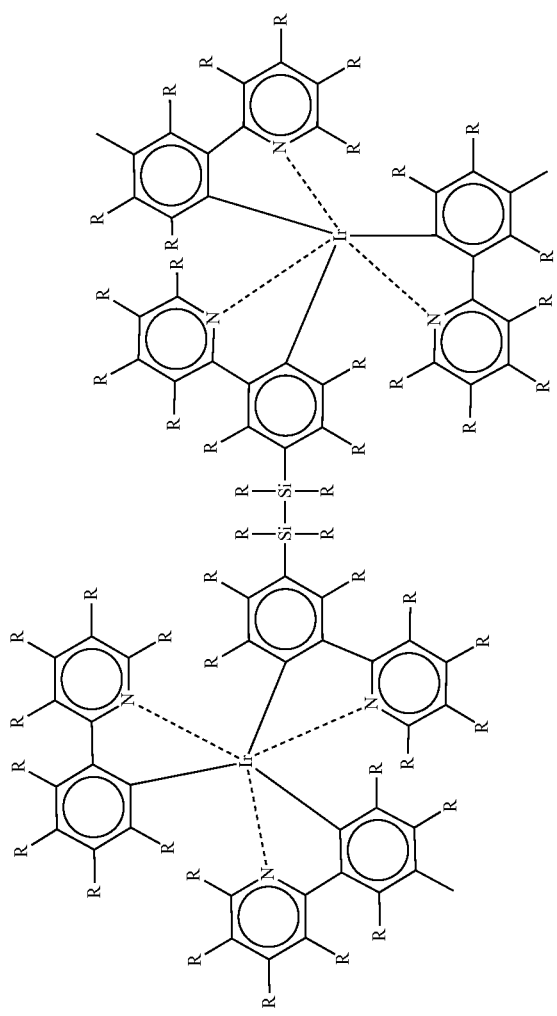
A113
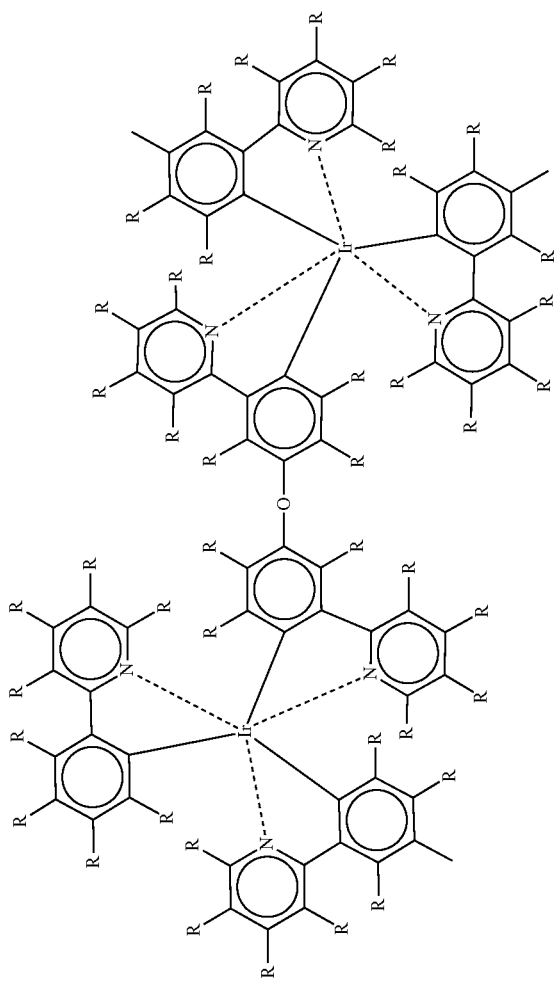

A114
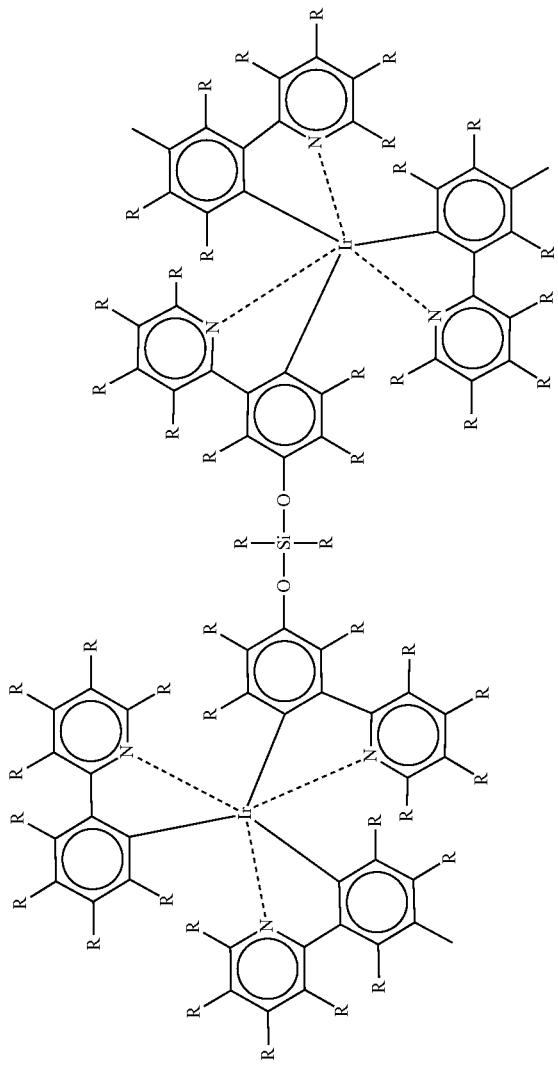
A115
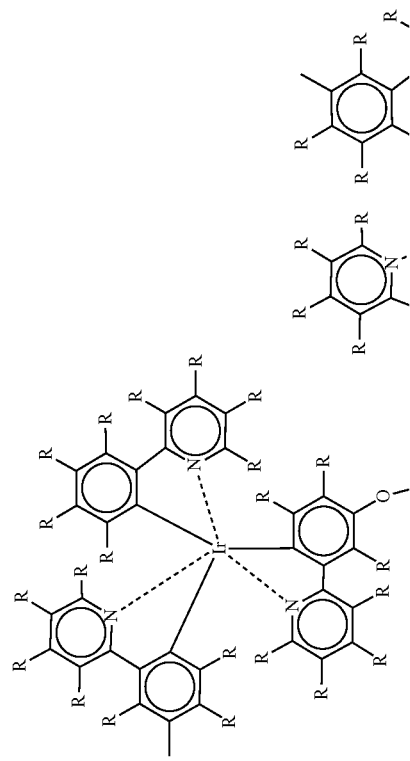

-continued
A116
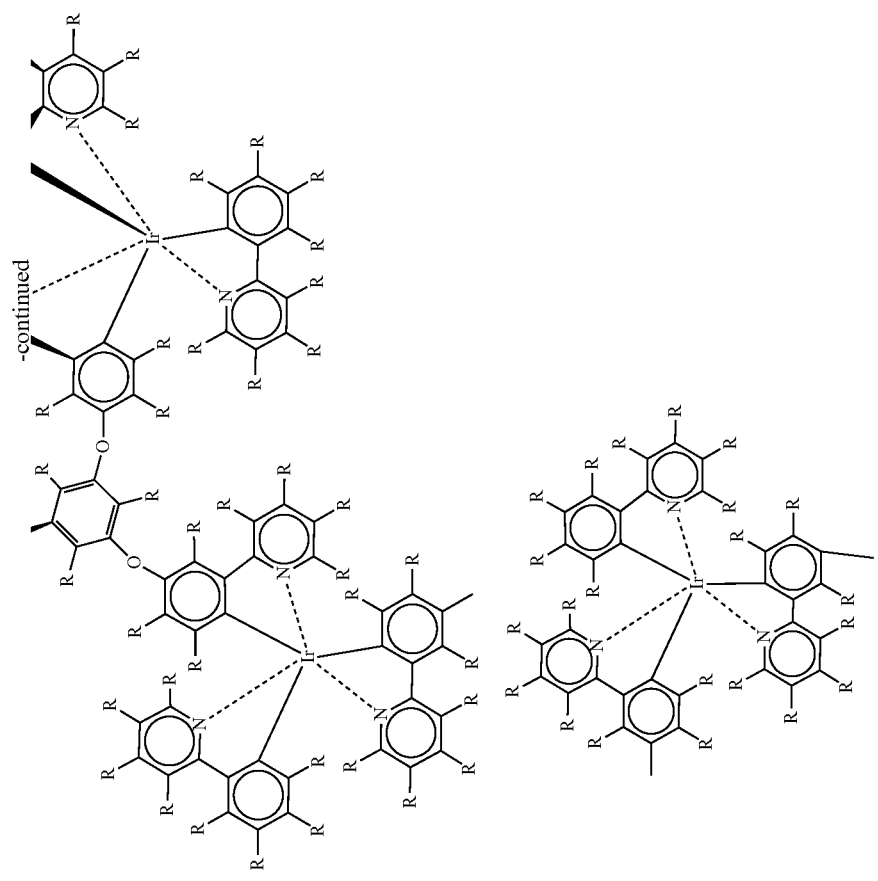

-continued
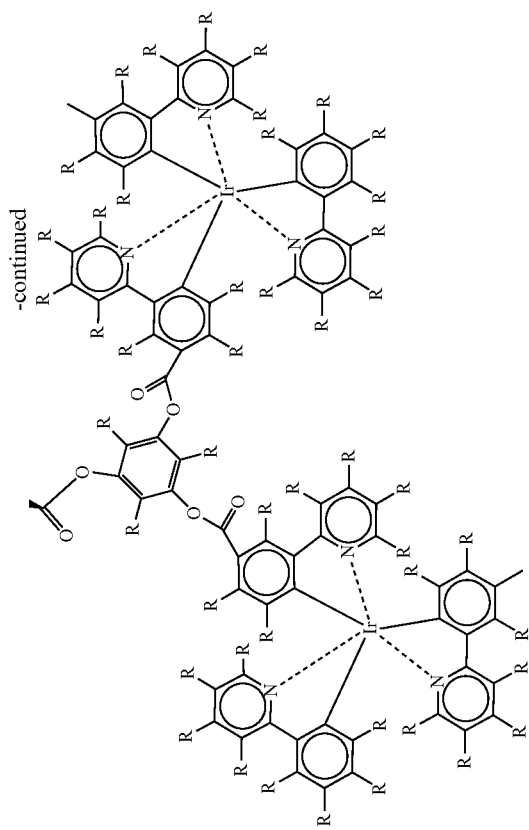

R in the examples represented by the above formulas A1 to A116 is defined in the same manner as above. X is also defined in the same manner as that in the above formula (5).

For the following group in formula (1-4),

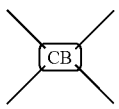

and the following group in formula (4),

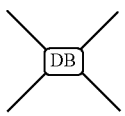

specific examples include the below tetravalent aromatic hydrocarbon cyclic groups.

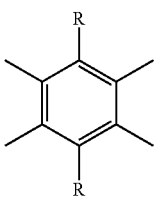
B1

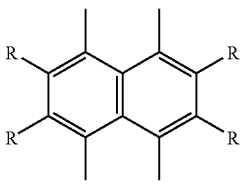
B2

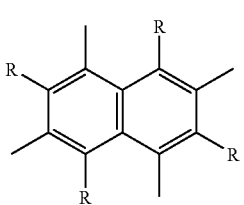
B3

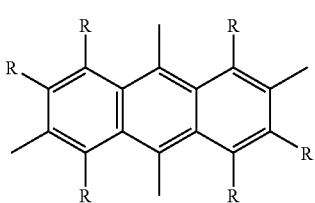
B4

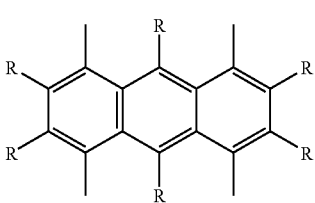
B5

-continued

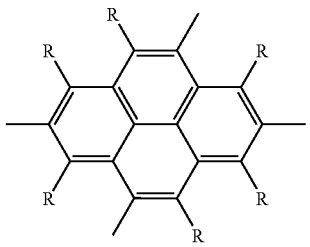
B10

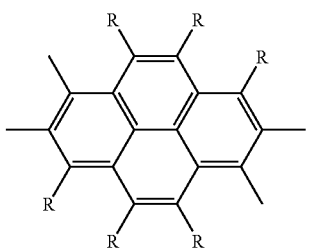
B11

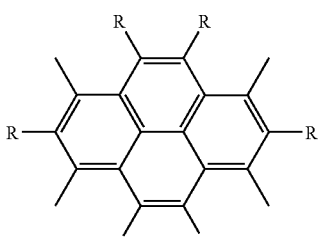
B12

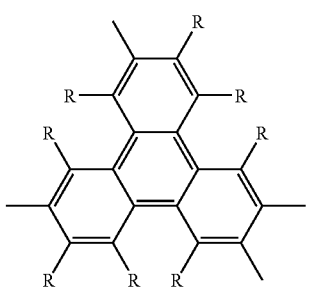
B13

Further examples include the below tetravalent heteroaromatic cyclic groups.

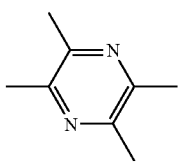
B14

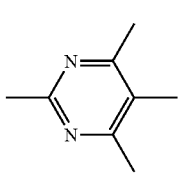
B15

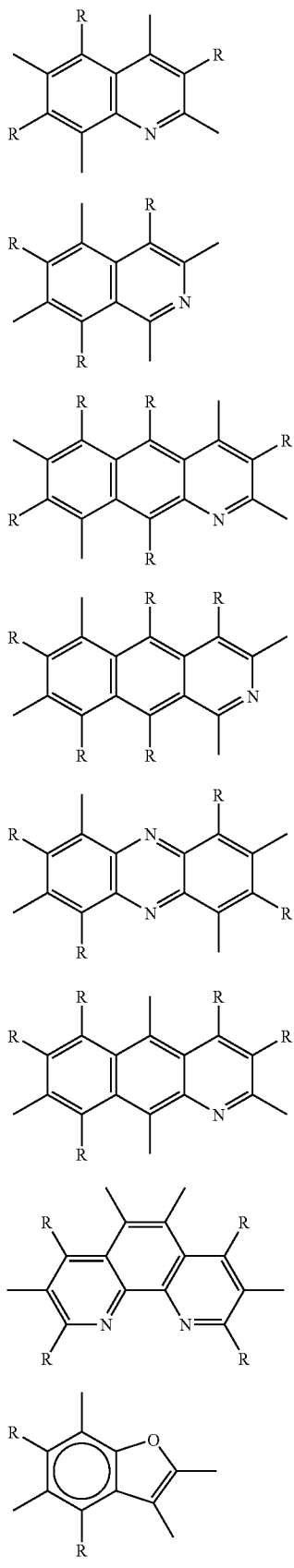
Further examples include the following groups having a tetravalent metal complex structure.
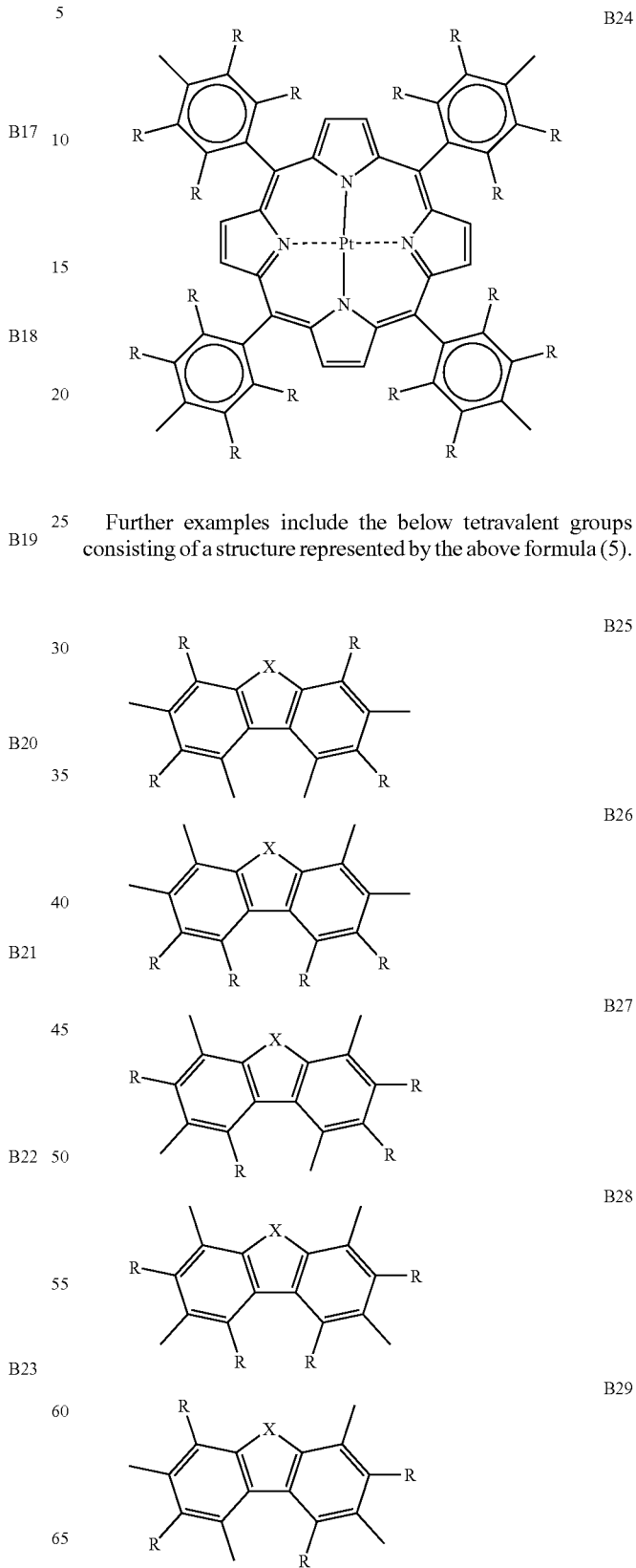
Further examples include the below tetravalent groups consisting of a structure represented by the above formula (5).

B30 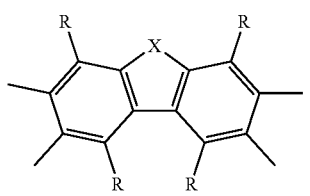
B31 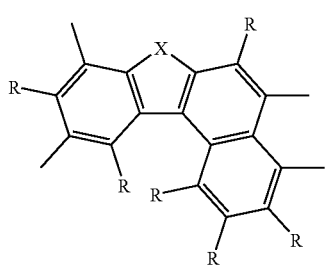
B32 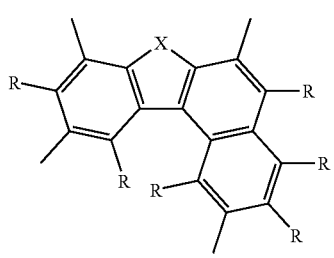
B33 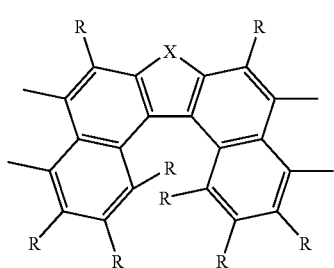
B34 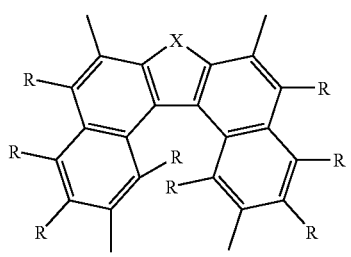
B35 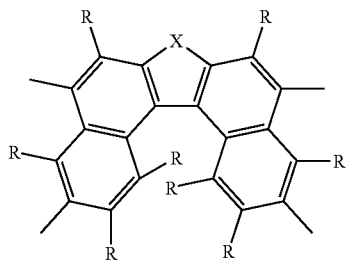
B36 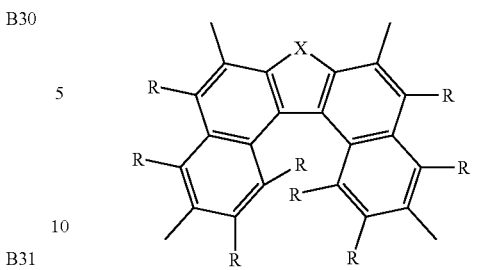
B37 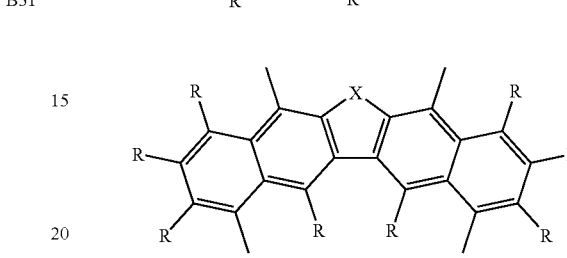
B38 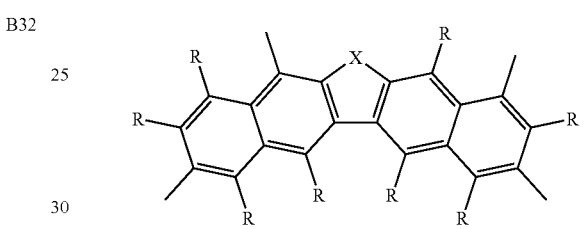
B39 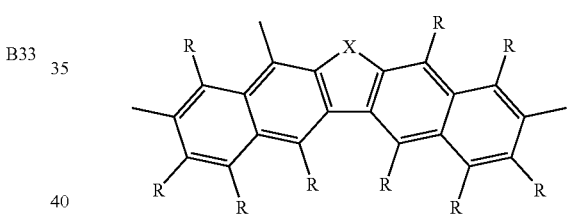
B40 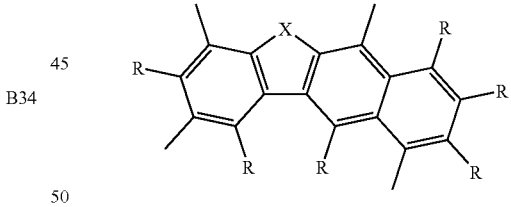
B41 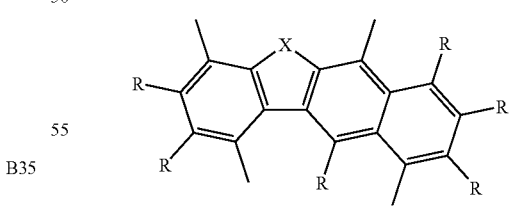
B42 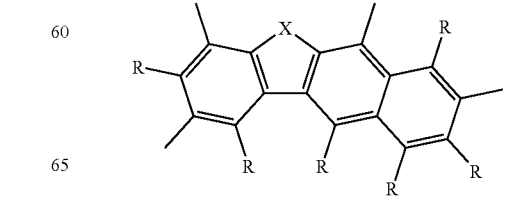

B43
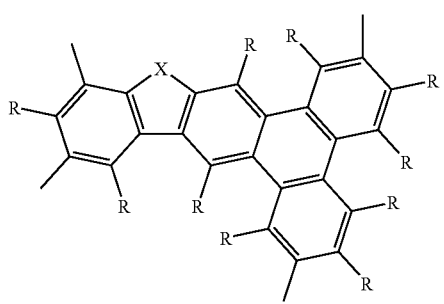
B44
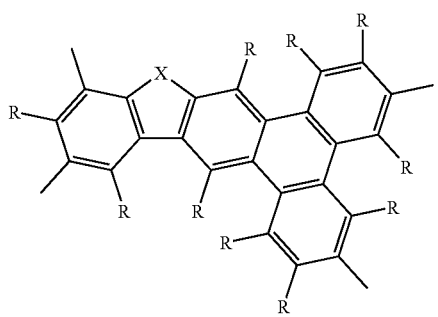
B45
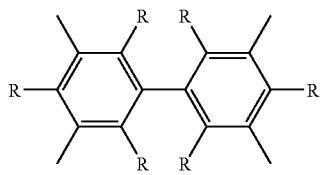
For the following group in formula (1-4),
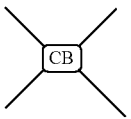
and the following group in formula (4),
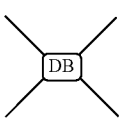
examples include the below quartervalent groups in which 2 or more of the same or different structures selected from an aromatic ring, metal complex structure and the structures represented by above formula (5) are connected together.
B46
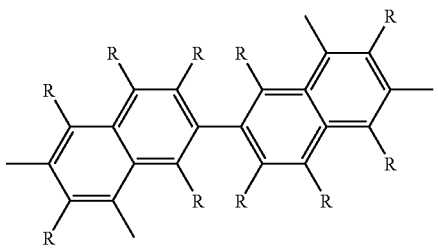
B47
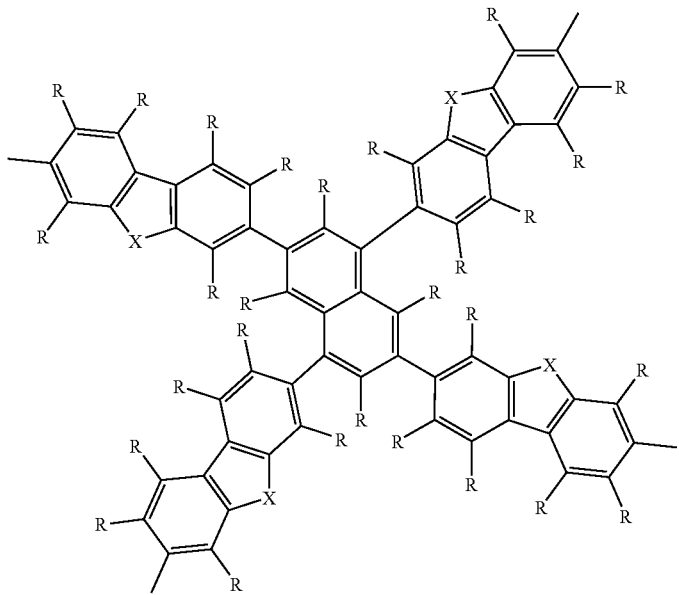

-continued
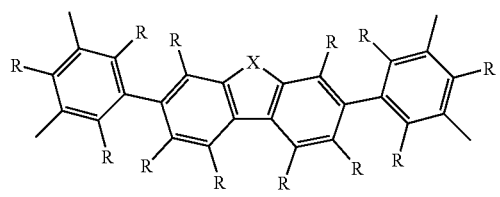
B48
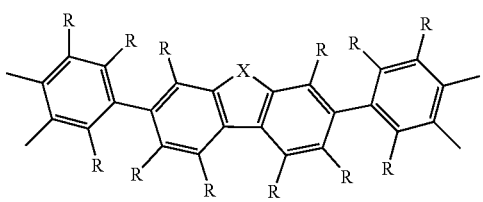
B49
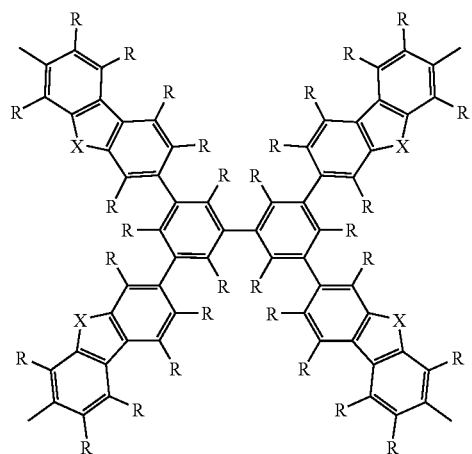
B50
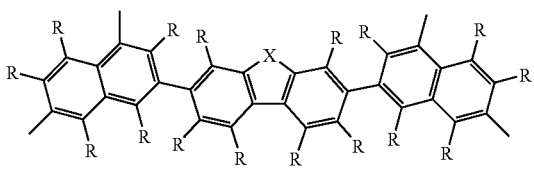
B51
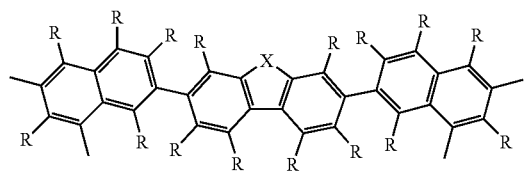
B52
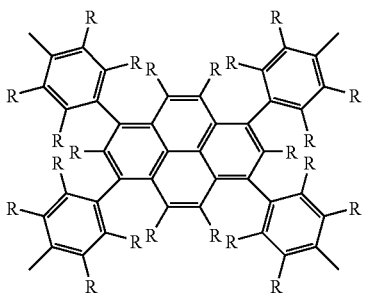
B53
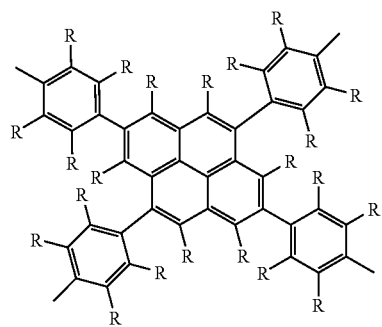
B54
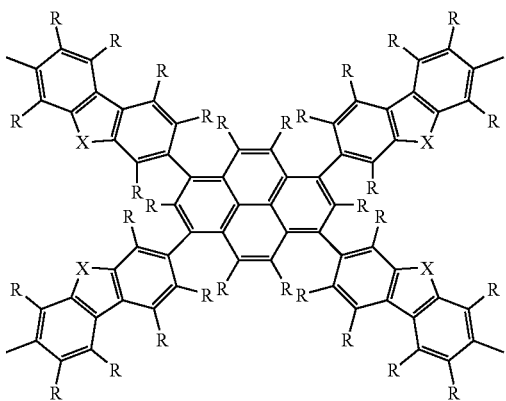
B55

-continued
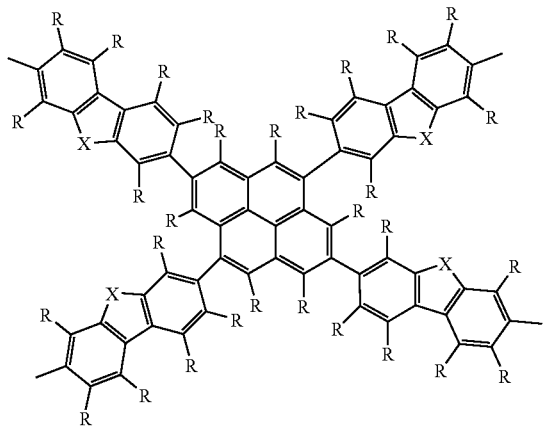
B56
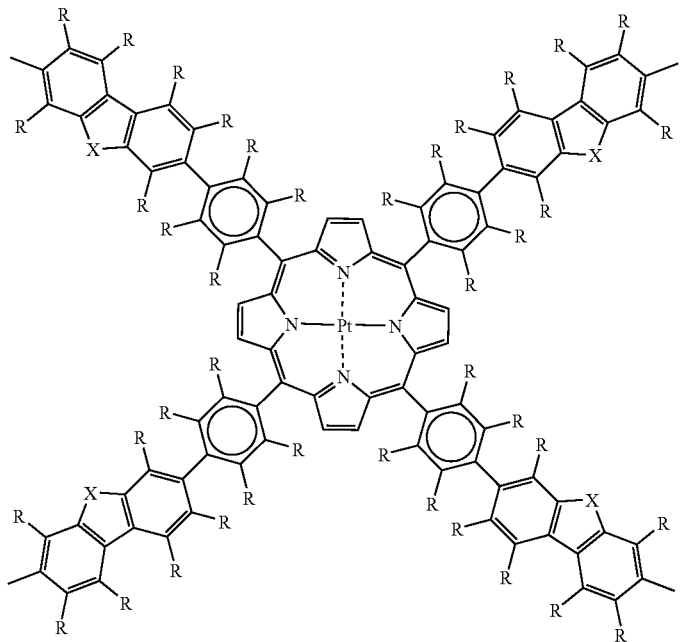
B60
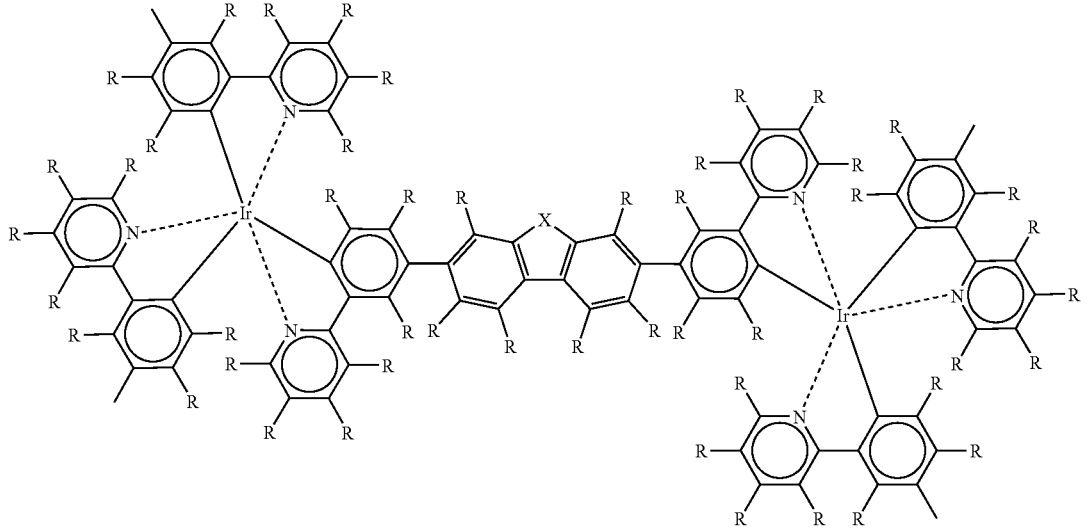
B61

B62
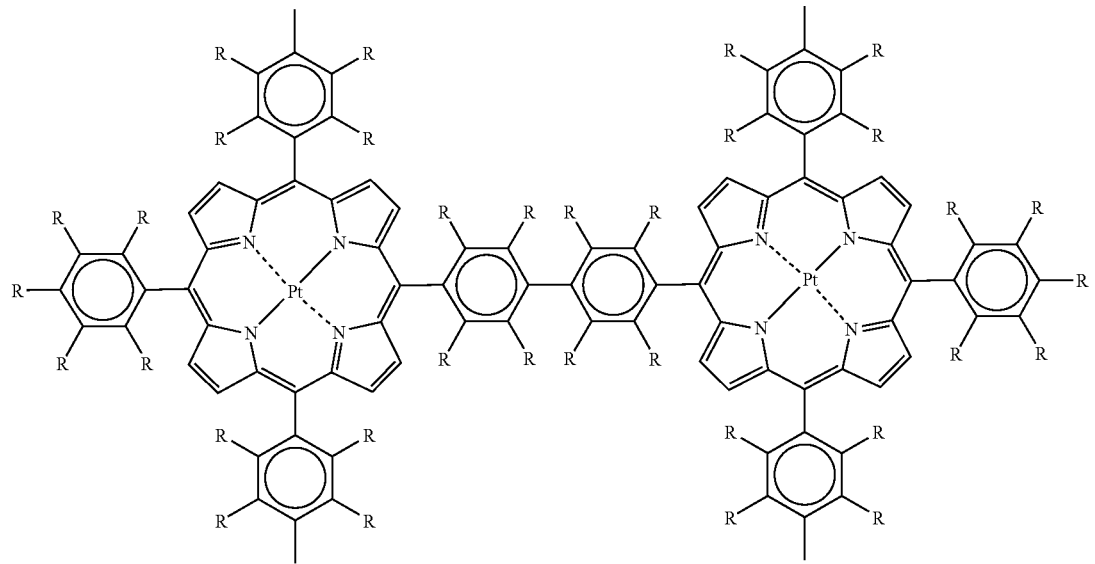
B63
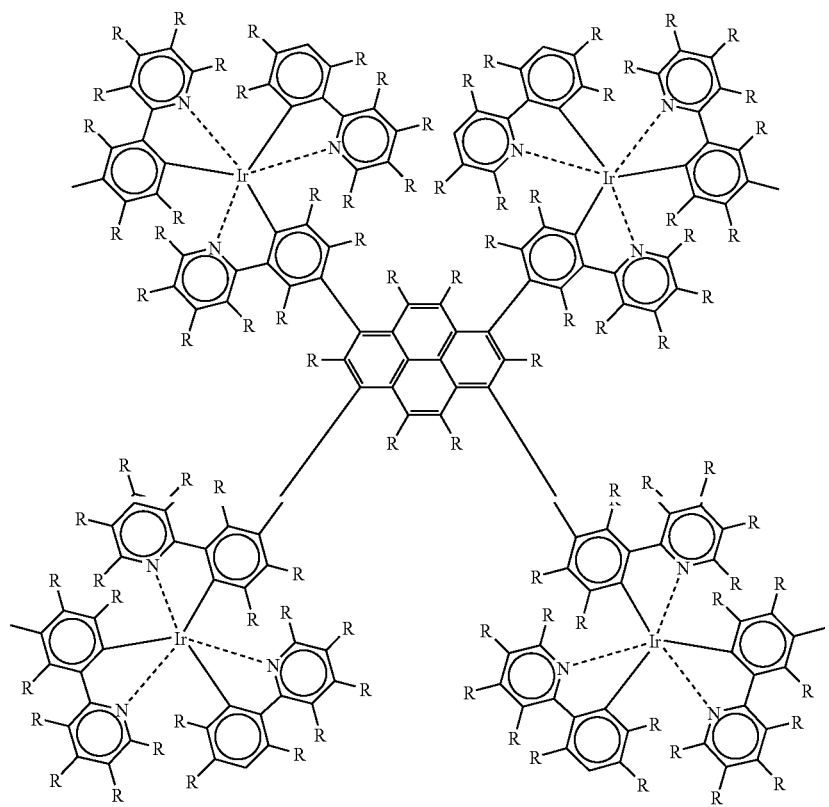

B64
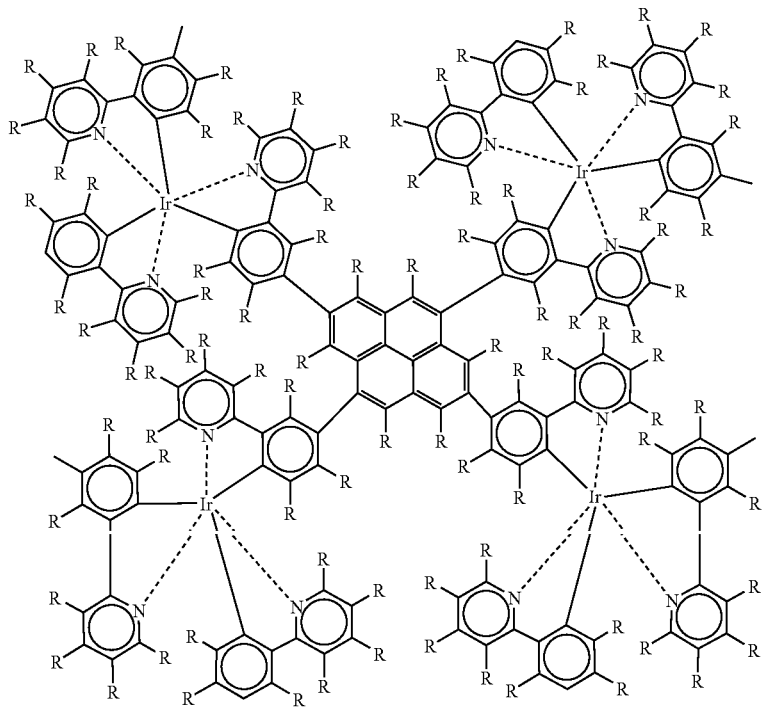
For the following group in formula (1-4),
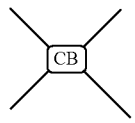
examples include the below quartervalent groups in which 2 or more of the same or different structures selected from an aromatic ring, metal complex structure and the structures represented by above formula (5) are connected together by a divalent group represented by the above (L-1).
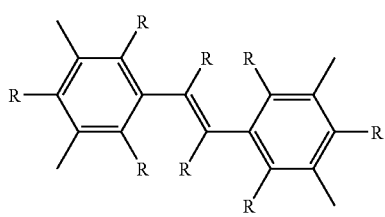
B65
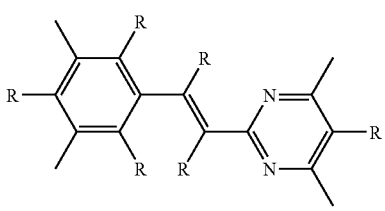
B66
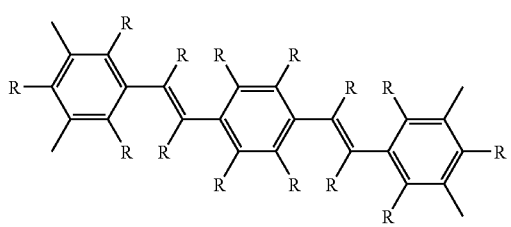
B67
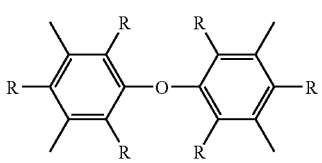
B68

-continued
B69
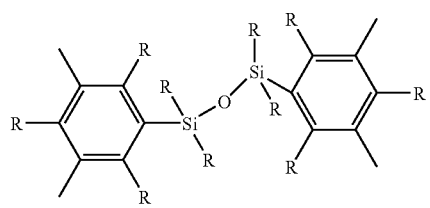
B70
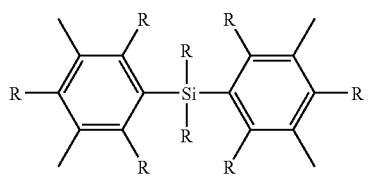
B71
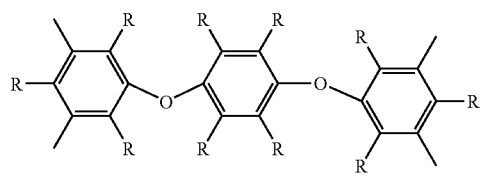
B72
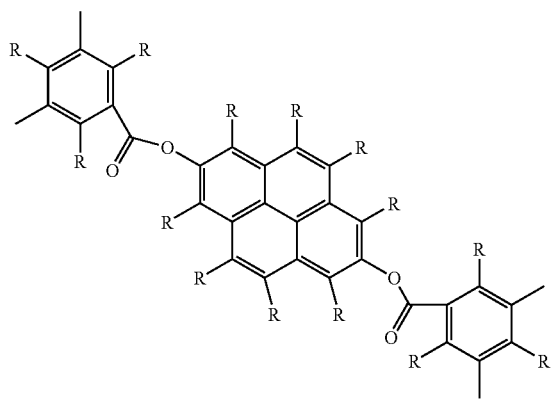
B73
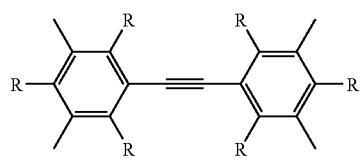
B74
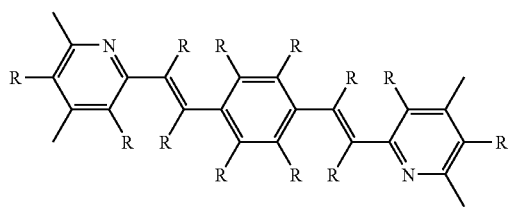
B75
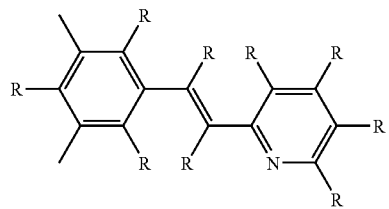
B76
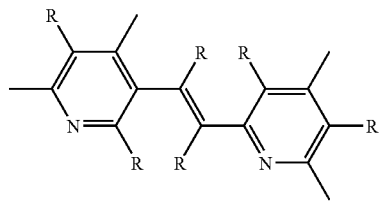
B77
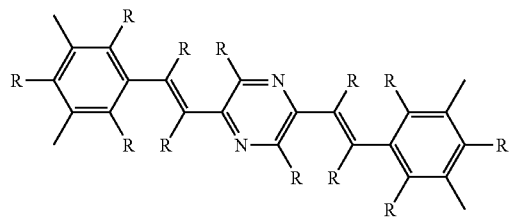
B78
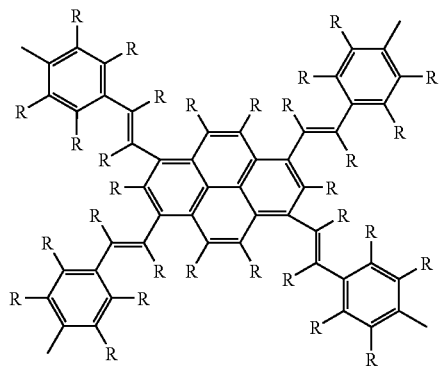

-continued
B79
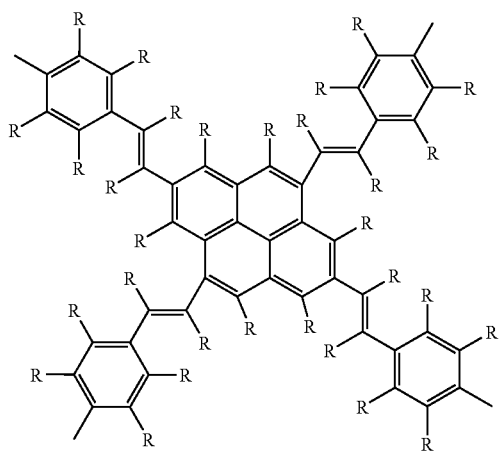
B80
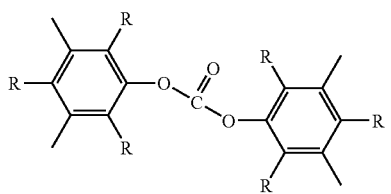
B81
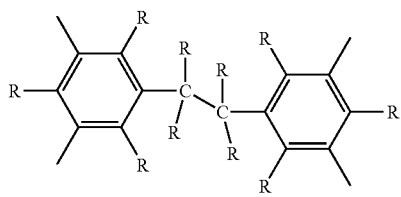
B82
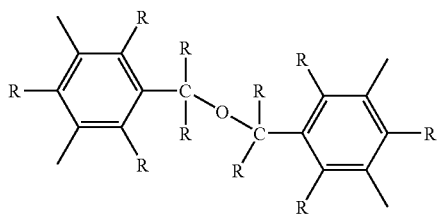
B83
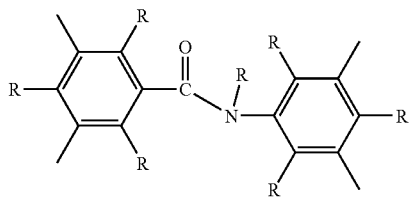
B84
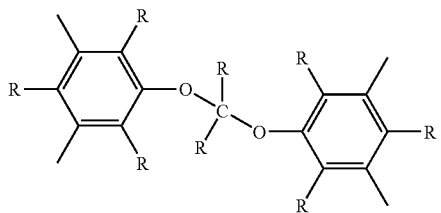
B85
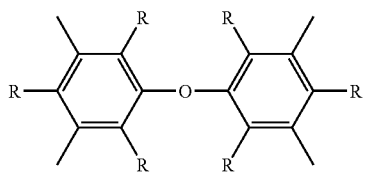
B86
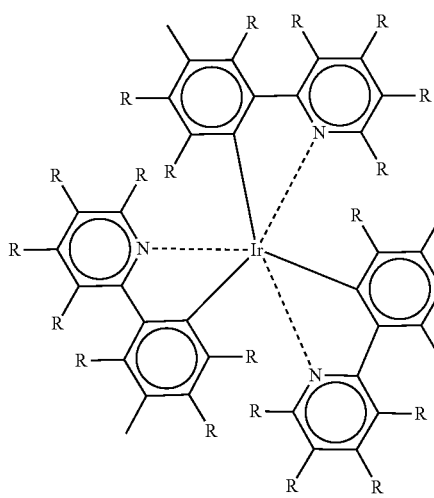
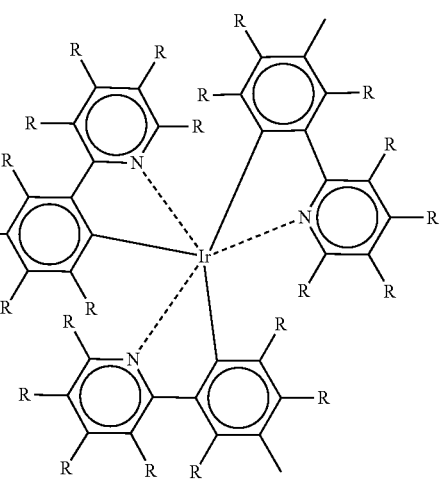

-continued
B87
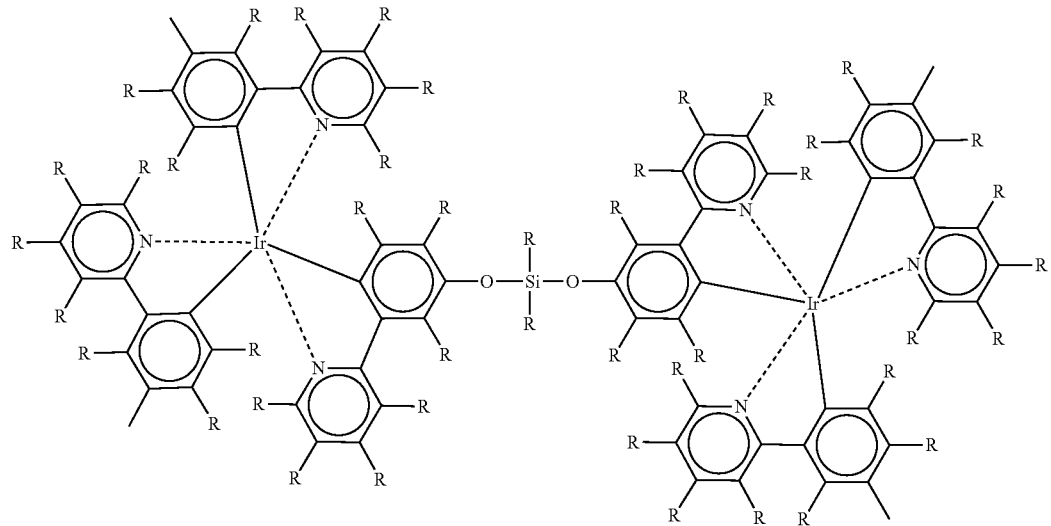
B88
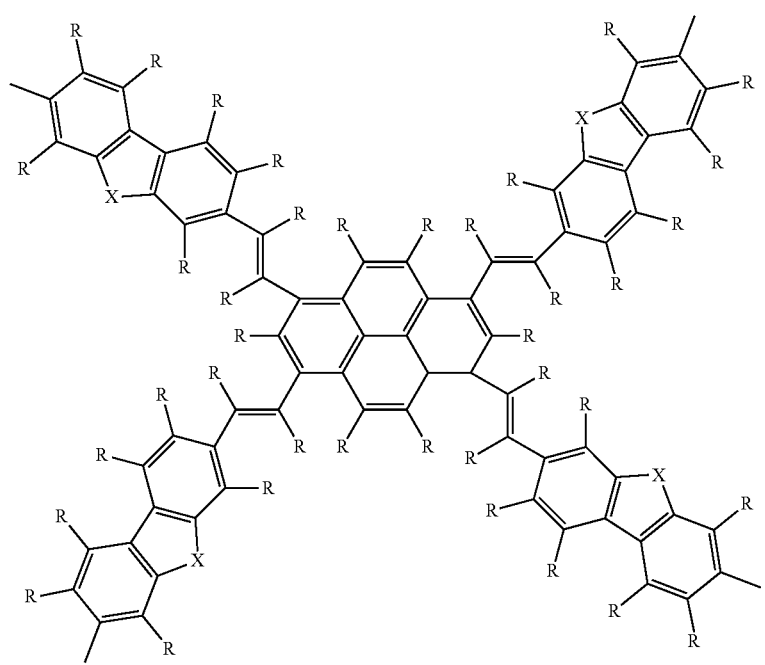

-continued

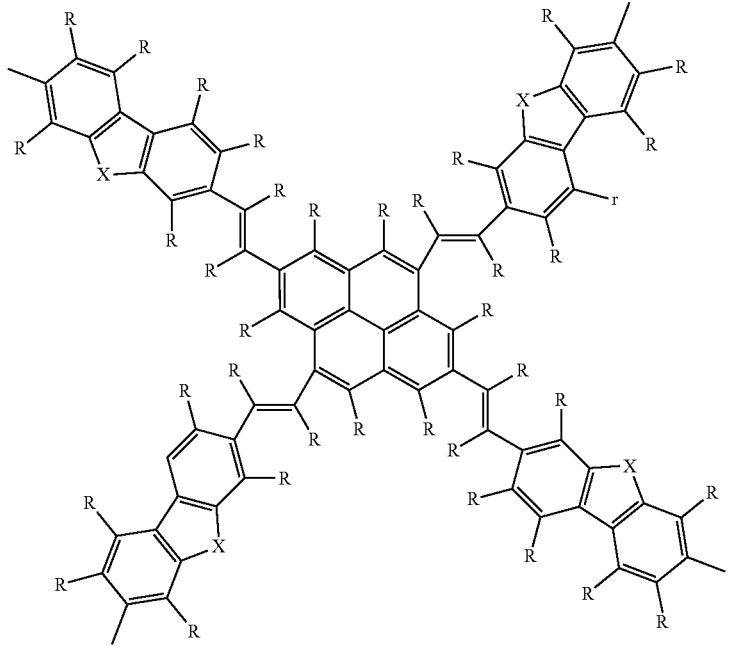

B89

R in the examples represented by the above formulas B1 to B89 is defined in the same manner as above. X is also defined in the same manner as that in the above formula (5).

If unit CA, unit CB unit CC or unit CD, unit DA, or unit DB have an aromatic ring, a benzene ring, naphthalene ring, anthracene ring, pyridine ring, triazine ring, quinoline ring, and isoquinoline ring are preferred as the aromatic ring. Such an aromatic ring preferably has one or more substituent groups. The number of aromatic rings is preferably between 1 and 10 for each unit.

If unit CA, unit CB unit CC or unit CD, unit DA or unit DB have a metal complex structure, the number of metal complex structures is preferably between 1 and 6 for each unit, and more preferably between 1 and 4.

Having the structure represented by the above formula (5) is an essential component of the dendrimer compound of the present invention. That is, at least one of the core units (unit CA, and unit CB unit CC or unit CD) and the unit in the dendritic structure (unit DA and/or unit DB) has a structure represented by the above formula (5).

If the following group in formula (1-3),

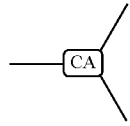

and the following group in formula (3),

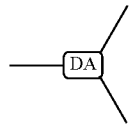

have a structure represented by the above formula (5), trivalent groups such as those represented below are preferable.

(7-1)

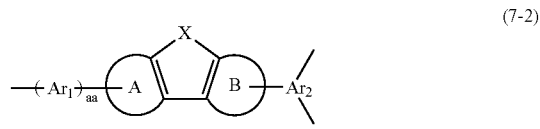

(7-2)

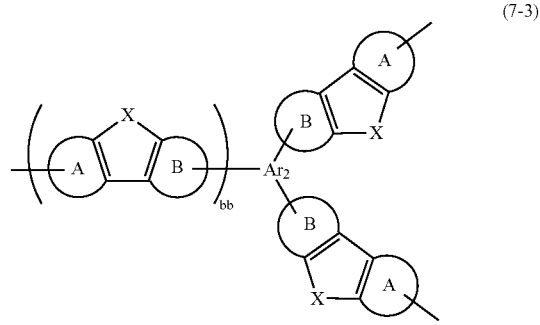

(7-3)

If the following group in formula (2),

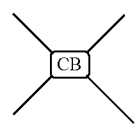

and the following group in formula (4),

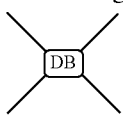

have a structure represented by the above formula (5), tetravalent groups such as those represented below are preferable.

(8-1)

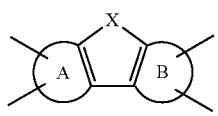

(8-2)

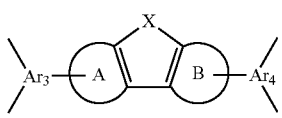

(8-3)

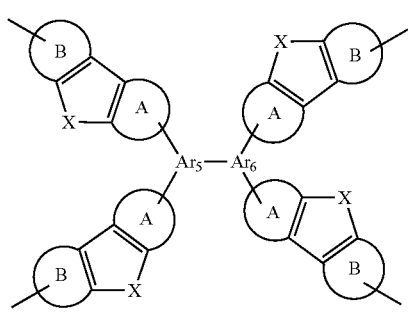

(8-4)

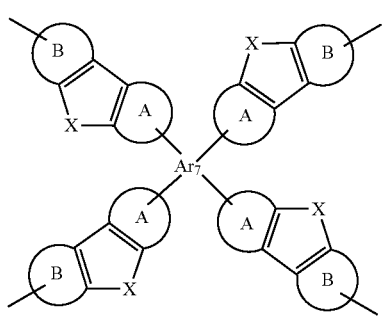

The ring A, ring B and X in the above formulas are as defined above. $Ar_1$ represents a divalent group having a divalent aromatic ring or metal complex. $Ar_2$, $Ar_3$, $Ar_4$, $Ar_5$, and $Ar_6$ represent a trivalent group each independently having a trivalent aromatic ring or metal complex. $Ar_7$ represents a tetravalent group having a tetravalent aromatic ring or metal complex. "aa" and "bb" each independently represent 0 or 1.

The term "divalent aromatic ring" refers to arylene groups and divalent heterocyclic groups.

Here, an arylene group is an atomic group in which two hydrogen atoms are removed from an aromatic hydrocarbon. The arylene group can also include structures having a benzene ring or a condensed ring, and those including two or more independent benzene rings or condensed rings bonded directly or through a group such as a vinylene group or the like. A "divalent heterocyclic group" is an atomic group in which two hydrogen atoms are removed from a heterocyclic compound. The number of carbon atoms constituting the ring is usually about 3 to 60. A "divalent group having a metal complex structure" is the remaining divalent group in which two hydrogen atoms are removed from the organic ligand of an organic ligand-containing metal complex.

Specific examples of the trivalent aromatic group, trivalent group having a metal complex, tetravalent aromatic group and the tetravalent group having a metal complex are as described above.

Preferable examples of the ring A and ring B include aromatic hydrocarbon rings, and a benzene ring, naphthalene ring or anthracene ring are even more preferable. The ring A and ring B also preferably have a substituent group.

A non-hydrogen group is connected to an end of the mono to tetravalent bonding group. Usually a linking group, dendritic structure, or below-described surface group are connected.

Preferable examples of X include —O—, —S—, —S(=O)—, —SO$_2$—, —P(R$_4$)—, and —PR$_5$(=O)—; and more preferable are —O— and —S—. Here, $R_4$ and $R_5$ are as defined above.

Preferable examples of the above-described formula (6-1), formula (6-2) and formula (6-3) include the above-described A45 to A67, A79 to A85 and the like.

Preferable examples of the above-described formula (7-1), formula (7-2), formula (7-3) and formula (7-4) include the above-described B25 to B44, B47 to B52, B55, B56, B60, B61 and the like.

The dendrimer compound of the present invention preferably has a metal complex structure. That is, at least one of the core unit (unit CA, unit CB unit CC or unit CD) and the unit in the dendritic structure (unit DA and/or unit DB) has a metal complex structure.

From the perspective of improving luminescence quantum efficiency, the core unit (unit CA, unit CB unit CC or unit CD) preferably has a metal complex structure.

Preferable examples when the following group in formula (1),

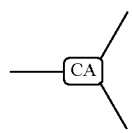

has a metal complex structure include the above-described A38 to A44, A86 to A89, A112 to A116 and the like.

Preferable examples when the following group in formula (2),

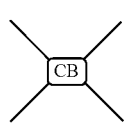

has metal complex structure include the above-described B24, B57 to B64, B86 to B89 and the like. "L" in formula (1), formula (2), formula (3) and formula (4) is a direct bond or a linking group selected from the above-described (L-2). Preferred is a direct bond or a linking group selected from the divalent group represented by the below (L-2'). Even more preferred is a direct bond.

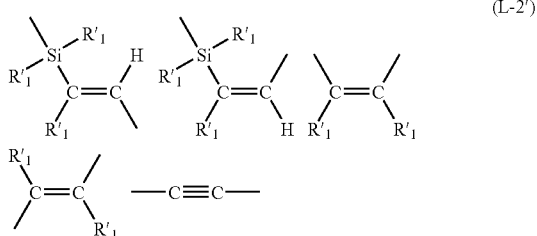

(L-2')

Here, $R_1'$ is defined in the same manner as above.

The dendrimer compound of the present invention has a chemical structure formed by three-dimensionally repeating at least one dendritic structure represented by the formula (3) or (4) from a central core represented by the formula (1) or (2). Examples of its terminal structure (hereinafter sometimes referred to as surface structures) include a hydrogen atom, or a group which forms the linking group described in the above L-2 from a condensation reaction or an addition reaction. Specific examples include a halogen atom, alkyl sulfonate group, aryl sulfonate group, arylalkyl sulfonate group, boric acid group, borate ester group, sulfonium methyl group, phosphonium methyl group, phosphonate methyl group, monohalogenated methyl group, formyl group, or the groups represented by the below (L-3).

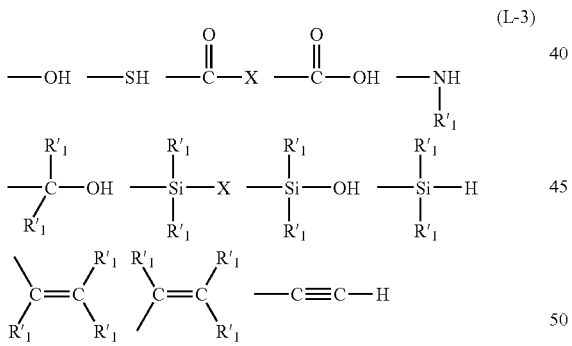

(L-3)

Alternatively, examples for the terminal structure include groups represented by the above (L-3) which have further undergone a condensation reaction or an addition reaction. In this case, the residue obtained by removing, from a newly formed linking group, the linking group to its terminal is called a surface group.

The terminal structure of the dendrimer compound of the present invention preferably has such a surface group. Specific examples of such a surface group include an alkyl group, aryl group, alkoxy group, alkylthio group, aryloxy group, arylthio group, amino group, silyl group, substituted silyl group, monovalent hetreocyclic group, monovalent group having a metal complex structure, and a monovalent group having the structure represented by formula (5).

Examples of the monovalent group having a metal complex structure include those given below.

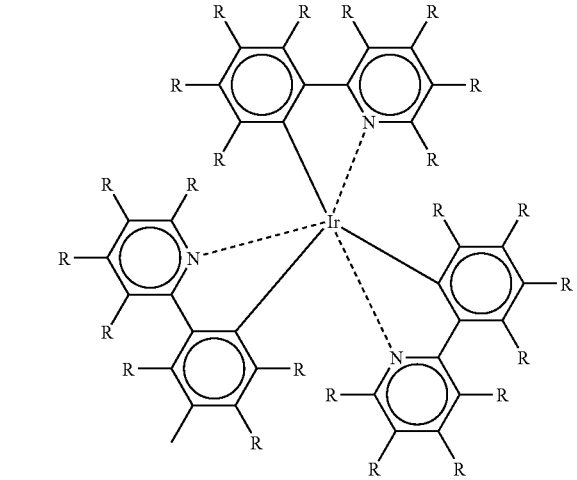

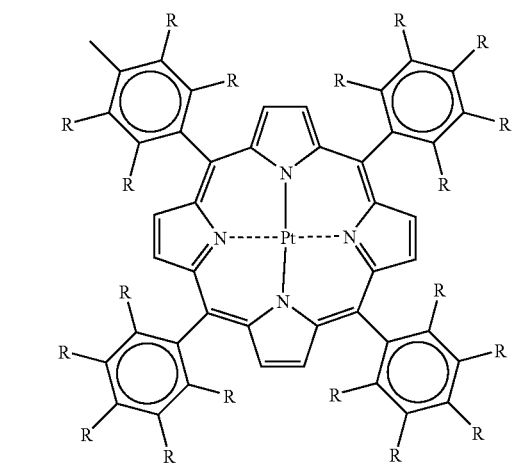

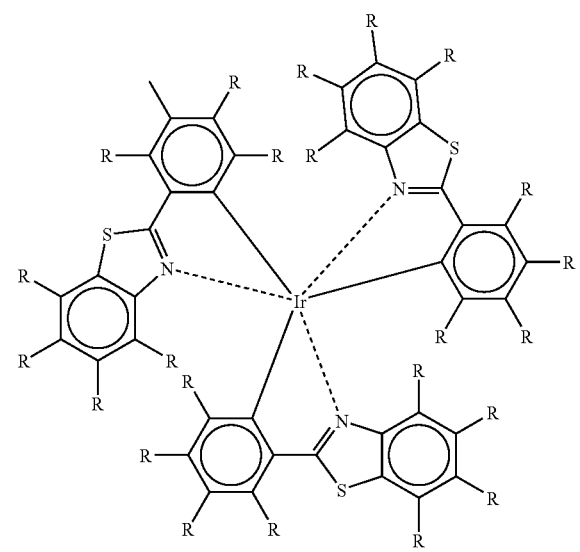

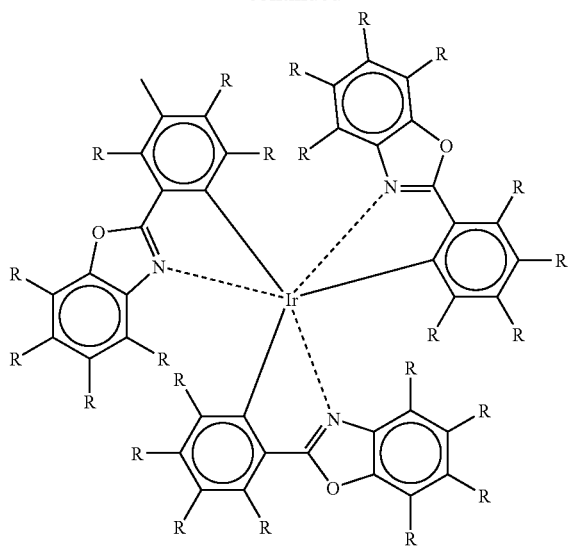
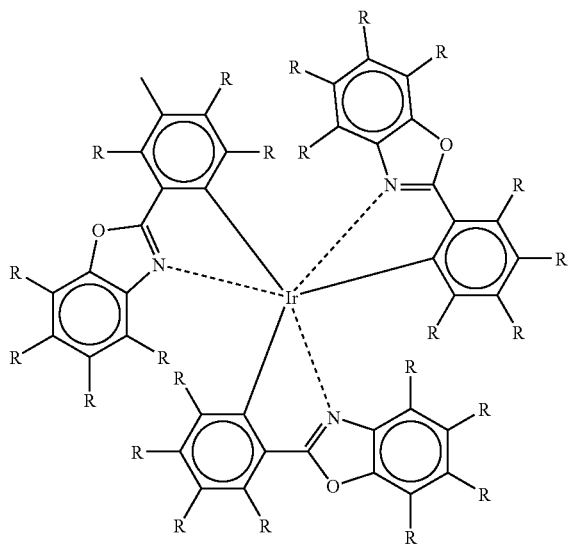
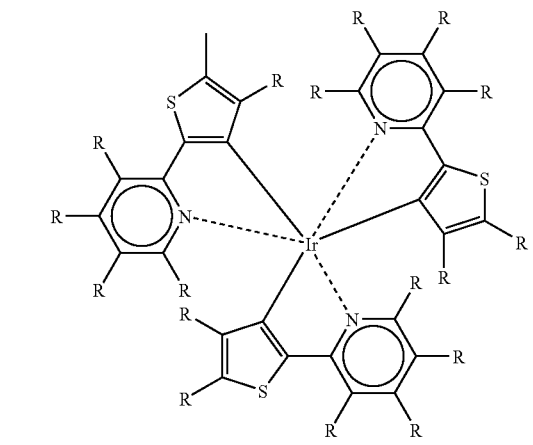
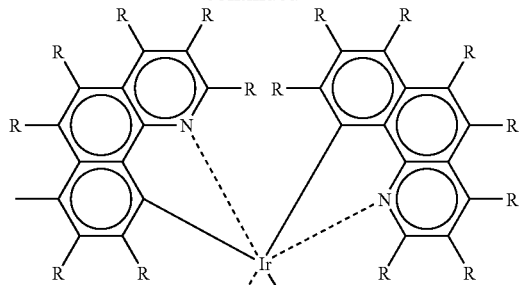
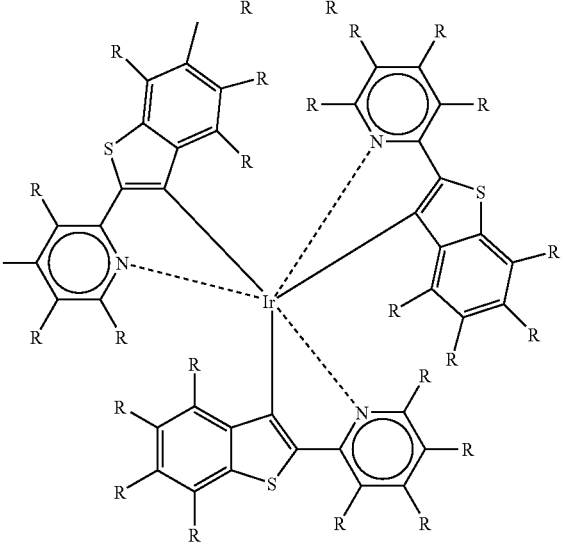
Examples of the monovalent group having a structure represented by formula (5) include the following.
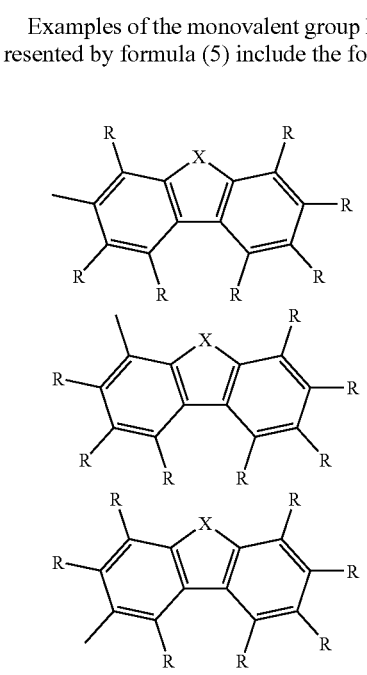

-continued

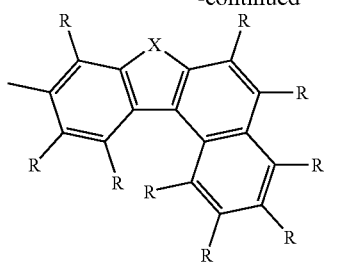
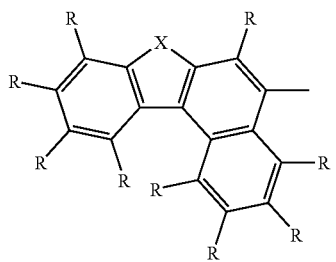
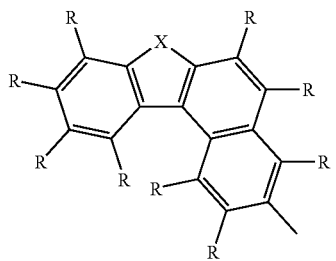
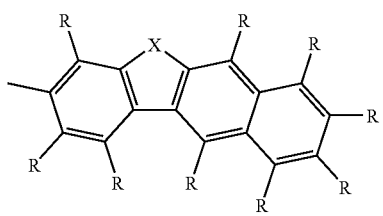
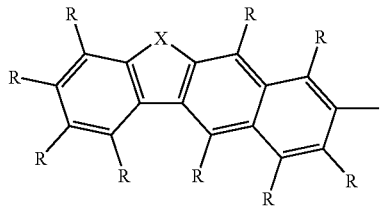
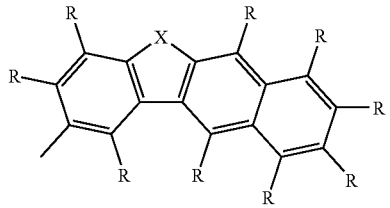
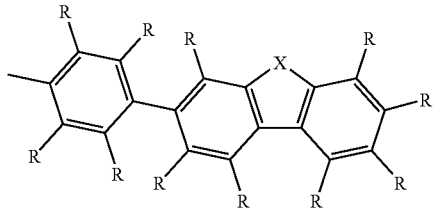

-continued

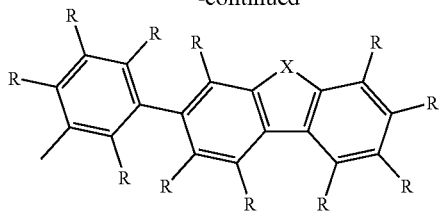
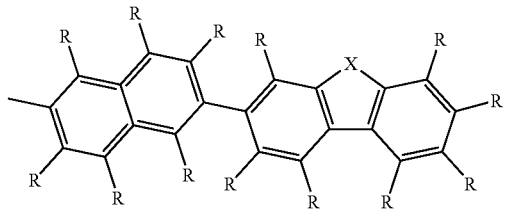

In the above formula, R and X are defined in the same manner as above.

Next, a method for producing the dendrimer compound of the present invention will be explained.

Methods for producing the dendrimer can broadly be classified into two types. The first method is a method wherein a dendritic structure comprising repeating units is repeated in three-dimensions around the core acting as the center. The second method is a method for forming a core from a condensation reaction or an addition reaction of multi-branched compounds, which comprise a partial structure that forms a core from the condensation reaction or addition reaction, and dendrons, specifically, a chemical structure obtained by three-dimensionally repeating a dendritic structure which comprises branched units.

The first production method will now be described in detail. A first generation dendrimer compound can be produced from the condensation reaction or addition reaction of a compound represented by the following formulas (8-1), (9-1), (8) or (9) with at least a compound selected from the compounds represented by formulas (10-1) and (11-1).

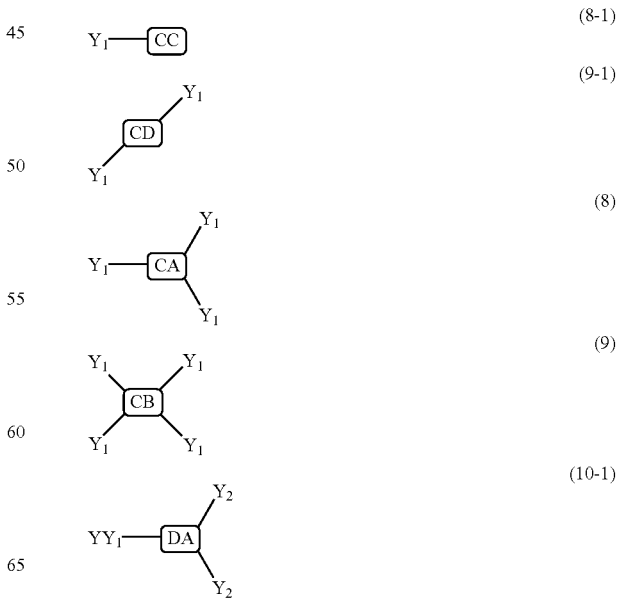

-continued

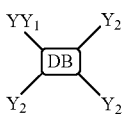
(11-1)

Here, unit CA, unit CB unit DA and unit DB are defined in the same manner as above. Further, $Y_1$, $Y_2$ and $YY_1$ each independently represent groups which participate in the condensation reaction or addition reaction, and which satisfy the following conditions.

That is, with the combination of $Y_1$ and $YY_1$, a condensation reaction or addition reaction occurs to form the above-described L. However, a condensation reaction or addition reaction does not occur with the combination of $Y_1$ and $Y_2$.

Specific examples of $Y_1$, $Y_2$ and $YY_1$ include a halogen atom, alkyl sulfonate group, aryl sulfonate group, arylalkyl sulfonate group, boric acid group, borate ester group, sulfonium methyl group, phosphonium methyl group, phosphonate methyl group, formyl group, or the groups represented by the below (L-3).

Here, examples of the alkyl sulfonate group include a methanesulfonate group, ethanesulfonate group, trifluoromethanesulfonate group and the like. Examples of the aryl sulfonate group include a benzenesulfonate group, p-toluenesulfonate group and the like. Examples of the arylalkyl sulfonate group include a benzyl sulfonate group and the like.

Examples of the borate ester group include the groups represented by the following formula.

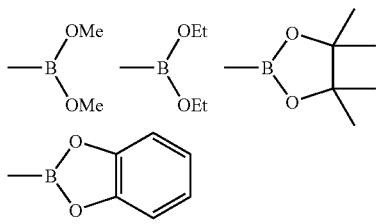

In the formula, Me represents a methyl group and Et represents an ethyl group.

Examples of the sulfonium methyl group include the groups represented by the following formulas.

—$CH_2S^+Me_2X^-$, —$CH_2S^+Ph_2X^-$ (wherein X represents a halogen atom, and Ph represents a phenyl group)

Examples of the phosphonium methyl group include the groups represented by the following formula.

—$CH_2P^+Ph_3X^-$ (wherein X represents a halogen atom)

Examples of the phosphonate methyl group include the groups represented by the following formula.

—$CH_2PO(OR_2')_2$ (wherein X represents a halogen atom, R' represents an alkyl group, aryl group or arylalkyl group)

Following the production method of the above-described first generation dendrimer compound, a second generation dendrimer compound can be produced by subjecting one or more compounds selected from the compounds represented by the following formula (10-2) and formula (11-2) to a condensation reaction or addition reaction.

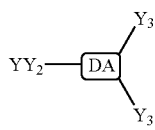
(10-2)

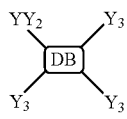
(11-2)

Here, unit DA and unit DB are defined in the same manner as above. Further, $Y_3$ and $YY_2$ each independently represent groups which participate in the condensation reaction or addition reaction, and which satisfy the following conditions. That is, with the combination of $Y_2$ and $YY_2$, or the combination of $Y_3$ and $YY_1$, a condensation reaction or addition reaction occurs to form the above-described L. However, a condensation reaction or addition reaction does not occur with the combination of $Y_2$ and $Y_3$. The specific examples of $Y_3$ and $YY_2$ are the same as those described above.

A third generation dendrimer compound can also be obtained in the same manner, by alternately subjecting in sequence one or more compounds selected from the compounds represented by the above formula (10-1) and formula (11-1) to a condensation reaction or addition reaction with one or more compounds selected from the compounds represented by the above formula (10-2) and formula (11-2).

The first method will now be schematically illustrated. The first generation dendrimer represented by the following formula (18-10) can be obtained by subjecting a compound represented by the above formula (8) and a compound represented by the above formula (10-1) to a condensation reaction or addition reaction.

(18-10)

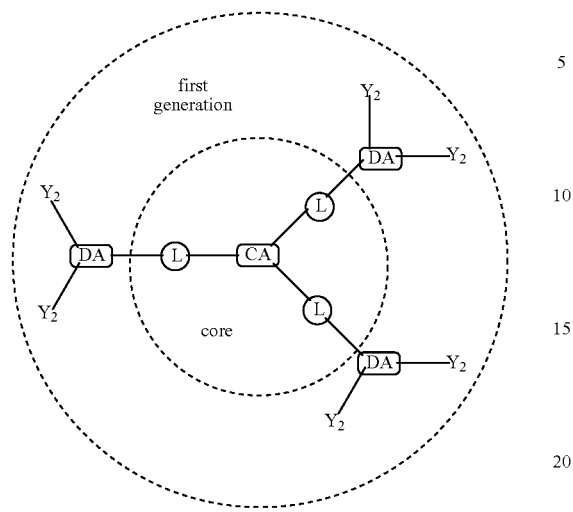

By further subjecting the compound represented by the above formula (10-2) to a condensation reaction or addition reaction, the second generation dendrimer represented by the following formula (18-11) can be obtained.

(18-11)

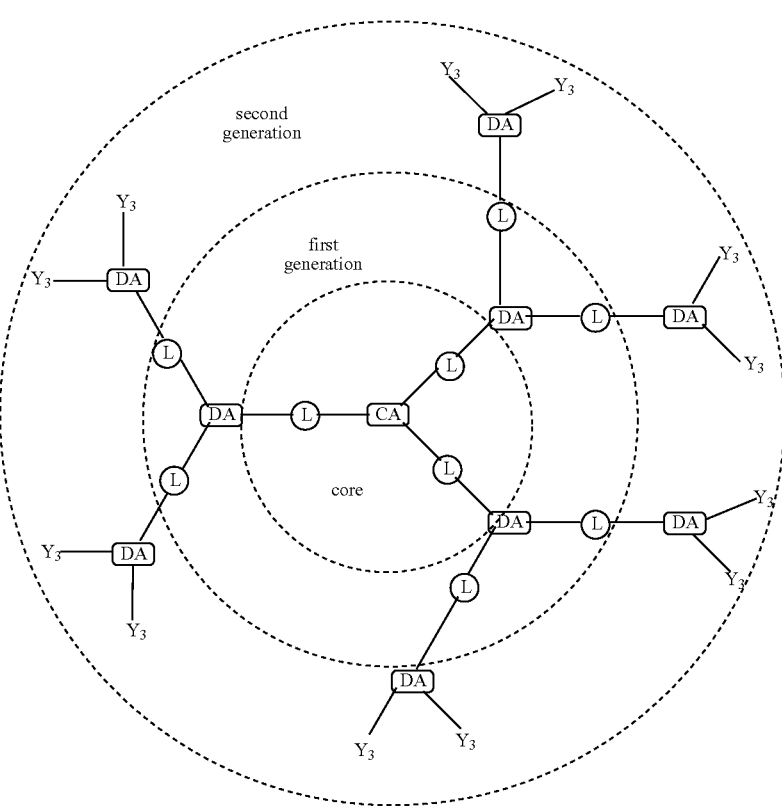

By further subjecting the compound represented by the above formula (10-1) to a condensation reaction or addition reaction, the third generation dendrimer represented by the following formula (18-12) can be obtained.

(18-12)

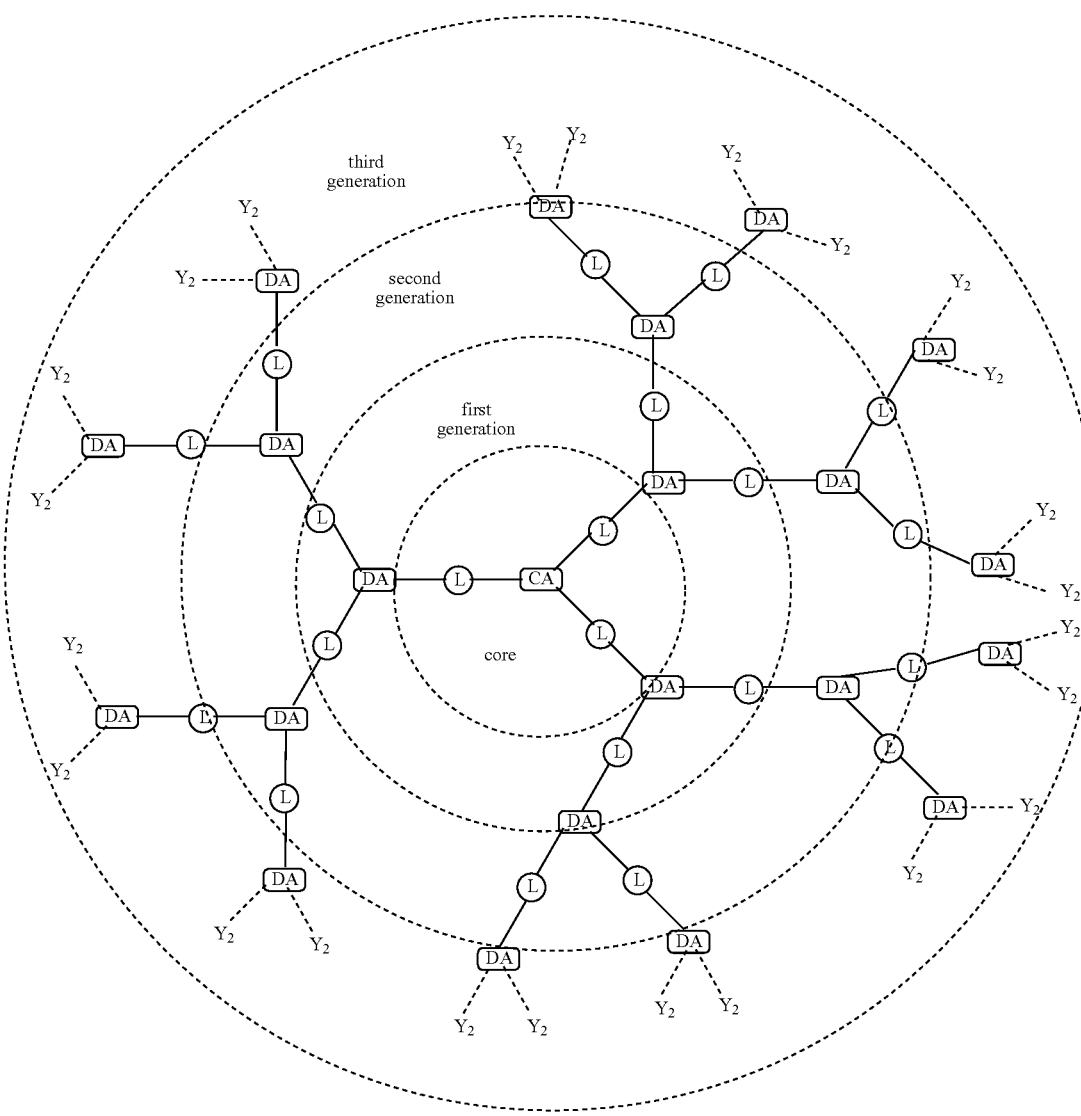

A method separate from the first method will be explained in detail below. That is, instead of the compounds represented by the above formula (8) or formula (9), a first generation dendrimer can be obtained by subjecting one or more compounds selected from the compounds represented by the above formula (10-3) and formula (11-3) to a condensation reaction or addition reaction.

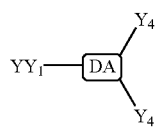
(10-3)

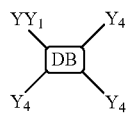
(11-3)

Here, unit DA and unit DB are defined in the same manner as above. Further, $YY_1$ is defined in the same manner as in formula (10-1). While $Y_4$ does not directly react with $YY_1$, $Y_4$ is a group which will become a precursor of the group which undergoes the condensation reaction or addition reaction with $YY_1$. Specific examples of $Y_4$ include, when $Y_1$ is a hydroxyl group, a formyl group (oxidized to a carbonyl group) as a carboxyl group precursor which can undergo a condensation reaction with $Y_1$, and a halogen atom (after reacting with a base, reacted with trimethoxyborane) as a borate ester group precursor which can undergo a condensation reaction with $Y_1$. If $Y_1$ is a formyl group, further examples include a monohalogenated methyl group as a precursor for a sulfonium methyl group, phosphonium methyl group or phosphonate methyl group, which can undergo a condensation reaction with $Y_1$.

Subsequent to the production method of the above-described first generation dendrimer compound, a second generation dendrimer compound can be obtained by converting $Y_4$ to a group for undergoing a condensation reaction or addition reaction with $YY_1$, and subjecting one or more compounds selected from the compounds represented by the above formula (10-3) and formula (11-3) to a condensation reaction or addition reaction.

In the same manner, the third and following generations can be obtained by converting to a group for undergoing a condensation reaction or addition reaction with YY₁, and subjecting one or more compounds selected from the compounds represented by the above formula (10-3) and formula (11-3) to a condensation reaction or addition reaction.

Specific examples of the second method include a method for synthesizing a dendrimer compound forming unit CA or unit CB by subjecting multi-branched compounds, which comprise a chemical structure constituted from at least one kind of dendritic structure selected from the dendritic structures represented by the following formula (12-1) or formula (12-2) and the above formula (3) and formula (4) being regularly repeated in three-dimensions, to a condensation reaction or an addition reaction.

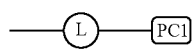
(12-1)

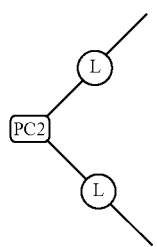
(12-2)

Here, L is defined in the same manner as described above. Further PC1 is a partial structure wherein one kind or a plurality of kinds are subjected to a condensation reaction or addition reaction, or are coordinated onto a metal, to form unit CA or unit CB. Here, PC1 is a partial structure wherein one kind or a plurality of kinds are coordinated onto a metal, to form unit CA or unit CB which comprise a metal complex structure. One kind or a plurality of kinds are subjected to a condensation reaction or addition reaction to form a partial structure forming unit CB.

More specifically, this is dendrimer synthesis method which uses the following formula (12-3) or formula (12-4) as a starting material, to form unit CA or unit CB by condensing, adding or metal-coordinating a multi-branched compound obtained by alternately condensing or adding in sequence one or more of the compounds selected from the compounds represented by the above formulas (10-1) and (11-1) with one or more of the compounds selected from the compounds represented by the above formulas (10-2) and (11-2).

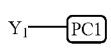
(12-3)

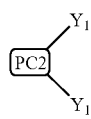
(12-4)

Here, unit Y₁, PC₁ and PC2 are defined in the same manner as above.

Example of the following group in formula (12-1) and formula (12-3),

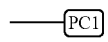

include the groups having the below acetylene skeleton forming a benzene ring from trimerization by an addition reaction, or groups having the below ligand structure.

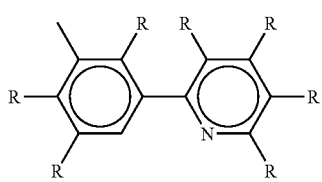

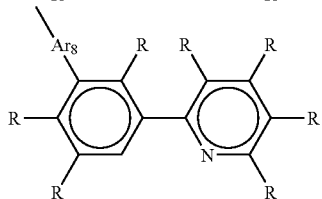

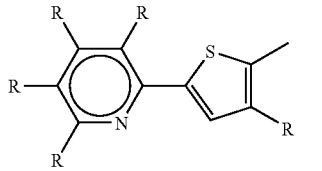

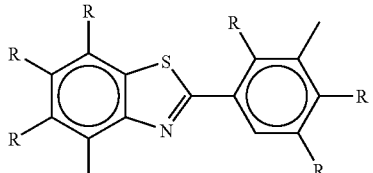

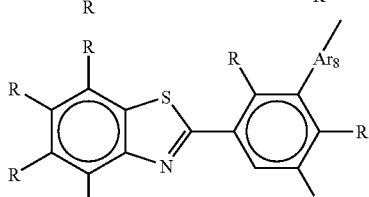

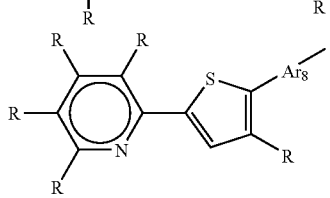

Here, Ar₈ represents a divalent group having a divalent aromatic ring or a metal complex, or a divalent group having the structure represented in the above formula (5).

The second method will now be schematically illustrated. The multi-branched compound represented by the following formula (18-13) can be obtained with a compound represented by the above formula (12-3) as a starter material, by alternately subjecting compounds represented by the above formula (10-1) and formula (10-2) to a condensation reaction or addition reaction.

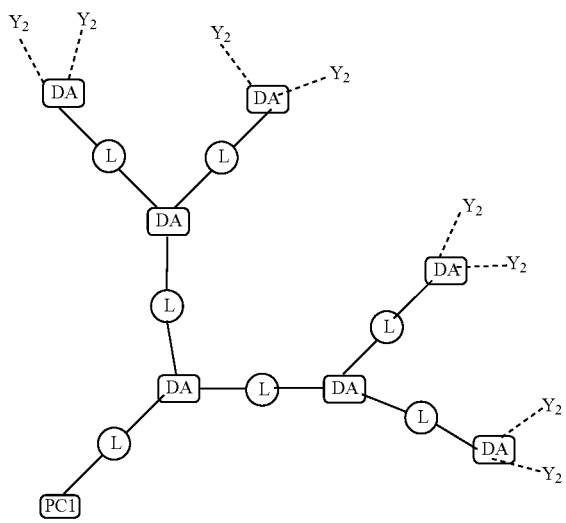

(18-13)

Next, the dendrimer compound represented by formula (18-12) is obtained by subjecting the multi-branched compound represented by formula (18-13) to a condensation reaction, addition reaction or by coordinating onto a metal.

The first method is suitable for a production method of a dendrimer compound having the structure represented by formula (18-1), formula (18-2), formula (18-3), formula (18-4) and formula (18-7). The second method is suitable for a production method of a dendrimer compound having the structure represented by formula (18-5) and formula (18-6).

As the condensation reaction employed in the method for producing a dendrimer compound of the present invention, commonly known condensation reactions can be used in accordance with the substituent group which participates in the condensation reaction. If a double bond is formed in the condensation reaction, the methods disclosed in JP-A-5-202355 can, for example, be used. That is, examples of such a method include a Wittig reaction of a compound having a formyl group with a compound having phosphonium methyl group, or a compound having a formyl group and a phosphonium methyl group; a Heck reaction of a compound having a vinyl group with a compound having a halogen atom; a sulfonium-salt decomposition method of a compound having two or more sulfonium methyl groups; and a McMurry reaction of a compound having two or more formyl groups and the like.

When forming the triple bond of the present invention, a Heck reaction, for example, can be utilized.

When the group participating in the condensation reaction is a halogen atom, alkyl sulfonate group, aryl sulfonate group, or arylalkyl sulfonate group, examples of the condensation reaction include those conducted in the presence of a zero-valent nickel complex such as that of the Yamamoto coupling reaction.

When one group participating in the condensation reaction is a halogen atom, alkyl sulfonate group, aryl sulfonate group, or arylalkyl sulfonate group, and another group participating in the condensation reaction is boric acid or a borate group, examples of the condensation reaction include those conducted using a nickel catalyst or palladium catalyst such as that of the Suzuki coupling reaction.

Further examples include an esterification reaction, amidation reaction, or an etherification reaction of a boric acid group, borate ester group or hydroxyl group.

Of the compounds represented by the above formula (8), formula (9), formula (10-1), formula (10-2), formula (11-1), and formula (11-2), a compound which comprises the structure represented by formula (5) is an important raw material when producing the dendrimer compound of the present invention, especially when producing with the above-described first production method. Such a compound is also effective as the raw material for other multiply dendritic structures or compounds having a multiply dendritic structure.

As the addition reaction employed in the method for producing a dendrimer compound of the present invention, commonly known addition reactions can be used in accordance with the substituent group which participates in the condensation reaction. If one of the groups which participates in the addition reaction is a hydrosilyl group, and the other is a vinyl group or a acetylene group, a hydrosilylation reaction using a transition metal catalyst can be employed.

Preferable examples of such a compound include the compounds represented by following formula (6-4), formula (6-5), formula (6-6), formula (7-5), formula (7-6), formula (7-7) and formula (7-8).

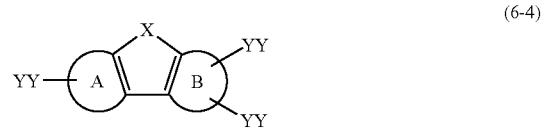

(6-4)

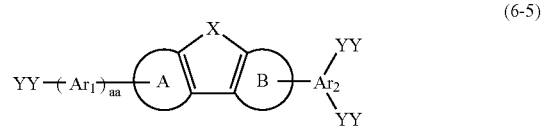

(6-5)

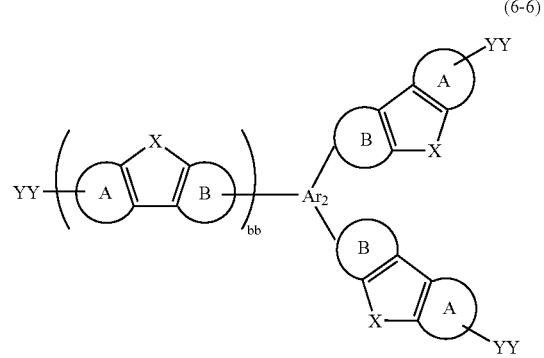

(6-6)

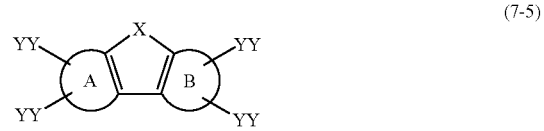

(7-5)

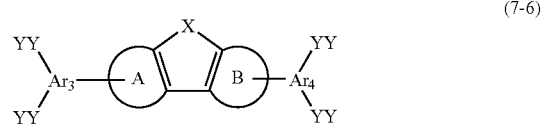

(7-6)

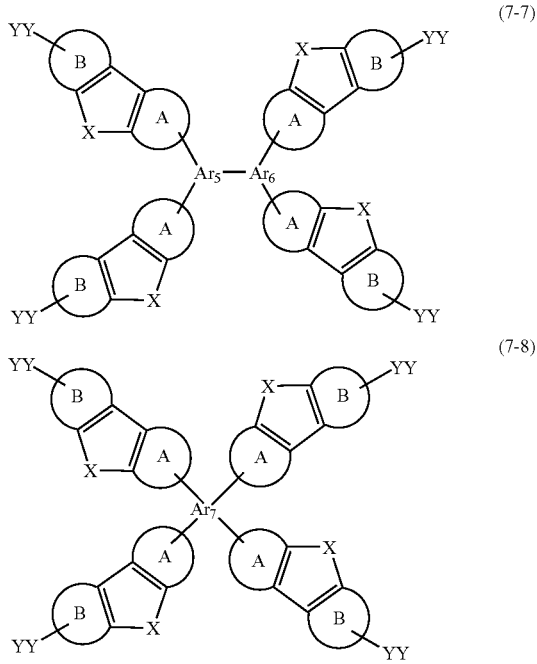

(7-7)

(7-8)

The ring A, ring B and X are defined in the same manner as above. In addition, a preferable range is also the same as that described above. $Ar_1$, $Ar_2$, $Ar_3$, $Ar_4$, $Ar_5$, $Ar_6$, and $Ar_7$, "aa" and "bb" are also defined in the same manner as above. YY is a halogen atom, alkyl sulfonate group, aryl sulfonate group, arylalkyl sulfonate group, boric acid group, borate ester group, sulfonium methyl group, phosphonium methyl group, phosphonate methyl group, monohalogenated methyl group, formyl group, or a group represented by the above (L-3).

The multi-branched compound, which comprises a chemical structure constituted from at least one kind of dendritic structure selected from the dendritic structures represented by the above formula (12-1) or formula (12-2) and the above formula (3) and formula (4) being regularly repeated in three-dimensions, is an important raw material when producing the dendrimer compound of the present invention, especially when producing with the above-described second production method. Such a compound is also effective as the raw material for other multiply dendritic structures or compounds having a multiply dendritic structure.

When a dendrimer compound of the present invention is used as an organic LED, its purity influences device performance, such as luminescence characteristics or the like. Therefore, it is preferable to use the raw material compounds in dendrimer compound production after being purified by a method such as distillation, sublimation purification, re-crystallization or the like. Furthermore, after the dendrimer compound has been produced, it is preferable to conduct a purification operation of separation carried out by reprecipitation purification and chromatography.

Next, application of the dendrimer compound of the present invention will be explained.

The dendrimer compound of the present invention has fluorescence or phosphorescence in its solid state, and can be used as a luminescent body (luminescent material).

This dendrimer compound also has excellent charge transport capacity, and can be preferably used as a material used in organic LEDs and as a charge transport material.

An organic LED which uses this dendrimer compound is a high performance organic LED which can be driven at a low-voltage and high-efficiency.

Therefore, such an organic LED can be preferably used for the back light of a liquid crystal display, a curved or planar light source for lighting, a segment type display device, and an apparatus such as a dot matrix flat panel display.

Moreover, the dendrimer compound of the present invention can also be used as a laser dye, a material used in organic solar cells, an organic semiconductor used for organic transistors, and conductive thin film materials such as luminescent thin films, conductive thin films, organic semiconductor thin films and the like.

Next, the organic LED of the present invention will be explained.

The organic LED of the present invention comprises an organic layer between electrodes consisting of an anode and a cathode, wherein the organic layer comprises the dendrimer compound of the present invention.

The organic layer may be any of a luminescent layer, a hole transporting layer, and an electron transport layer, although it is preferable that the organic layer is a luminescent layer.

Here, a "luminescent layer" means a layer having a function of emitting light, "hole transporting layer" means a layer having a function of transporting holes, and "electron transport layer" means a layer having a function of transporting electrons. The electron transport layer and the hole transporting layer are collectively referred to as "charge transport layer". Two or more layers of the luminescent layer, hole transporting layer, and electron transport layer can be used each independently.

When an organic layer is the luminescent layer, such an organic luminescent layer may further contain a hole transport material, an electron transport material, or a luminescent material. Here, a "luminescent material" means a material which exhibits fluorescence and/or phosphorescence. Moreover, a conjugated polymer having an aromatic ring on its main chain can also be contained.

When mixing the dendrimer compound of the present invention with a hole transport material, the mixing ratio of the hole transport material is 1 wt % to 80 wt % of the total amount of the mixture, and is preferably 5 wt % to 60 wt %. When mixing the dendrimer compound of the present invention with an electron transport material, the mixing ratio of the electron transport material is 1 wt % to 80 wt % of the total amount of the mixture, and is preferably 5 wt % to 60 wt %. Furthermore, when mixing the dendrimer compound of the present invention with a luminescent material, the mixing ratio of the luminescent material is 1 wt % to 80 wt % of the total amount of the mixture, and is preferably 5 wt % to 60 wt %. When mixing the dendrimer compound of the present invention with a luminescent material, a hole transport material, and/or an electron transport material, the mixing ratio of the luminescent material is 1 wt % to 50 wt % of the total amount of the mixture, and preferably 5 wt % to 40 wt %, in which the total amount of the hole transport material and the electron transport material is 1 wt % to 50 wt %, and preferably 5 wt % to 40 wt %. The content of the dendrimer compound of the present invention is 99 wt % to 20 wt %. While the mixing ratio in the composition consisting of the dendrimer compound of the present invention and the conjugated polymer may be determined so as to attain optimum film forming properties and luminescence characteristics, the mixing ratio of the conjugated polymer is 10 wt % to 99 wt % of the total amount of the mixture, and is preferably 10 wt % to 90 wt %.

As the hole transport material, electron transport material, luminescent material, and conjugated polymer to be mixed, known low molecular weight compounds and known polymer compounds can be used, although it is preferable to use known polymer compounds. Examples of hole transport materials, electron transport materials or luminescent materials consisting of a polymer compound include: the polyfluorene and derivatives and copolymers thereof; polyarylene and derivatives and copolymers thereof; polyarylene vinylene and derivatives and copolymers thereof; and (co)polymer of an aromatic amine and derivatives thereof disclosed in WO 99/13692, WO 99/48160, GB 2340304A, WO 00/53656, WO 01/19834, WO 00/55927, GB 2348316 and WO 00/46321, WO 00/06665, WO 99/54943, WO 99/54385, U.S. Pat. No. 5,777,070 and WO 98/06773, WO 97/05184, WO 00/35987, WO 00/53655, WO 01/34722, WO 99/24526, WO 00/22027, WO 00/22026, WO 98/27136, U.S. Pat. No. 573,636 and WO 98/21262, U.S. Pat. No. 5,741,921, WO 97/09394, WO 96/29356, WO 96/10617, EP 0707020 and WO 95/07955, JP-A-2001-181618, JP-A-2001-123156, JP-A-2001-3045, JP-A-2000-351967, JP-A-2000-303066, JP-A-2000-299189, JP-A-2000-252065, JP-A-2000-136379, JP-A-2000-104057, JP-A-2000-80167, JP-A-10-324870, JP-A-10-114891, JP-A-9-111233, JP-A-9-45478, and the like.

Examples of fluorescent materials consisting of a low molecular weight compound include: naphthalene derivatives; anthracene and derivatives thereof, and derivatives thereof; perylene and derivatives thereof; dyes, such as polymethines, xanthenes, coumarins, and cyanines; 8-hydroxyquinoline or a metal complex of its derivatives; aromatic amines; tetraphenylcyclopentadienes or its derivatives; tetraphenylbutadiene or its derivatives, and the like.

Specific examples of compounds that can be used include known materials, such as those disclosed in JP-A-57-51781 or JP-A-59-194393.

The polymer portion of the polymer compound, which is characterized by the dendrimer compound of the present invention being bound with a constituent atom in the main chain structure or side chain of the polymer compound, is preferably the same compound as the known polymer compounds illustrated above.

Examples of phosphorescent compounds consisting of a low molecular weight compound include triplet luminescence complexes such as: Ir(ppy)3 and Btp$_2$Ir(acac) which have iridium as a central metal; PtOEP which has platinum as a central metal; and Eu(TTA)3phen which has europium as a central metal, and the like.

Specific examples of triplet luminescence complexes are disclosed in: Nature, (1998), 395, 151, Appl. Phys. Lett. (1999), 75(1), 4, Proc. SPIE-Int. Soc. Opt. Eng. (2001), 4105 (Organic Light-Emitting Materials and Devices IV), 119, J. Am. Chem. Soc., (2001), 123, 4304, Appl. Phys. Lett., (1997), 71(18), 2596, Syn. Met., (1998), 94(1), 103, Syn. Met., (1999), 99(2), 1361, Adv. Mater., (1999), 11(10), 852, Jpn.J.Appl.Phys.,34, 1883 (1995).

Preferable examples of dendrimer compounds which are mixed with triplet luminescence complexes include, in the structure represented by formula (5), those having only a structure wherein X is —O—, those having only a structure wherein X is —S—, and those having only a structure wherein X is —O— and X is —S—, because their phosphorescence can be effectively utilized and because light emission quantum efficiency is improved.

The composition of the present invention comprises at least one kind of material selected from a hole transport material, an electron transport material, and a luminescent material, and the dendrimer compound of the present invention, and can be used for a luminescent material or a charge transport material. The composition of the present invention may contain two or more of the dendrimer compound of the present invention.

The content ratio of the at least one kind of material selected from a hole transport material, an electron transport material, and a luminescent material, with the dendrimer compound of the present invention can be determined according to the intended use. When used as a luminescent material, the content ratio is preferably the same as that of the above-described luminescent layer.

Regarding the thickness of the luminescent layer in the organic LED of the present invention, its optimum value depends on the material used, and may properly be selected so that the driving voltage and the light emitting efficiency are a suitable value. The thickness is, for example, from 1 nm to 1 μm, preferably from 2 nm to 500 nm, further preferably from 5 nm to 200 nm.

Examples of methods for forming the luminescent layer include methods conducted using film formation from a solution. Examples of film-forming methods from a solution include application methods, such as a spin coat method, casting method, microgravure coating method, gravure coating method, bar-coating method, roll coating method, wire bar coat method, dip coat method, spray coating method, screen printing, flexography method, offset printing, and ink jet printing method, and the like. Printing methods, such as screen printing, flexography method, offset printing, and ink jet printing method, are preferable, since pattern forming and multicolored printing are easy.

As the ink composition used for the printing method or similar method, at least 1 kind of the dendrimer compound of the present invention should be contained, and additives, such as a hole transport material, electron transport material, luminescent material, solvent, or stabilizer, may be contained in addition to the dendrimer compound of the present invention.

The ratio of the dendrimer compound of the present invention in the ink composition is 20 wt % to 100 wt % of the total weight of the composition except the solvent, and preferably 40 wt % to 100 wt %.

When a solvent is contained in the ink composition, the ratio of the solvent is 1 wt % to 99.9 wt % of the total weight of the composition, preferably 60 wt % to 99.5 wt %, and more preferably 80 wt % to 99.0 wt %.

Although a suitable viscosity of the ink composition depends on the printing method, when an ink jet printed or similar ink composition is processed via a discharging apparatus, in order to prevent clogging and curved flight at discharge, the viscosity is preferably in a range of 1 to 20 mPa·s at 25° C.

The solvent used as the ink composition is not especially limited, and preferable are those which can dissolve or uniformly disperse the materials constituting the ink composition other than the solvent. When the materials constituting the ink composition are soluble in a nonpolar solvent, examples of the solvent include: chlorinated solvents, such as chloroform, methylene chloride, and dichloroethane; ether solvents, such as tetrahydrofuran; aromatic hydrocarbon solvents, such as toluene, and xylene; ketone solvents, such as acetone, and methyl ethyl ketone; and ester solvents, such as ethyl acetate, butyl acetate, and ethyl cellosolve acetate.

Moreover, examples of the organic LED of the present invention include: an organic LED having an electron transport layer disposed between a cathode and a luminescent layer; an organic LED having a hole transporting layer disposed between an anode and a luminescent layer; and an organic LED having an electron transport layer disposed between a cathode and a luminescent layer, and a hole transporting layer disposed between an anode and a luminescent layer.

For example, the following structures a) to d) are specific examples.
a) anode/luminescent layer/cathode
b) anode/hole transporting layer/luminescent layer/cathode
c) anode/luminescent layer/electron transport layer/cathode
d) anode/hole transporting layer/luminescent layer/electron transport layer/cathode (wherein, "/" indicates adjacent lamination of layers. Hereinafter, the same)

When the organic LED of the present invention has a hole transporting layer, examples of hole transport materials which can be used include polyvinylcarbazole or derivatives thereof, polysilane or derivatives thereof, polysiloxane derivatives having an aromatic amine in a side chain or main chain, pyrazoline derivatives, arylamine derivatives, stilbene derivatives, triphenyldiamine derivatives, polyaniline or derivatives thereof, polythiophene or derivatives thereof, polypyrrole or derivatives thereof, poly(p-phenylenevinylene) or derivatives thereof, poly(2,5-thienylenevinylene) or derivatives thereof, and the like.

Specific examples of the hole transport material include those described in JP-A-63-70257, JP-A-63-175860, JP-A-2-135359, JP-A-2-135361, JP-A-2-209988, JP-A-3-37992 and JP-A-3-152184.

Among them, preferable examples of the hole transport material used in the hole transporting layer include polymer hole transport materials, such as polyvinylcarbazole or derivatives thereof, polysilane or derivatives thereof, polysiloxane derivatives having an aromatic amine compound group in a side chain or main chain, polyaniline or derivatives thereof, polythiophene or derivatives thereof, poly(p-phenylenevinylene) or derivatives thereof, poly(2,5-thienyleneviny-lene) or derivatives thereof, or the like, and further preferable are polyvinylcarbazole or derivatives thereof, polysilane or derivatives thereof and polysiloxane derivatives having an aromatic amine compound group in a side chain or main chain.

Moreover, examples of a hole transport material consisting of a low molecular weight compound include pyrazoline derivatives, arylamine derivatives, stilbene derivatives, and triphenyl diamine derivatives. In the case of a low molecular weight hole transport material, it is preferably used by dispersing in a polymer binder.

As the polymer binder to be mixed, preferable are those which do not inhibit charge transportation to an extreme extent, and do not have strong absorbance of visible light. Examples of such polymer binders include: poly(N-vinylcarbazole); polyaniline or derivatives thereof; polythiophene or derivatives thereof; poly(p-phenylenevinylene) or derivatives thereof; poly(2,5-thienylenevinylene) or derivatives thereof; polycarbonate; polyacrylate, poly methylacrylate, polymethylmethacrylate, polystyrene, polyvinylchloride, polysiloxane, and the like.

Polyvinyl carbazole and derivatives thereof can be obtained from, for example, a vinyl monomer, by cationic polymerization or radical polymerization.

Examples of polysilane or derivatives thereof include the compounds described in Chem. Rev., 89, 1359 (1989) and GB 2300196 published specification, and the like. The methods described in these documents can be used for the synthesis method, although it is especially preferable to use the Kipping method.

As the polysiloxane or derivatives thereof, compounds which can be preferably used include those having the structure of the above-described low molecular weight hole transport material in a side chain or main chain, since the siloxane skeleton structure has poor hole transportation. Particularly preferable examples include compounds having a hole transporting aromatic amine in their side chain or main chain.

The method for forming a hole transporting layer is not limited. In the case of a low molecular weight hole transporting layer, examples include a method in which the layer is formed from a mixed solution with a polymer binder. In the case of a polymer hole transport material, examples include a method in which the layer is formed from a solution.

The solvent used for film formation from solution is not particularly limited, providing it can dissolve a hole transport material. Examples of such solvent include chlorinated solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, and ester solvents such as ethyl acetate, butyl acetate, ethylcellosolve acetate and the like.

Examples of the film forming method from solution which can be used include coating methods from a solution, such as a spin coating method, casting method, microgravure coating method, gravure coating method, bar coating method, roll coating method, wire bar coating method, dip coating method, spray coating method, screen printing method, flexography method, offset printing method, inkjet printing method and the like.

Regarding the thickness of the hole transporting layer, the optimum value depends on the material used, and may properly be selected so that the driving voltage and the light emitting efficiency are an optimum value. The thickness should be at least such that pinholes are not generated, but not so thick as to undesirably increase the driving voltage of a device. Therefore, the film thickness of the hole transporting layer is, for example, from 1 nm to 1 μm, preferably 2 nm to 500 nm, and more preferably 5 nm to 200 nm.

When the organic LED of the present invention has an electron transport layer, known compounds can be used as the electron transport material. Examples include oxadiazole derivatives, anthraquinodimethane or derivatives thereof, benzoquinone or derivatives thereof, naphthoquinone or derivatives thereof, anthraquinone or derivatives thereof, tetracyanoanthraquinodimethane or derivatives thereof, fluorenone derivatives, diphenyldicyanoethylene or derivatives thereof, diphenoquinone derivatives, or metal complexes of 8-hydroxyquinoline or derivatives thereof, polyquinoline and derivatives thereof, polyquinoxaline and derivatives thereof, polyfluorene or derivatives thereof, and the like.

Specific examples include the compounds described in JP-A-63-70257, JP-A-63-175860, JP-A-2-135359, JP-A-2-135361, JP-A-2-209988, JP-A-3-37992, JP-A-3-152184, and the like.

Among them, preferable are oxadiazole derivatives, benzoquinone or derivatives thereof, anthraquinone or derivatives thereof, or metal complexes of 8-hydroxyquinoline or derivatives thereof, polyquinoline or derivatives thereof, polyquinoxaline or derivatives thereof, and polyfluorene or derivatives thereof, and further preferable are 2-(4-biphenyl)-

5-(4-t-butylphenyl)-1,3,4-oxadiazole, benzoquinone, anthraquinone, tris(8-quinolinol) aluminum and polyquinoline.

The method for forming the electron transport layer is not particularly limited. In the case of a low molecular weight electron transport material, examples include a vapor deposition method from powder, or a method of film-forming from solution or melted state. In the case of a high molecular weight electron transport material, examples include a method of film-forming from solution or melted state. When performing film formation from solution or molten state, the above polymer binder can be used together therewith.

The solvent used in film formation from solution is not particularly limited, provided it can dissolve the electron transport material and/or polymer binder. Examples of such a solvent include chlorinated solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, and ester solvents such as ethyl acetate, butyl acetate, ethylcellosolve acetate and the like.

Examples of the film forming method from solution or melted state which can be used include coating methods such as a spin coating method, casting method, microgravure coating method, gravure coating method, bar coating method, roll coating method, wire bar coating method, dip coating method, spray coating method, screen printing method, flexography method, offset printing method, inkjet printing method and the like.

Regarding the thickness of the electron transport layer, the optimum value depends on the material used, and may properly be selected so that the driving voltage and the light emitting efficiency are an optimum value. The thickness should be at least such that pinholes are not generated, but not so thick as to undesirably increase the driving voltage of a device. Therefore, the film thickness of the hole transporting layer is, for example, from 1 nm to 1 µm, preferably 2 nm to 500 nm, and more preferably 5 nm to 200 nm.

Among charge transport layers provided adjacent to an electrode, those having a function to improve the charge injection efficiency from the electrode and to lower the driving voltage of a device are sometimes commonly called charge injection layers (hole injection layer, electron injection layer) particularly.

To enhance adherence with an electrode and improving charge injection from an electrode, the above-described charge injection layer or insulation layer having a thickness of 2 nm or less may also be provided adjacent to an electrode, and further, for enhancing adherence of the interface, preventing mixing and the like, a thin buffer layer may also be inserted into the interface of a charge transport layer and luminescent layer.

The order and number of layers laminated and the thickness of each layer can be appropriately applied while considering light emitting efficiency and life of the device.

In the present invention, examples of an organic LED provided with a charge injection layer (electron injection layer, hole injection layer) include organic LEDs provided with the charge injection layer adjacent to the cathode and organic LEDs provided with a charge injection layer adjacent to the anode.

Specific examples include the following structures e) to p), for example.
e) anode/charge injection layer/luminescent layer/cathode
f) anode/luminescent layer/charge injection layer/cathode
g) anode/charge injection layer/luminescent layer/charge injection layer/cathode
h) anode/charge injection layer/hole transporting layer/luminescent layer/cathode
i) anode/hole transporting layer/luminescent layer/charge injection layer/cathode
j) anode/charge injection layer/hole transporting layer/luminescent layer/charge injection layer/cathode
k) anode/charge injection layer/luminescent layer/electron transport layer/cathode
l) anode/luminescent layer/electron transport layer/charge injection layer/cathode
m) anode/charge injection layer/luminescent layer/electron transport layer/charge injection layer/cathode
n) anode/charge injection layer/hole transporting layer/luminescent layer/electron transport layer/cathode
o) anode/hole transporting layer/luminescent layer/electron transport layer/charge injection layer/cathode
p) anode/charge injection layer/hole transporting layer/luminescent layer/electron transport layer/charge injection layer/cathode Specific examples of the charge injection layer include: layers containing a conductive polymer; layers which are disposed between an anode and a hole transporting layer and which contain a material having an ionization potential between that of the anode material and the hole transport material contained in the hole transporting layer; and layers which are disposed between a cathode and an electron transport layer and which contain a material having an electron affinity between that of the cathode material and the electron transport material contained in the electron transport layer, and the like.

When the above-described charge injection layer is a layer containing a conductive polymer, the electric conductivity of the conductive polymer is preferably $10^{-5}$ S/cm or more and $10^3$ S/cm or less, and for decreasing the leak current between light emitting pixels, more preferably $10^{-5}$ S/cm or more and $10^2$ S/cm or less, further preferably $10^{-5}$ S/cm or more and $10^1$ S/cm or less.

Usually, in order to make the electrical conductivity of the conductive polymer $10^{-5}$ S/cm or more and $10^3$ S/cm or less, ions are doped into the conductive polymer in an appropriate quantity.

Regarding the kinds of ions to be doped, anions are used for a hole injection layer and cations are used for an electron injection layer. Examples of anions include a polystyrenesulfonate ion, alkylbenzenesulfonate ion, camphor sulfonate ion and the like. Examples of cations include a lithium ion, sodium ion, potassium ion, tetrabutyl ammonium ion and the like.

The thickness of the charge injection layer is for example, from 1 nm to 100 nm, and is preferably from 2 nm to 50 nm.

Materials used as the charge injection layer can be appropriately selected in view of their relationship with the electrode or material of the adjacent layer. Examples include conductive polymers, such as polyaniline and derivatives thereof, polythiophene and derivatives thereof, polypyrrole and derivatives thereof, polyphenylenevinylene and derivatives thereof, polythienylenevinylene and derivatives thereof, polyquinoline and derivatives thereof, polyquinoxaline and derivatives thereof, and polymers which contain an aromatic amine structure in a main chain or side chain, metal phthalocyanines (e.g. copper phthalocyanine and the like), carbon, and the like.

The insulation layer having a thickness of 2 nm or less has a function of facilitating charge injection. Examples of the material for the insulating layer include a metal fluoride, metal oxide, organic insulating material, and the like. Examples of organic LEDs having a 2 nm thick or less insulation layer include an organic LED containing an insulation layer having a thickness of 2 nm or less adjacent to the cathode, and an organic LED containing an insulation layer having a thickness of 2 nm or less adjacent to the anode.

Specific examples include the following structures q) to ab), for example.

q) anode/insulation layer having a thickness of 2 nm or less/luminescent layer/cathode
r) anode/luminescent layer/insulation layer having a thickness of 2 nm or less/cathode
s) anode/insulation layer having a thickness of 2 nm or less/luminescent layer/insulation layer having a thickness of 2 nm or less/cathode
t) anode/insulation layer having a thickness of 2 nm or less/hole transporting layer/luminescent layer/cathode
u) anode/hole transporting layer/luminescent layer/insulation layer having a thickness of 2 nm or less/cathode
v) anode/insulation layer having a thickness of 2 nm or less/hole transporting layer/luminescent layer/insulation layer having a thickness of 2 nm or less/cathode
w) anode/insulation layer having a thickness of 2 nm or less/luminescent layer/electron transport layer/cathode
x) anode/luminescent layer/electron transport layer/insulation layer having a thickness of 2 nm or less/cathode
y) anode/insulation layer having a thickness of 2 nm or less/luminescent layer/electron transport layer/insulation layer having a thickness of 2 nm or less/cathode
z) anode/insulation layer having a thickness of 2 nm or less/hole transporting layer/luminescent layer/electron transport layer/cathode
aa) anode/hole transporting layer/luminescent layer/electron transport layer/insulation layer having a thickness of 2 nm or less/cathode
ab) anode/insulation layer having a thickness of 2 nm or less/hole transporting layer/luminescent layer/electron transport layer/insulation layer having a thickness of 2 nm or less/cathode The substrate forming the organic LED of the present invention should be a substrate that does not change during formation of the electrodes or organic layer. Examples include glass, plastic, polymer film, silicon substrates and the like. In the case of an opaque substrate, it is preferable that the opposite electrode is transparent or semitransparent.

Usually, at least one of the anode or the cathode in the organic LED of the present invention is transparent or semitransparent. It is preferable that the anode side is transparent or semitransparent.

Conductive metal oxide films, semitransparent metal thin films and the like can be used as the material for such an anode. Specific examples of materials that can be used include indium oxide, zinc oxide, tin oxide, and films (NESA and the like) fabricated by using a conductive glass composed of indium-tin oxide (ITO), indium-zinc oxide and the like, which are complexes of the above materials, and gold, platinum, silver, copper and the like. Among them, ITO, indium-zinc oxide, and tin oxide are preferable. Examples of the fabricating method include a vacuum vapor deposition method, sputtering method, ion plating method, plating method and the like. Organic transparent conductive films can be used as the anode, such as polyaniline or derivatives thereof, polythiophene or derivatives thereof and the like.

The thickness of the anode can be appropriately selected taking into consideration light transmission characteristics and the degree of electric conductivity, and can be, for example, from 10 nm to 10 μm, preferably from 20 nm to 1 μm, and more preferably from 50 nm to 500 nm.

Further, to facilitate charge injection, the anode can be provided with a layer comprising a phthalocyanine derivative, a conductive polymer, carbon or the like, or a layer having an average film thickness of 2 nm or less comprising a metal oxide, metal fluoride, organic insulating material or the like.

A material having a low work function is preferable as the cathode material used in the organic LED of the present invention. Examples include metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like; alloys comprising two of more of these metals; alloys comprising one or more of these metals with one or more of gold, silver, platinum, copper, manganese, titanium, cobalt, nickel, tungsten and tin; graphite or graphite intercalation compounds and the like. Examples of alloys include a magnesium-silver alloy, magnesium-indium alloy, magnesium-aluminum alloy, indium-silver alloy, lithium-aluminum alloy, lithium-magnesium alloy, lithium-indium alloy, calcium-aluminum alloy and the like. The cathode may be formed into a laminated structure of two or more layers.

The thickness of the cathode can be appropriately selected taking into consideration light transmission characteristics and the degree of electric conductivity, and can be, for example, from 10 nm to 10 μm, preferably from 20 nm to 1 μm, and more preferably from 50 nm to 500 nm.

Examples of the method for fabricating the cathode include a vacuum vapor deposition method, sputtering method, lamination method in which a metal thin film is adhered under heat and pressure, and the like. Further, between the cathode and the organic layer, there may also be provided a layer comprising a conductive polymer, or a layer having an average film thickness of 2 nm or less comprising a metal oxide, metal fluoride, organic insulation material and the like. After fabrication of the cathode, a protective layer may also be provided which protects the organic LED. For stable long term use of the organic LED, it is preferable to provide a protective layer and/or protective cover for protection of the device in order to prevent it from external damage.

For this protective layer, materials that can be used include polymer compounds, metal oxides, metal fluorides, metal borides and the like. For the protective cover, materials that can be used include glass plate, plastic plate whose surface has been subjected to a low-water-permeation treatment, and the like. A preferable method that can be used seals by pasting the cover with a device substrate using a heat curing resin or photocuring resin. If space is maintained using a spacer, it is easy to prevent a device from being damaged. By filling this space with an inert gas such as nitrogen or argon, it is possible to prevent oxidation of the cathode. In addition, by placing a desiccant such as barium oxide or the like in the above-described space, it is easy to suppress damage to a device from moisture adhered in the production process. It is preferable to adopt any one or more of these measures.

The organic LED of the present invention can be used as a planar light source, segment display device, dot matrix display device, and back light of a liquid crystal display.

To achieve a planar light emission using the organic LED of the present invention, a planar anode and cathode can be placed so that they overlap each other. Further, to achieve a patterned light emission, methods which can be used include: a method which places a mask provided with a patterned window on the above-described planar light emitting device; a method which essentially effects non-light emission by forming an extremely thick non-luminescent portion organic layer; and a method which forms either the anode or the cathode, or both electrodes, in a pattern. By using any of these methods to form a pattern, and by placing some electrodes so that they can be independently turned on/off, a segment type display device can be obtained which is capable of displaying digits, letters, simple marks and the like. Further, to form a dot matrix device, the anodes and cathodes can be placed in a striped manner so as to cross at right angles. Area color displays and multi color displays are made possible from a method in which a plurality of kinds of polymer compounds emitting different colors of lights are placed separately or a method in which a color filter or luminescence converting filter is used. A dot matrix display can be driven by passive driving, or by active driving combined with TFT and the like. These display devices can be used as a display of a computer, television, portable terminal, portable telephone, car navigation, view finder of a video camera, and the like.

Further, the above-described planar light emitting device is thin and self-light-emitting, and can be suitably used as a planar light source for back-light of a liquid crystal display, or as a planar light source for illumination. Further, if a flexible plate is used, it can also be used as a curved light source or a display.

The following examples further illustrate the present invention in detail but do not limit the scope thereof.

EXAMPLE 1

Synthesis of Intermediate D

Under an argon atmosphere, raw material A (1 g, 1.7 mmol), raw material B(0.861 g, 1.8 mmol), and bis(triphenylphosphine)palladium(II) dichloride (65 mg, 0.09 mmol) were weighed out and charged into a 100 mL three-necked flask, and anhydrous THF (20 mL) was charged into this mixture. The resulting solution was cooled with ice. Once the solution was sufficiently cooled, 3M aqueous sodium hydroxide (5 mL) was charged thereto under stirring. While cooling with ice, the solution was cooled for 7 hours, after which water and chloroform were added and the solution separated out. The organic layer was separated with brine, and then dried using sodium sulfate. The drying agent was filtered off, and the solvent was removed by distillation, whereby intermediate D (570 mg, 39.7%) was obtained as a white solid by silica gel chromatography.

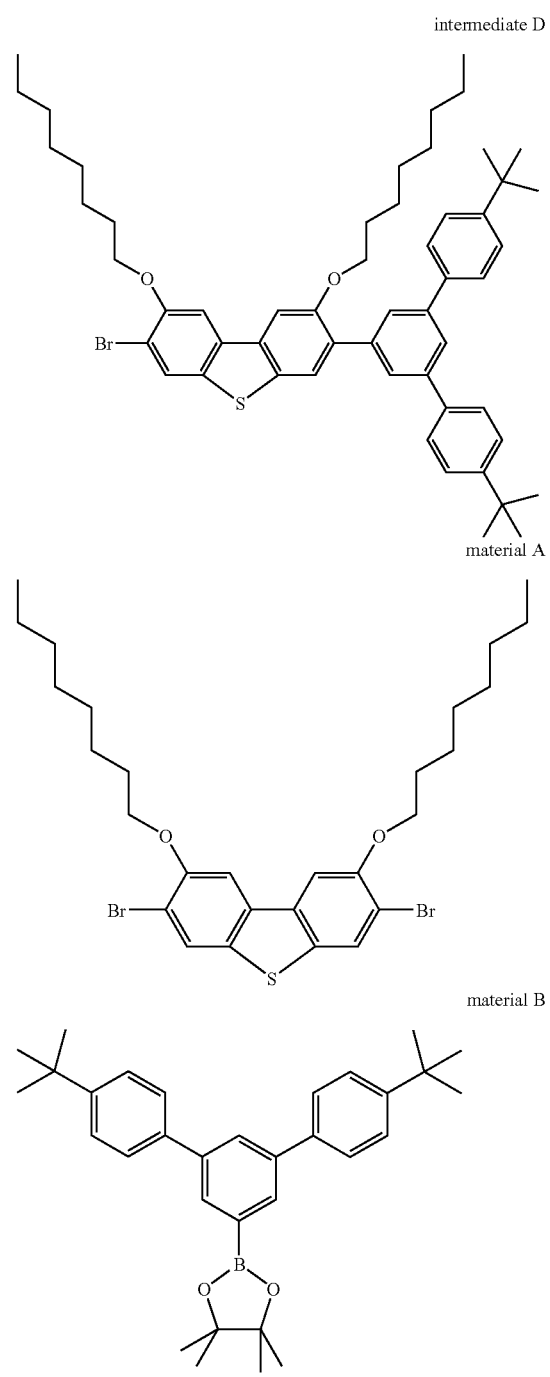

intermediate D material A material B $^1$H-NMR (300 MHz/CDCl$_3$): δ 7.99 (s, 1H), 7.82-7.80 (m, 4H), 7.66-7.60 (m, 5H), 7.55-7.48 (m, 5H), 4.22-4.13 (m, 4H), 1.97-1.81 (m, 4H), 1.60-1.55 (m, 6H), 1.38 (s, 18H), 1.32-1.20 (m, 12H), 0.87-0.82 (m, 8H)

Raw material A was synthesized in accordance with a method disclosed in JP-A-2004-043544, and raw material B was synthesized in accordance with a method disclosed in WO 02/066552.

Synthesis of Intermediate E

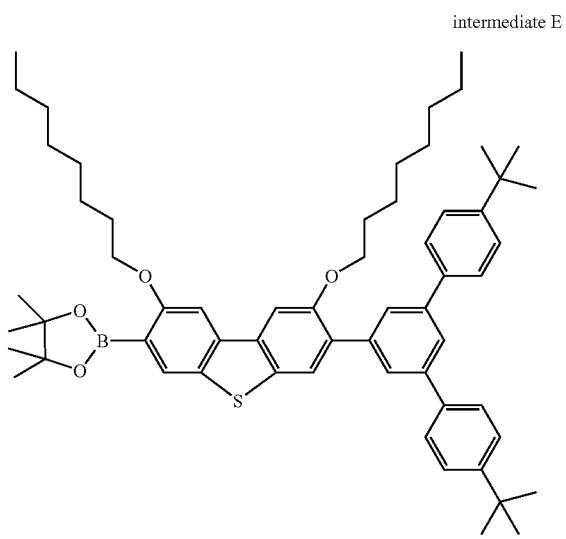 [SMILES: CCCCCCCCOc1cc2c(cc1B1OC(C)(C)C(C)(C)O1)sc1cc(-c3cc(-c4ccc(C(C)(C)C)cc4)cc(-c4ccc(C(C)(C)C)cc4)c3)c(OCCCCCCCC)cc12]

intermediate E

Under an argon atmosphere, raw material D (265 mg, 0.31 mmol) was weighed out and charged into a 100 mL three-necked flask, and THF (10 mL) was charged thereto. The resulting solution was cooled to −78° C., and then dropped with a n-BuLi hexane solution (2.4 M, 0.17 mL, 0.40 mmol). Once the dropping was finished, the resulting solution was stirred for 15 minutes with the temperature being held at the above level. Isopropoxypinacol borane (0.07 g, 0.04 mmol) was added thereto, and the mixture was stirred at −78° C. for 4 hours. This reaction solution was quenched with water. The resulting solution was charged with chloroform and the organic layer was separated out. The organic layer was further separated with brine, and then dried using sodium sulfate. The drying agent was filtered off, and then the solvent was removed by distillation under reduced pressure, whereby a crude refined product was obtained. This compound was used in the following reaction without undergoing the above-described purification.

$^1$H-NMR (300 MHz/CDCl$_3$): δ 8.10 (s, 1H), 7.86-7.79 (m, 4H), 7.66-7.63 (m, 5H), 7.50-7.47 (m, 5H), 4.19-4.10 (m, 4H), 1.90-1.80 (m, 4H), 1.62-1.56 (m, 6H), 1.55 (s, 12H), 1.38 (s, 18H), 1.33-1.20 (m, 12H), 0.90-0.82 (m, 8H)

Synthesis of Dendrimer F

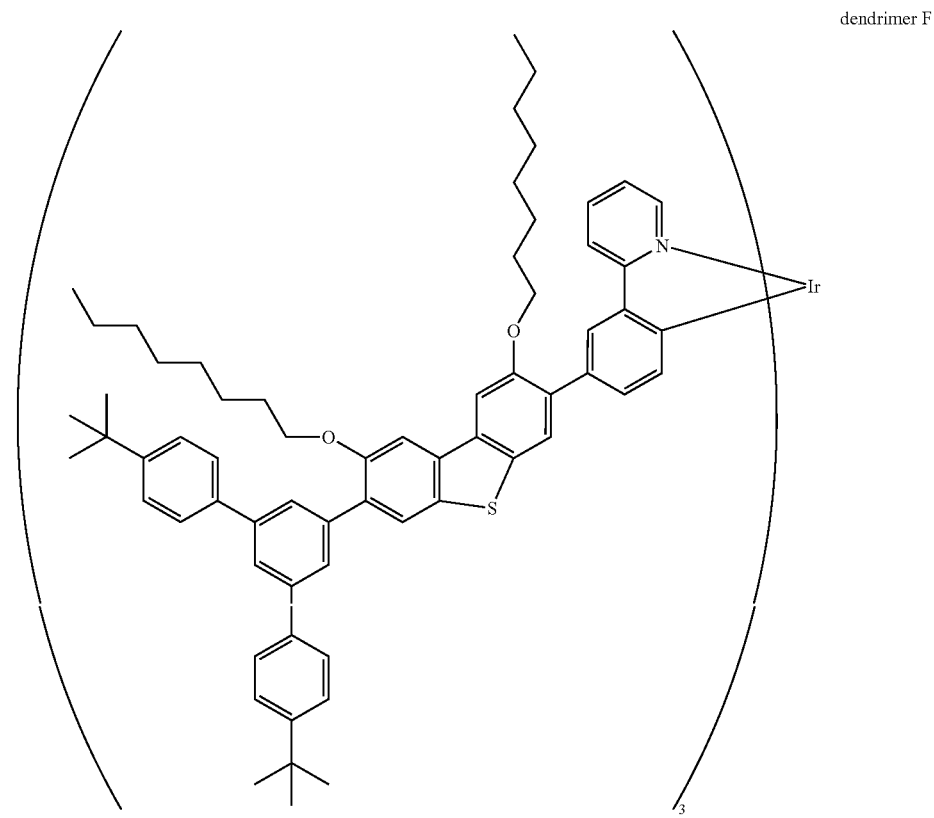

dendrimer F

Under an argon atmosphere, intermediate C (50 mg, 0.06 mmol), compound E (340 mg) and bis(triphenylphosphine)palladium(II) dichloride (30 mg, 0.04 mmol) were weighed out and charged into a 100 mL three-necked flask, and the resulting mixture was charged with THF (10 mL). This solution was charged with aqueous tetraethylammonium hydroxide (1.3 mL), and the resulting solution was heated to reflux. Once the reaction was finished, water and chloroform were added and the solution separated out. The organic layer was separated with brine, and then dried using sodium sulfate. After filtering, the solvent was removed by distillation under reduced pressure, whereby dendrimer F (80 mg) was obtained by separating using silica gel chromatography. This dendrimer F also contained compound F-1 and compound F-2.

MALDI TOF-MS:

M/Z=2991 (M⁺, dendrimer F), 2291 (M⁺, compound F-1), 1591 (M⁺, compound F-2)

intermediate C

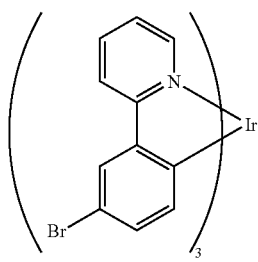

compound (F-1)

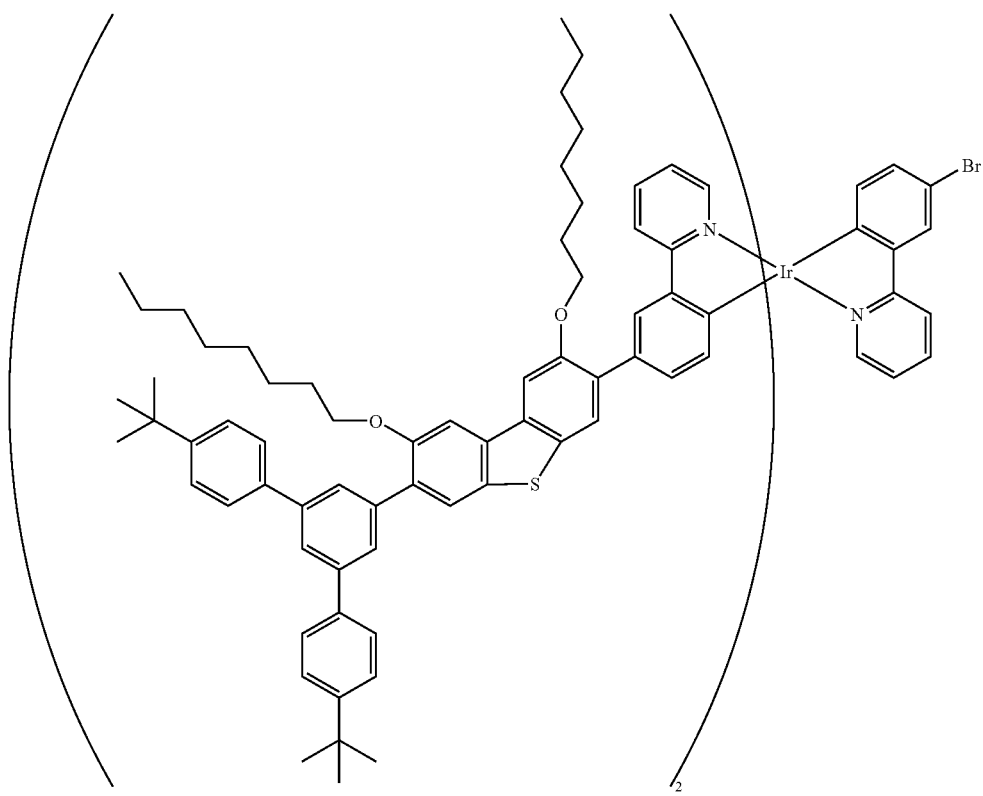

-continued

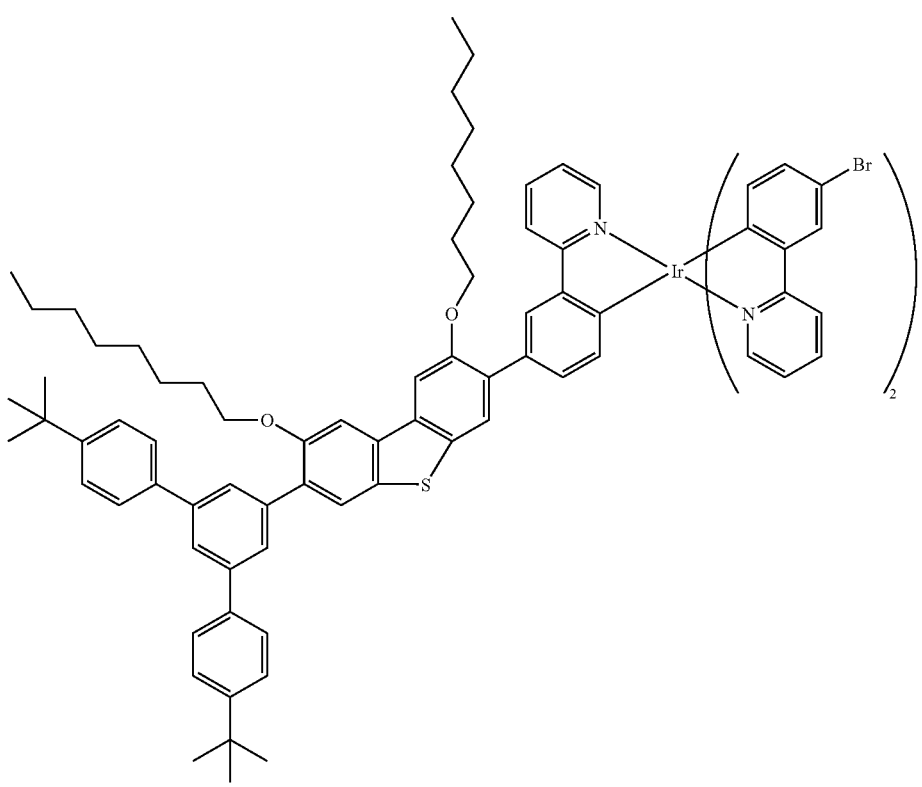

compound (F-2)

Intermediate C was obtained by brominating fac-tris-(2-(phenyl)pyridinato,N,C²')iridium(III) by a common brominating method of an aromatic organic compound.

$^1$H-NMR (300 MHz/CDCl$_3$): δ 0.85 (d, J=8.1 Hz, 3H), 7.74 (t, J=7.8 Hz, 3H), 7.48 (d, J=9 Hz, 3H), 7.47 (d, J=4.8 Hz, 3H), 6.98-6.90 (m, 6H) 6.66 (d, J=8.1 Hz, 3H)

EXAMPLE 2

A 1.0 wt % by weight chloroform solution of the dendrimer F obtained in Example 1 was prepared.

On a glass substrate which had a 150 nm thick ITO film deposited by sputtering, a 50 nm thick film was formed by spin coating using a solution of poly(ethylenedioxythiophene)/polystyrene sulfonic acid (BaytronP, Bayer) and dried for 10 minutes on a hot plate at 200° C. Next, a film was formed by spin coating at a revolution rate of 1,500 rpm using the above-prepared chloroform solution. The film thickness was about 80 nm. The film was dried under reduced pressure at 80° C. for 1 hour. The dried film was then subjected to vapor deposition to form about 4 nm of LiF as the cathode buffer layer, and about 5 nm of calcium followed by about 80 nm of aluminum as the cathode, to thereby fabricate an EL device. It should be noted that the metal vapor deposition was started after the degree of vacuum had reached 1×10$^{-4}$ Pa or below. When voltage was applied to the thus-obtained device, EL luminance was obtained with a peak at 515 nm.

EXAMPLE 3

A 1.0 wt % by weight chloroform solution of the dendrimer F obtained in Example 1 was prepared in which 20 wt. % of the below compound 2 had been added. Using this solution, an EL device was obtained in the same manner as that described for Example 2. Spin coating of the solution was performed at 3,000 rpm, and the film thickness was about 85 nm. When voltage was applied to the thus-obtained device, EL luminance was obtained with a peak at 515 nm. The device exhibited a luminance of 100 cd/m² at 12.4 V. Maximum luminance efficiency was 0.63 cd/A. Compound 2 was purchased from Aldrich.

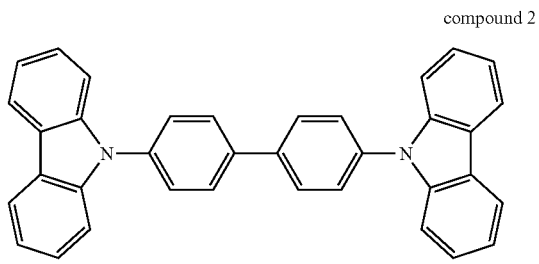 [SMILES: c1ccc2c(c1)c1ccccc1n2-c1ccc(-c2ccc(-n3c4ccccc4c4ccccc43)cc2)cc1]

compound 2

EXAMPLE 4

Synthesis of Dendrimer G

The byproducts obtained during the synthesis of intermediate D were separated by silica gel chromatography, and then recrystallized from a chloroform/acetonitrile solution, whereby 180 mg of dendrimer G was isolated.

dendrimer G

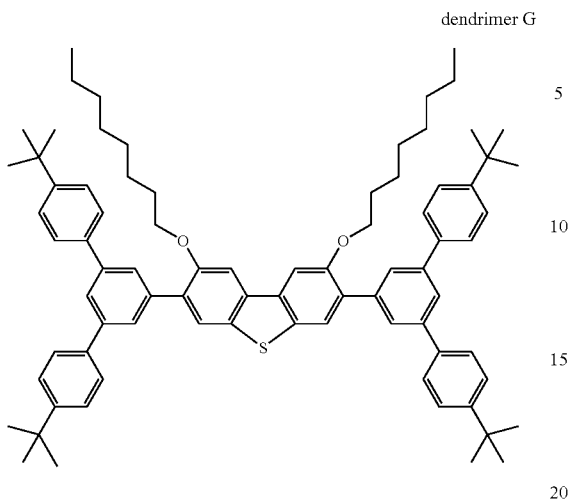

$^1$H-NMR (300 MHz/CDCl$_3$): δ 7.88-7.68 (m, 8H), 7.68-7.65 (m, 10H), 7.51-7.48 (m, 8H), 4.19 (t, J=5.7 Hz, 4H), 1.60-1.55 (m, 6H), 1.38 (s, 18H), 1.29-1.21 (m, 22H), 0.87-0.82 (m, 8H)

EXAMPLE 5

A 1.0 wt % by weight chloroform solution of the dendrimer G obtained in Example 4 was prepared.

Using this solution, an EL device was obtained in the same manner as that described for Example 2. Spin coating of the solution was performed at 3,000 rpm, and the film thickness was about 100 nm. When voltage was applied to the thus-obtained device, EL luminance was obtained with a peak at 400 nm.

The invention claimed is:

1. A dendrimer compound characterized by comprising a core represented by the following formula (1-3) and at least one dendritic structure selected from dendritic structures represented by the following formula (3) or (4):

(1-3)

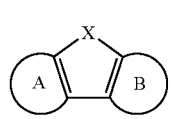

(3)

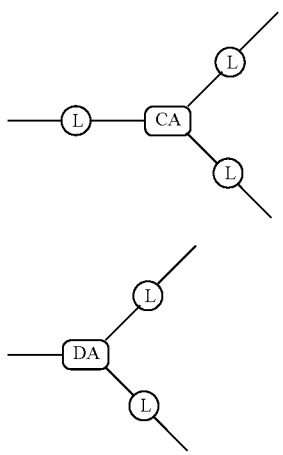

(4)

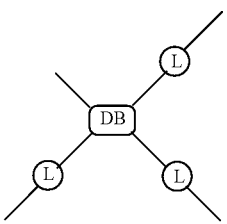

wherein a unit CA represents an aromatic ring, a metal complex structure, a structure represented by the following formula (5):

(5)

wherein a ring A and a ring B each independently represent an aromatic ring, X represents —O—, —S—, —S(=O)—, —SO$_2$—, —B(R$_1$)—, —Si(R$_2$)(R$_3$)— or —PR$_5$(=O)—, and R$_1$, R$_2$, R$_3$, R$_4$ and R$_5$ each independently represent a substituent selected from an alkyl group, an alkoxy group, an alkylthio group, an aryl group, an aryloxy group, an arylthio group, an arylalkyl group, an arylalkoxy group, an arylalkylthio-group, an arylalkenyl group, an arylalkynyl group, an amino group, a substituted amino group and a monovalent heterocyclic group,
or a structure in which two or more structures selected from an aromatic ring, a metal complex structure and a structure represented by the above formula (5), which may be the same or different, are bonded directly or via a divalent group shown in the following (L-1):

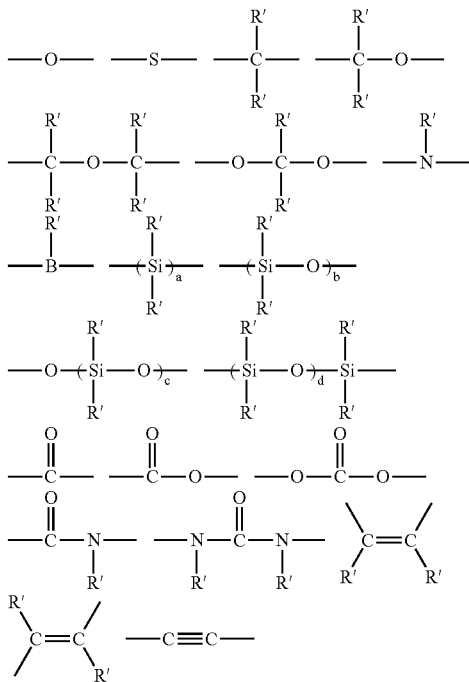

wherein W represents a group selected from a hydrogen atom, an alkyl group, an alkoxy group, an aryl group and an aryloxy group, and when a plurality of R's are present, R's may be the same or different; a, b and c each independently represent an integer of 1 to 12; and d represents an integer of 1 to 11;
  a unit DA and a unit DB each independently represent an aromatic ring, a metal complex structure, a structure represented by the above formula (5), or a structure in which two or more structures selected from an aromatic ring, a metal complex structure and a structure represented by the above formula (5), which may be the same or different, are bonded;
  at least one of the core and the dendritic structure contains a structure represented by the formula (5);
  L is a direct bond or a linking group selected from the following (L-2):

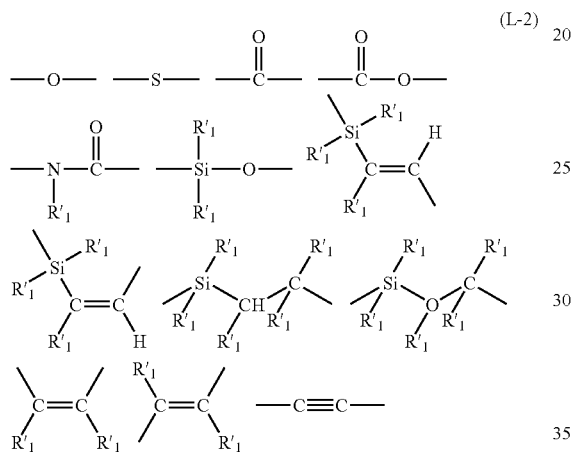

(L-2)

wherein $R_1'$ represents a hydrogen atom, an alkyl group, an alkoxy group, an aryl group or an aryloxy group, and when a plurality of $R_1'$'s are present, $R_1'$'s may be the same or different; and
  at least one of the core unit and the unit in the dendritic structure has a metal complex structure; and
  wherein the central metal of the complex is selected from the group consisting of aluminum, zinc, beryllium, ruthenium, rhodium, iridium, platinum, gold, europium, and terbium.

2. The dendrimer compound according to claim 1, wherein the unit CA contains a metal complex structure.

3. The dendrimer compound according to claim 1, whose number of generations is 1 to 5.

4. The dendrimer compound according to claim 1, comprising a chemical structure in which at least one dendritic structure selected from dendritic structures represented by the formula (3) and the formula (4) is regularly repeated.

5. The dendrimer compound according to claim 1, wherein the core represented by the formula (1-3) is represented by the following formula (7-1), (7-2) or (7-3):

(7-1)

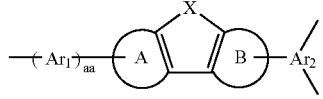

(7-2)

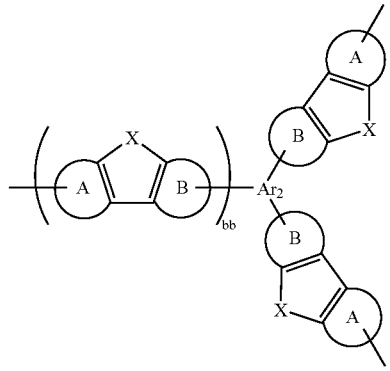

(7-3)

wherein the ring A, the ring B and X are as defined above; $Ar_1$ represents a divalent aromatic ring or a divalent metal complex structure; $Ar_2$ represents a trivalent aromatic ring or a trivalent metal complex structure; and aa and bb each independently represent 0 or 1.

6. The dendrimer compound according to claim 1, wherein the dendritic structure represented by the formula (3) is represented by the following formula (7-1), (7-2) or (7-3):

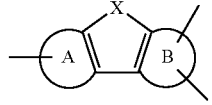

(7-1)

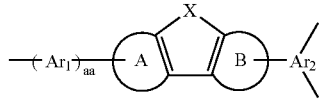

(7-2)

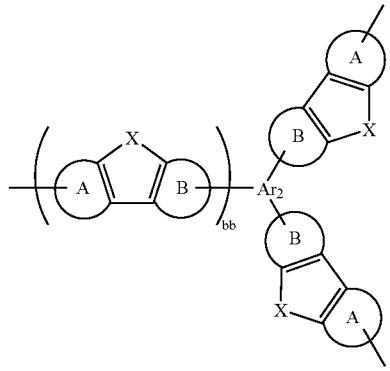

(7-3)

wherein the ring A, the ring B and X are as defined above; $Ar_1$ represents a divalent aromatic ring or a divalent metal complex structure; $Ar_2$ represents a trivalent aromatic ring or a trivalent metal complex structure; and aa and bb each independently represent 0 or 1.

7. The dendrimer compound according to claim 1, wherein the dendritic structure represented by the formula (4) is represented by the following formula (8-1), (8-2), (8-3) or (8-4):

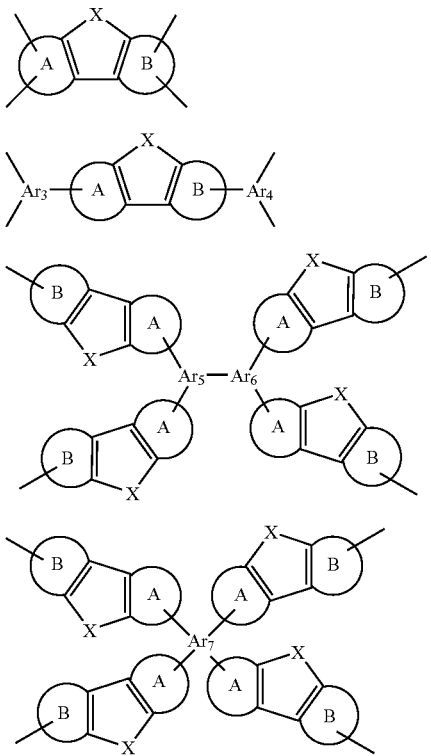

(8-1)
(8-2)
(8-3)
(8-4)

wherein the ring A, the ring B and X are as defined above; $Ar_3$, $Ar_4$, $Ar_5$ and $Ar_6$ each independently represent a trivalent aromatic ring or a trivalent metal complex structure; and $Ar_7$ represents a tetravalent aromatic ring or a tetravalent metal complex structure.

8. The dendrimer compound according to claim 1, wherein the ring A and the ring B are an aromatic hydrocarbon ring.

9. The dendrimer compound according to claim 1, wherein at least one of the core and the dendritic structure contains a metal complex structure.

10. The dendrimer compound according to claim 1, further comprising a surface group in addition to the core and the dendritic structure.

11. A polymer compound characterised by comprising the dendrimer according to claim 1 bonded to an atom constituting the main chain structure or a side chain of the polymer compound.

12. A composition characterized by comprising the dendrimer compound according to any one of claims 1, 2 to 4, 5, 6 to 10 and/or the polymer compound according to claim 11, and a conjugated polymer compound containing an aromatic ring in the main chain.

13. A composition characterized by comprising at least one material selected from a hole transport material, an electron transport material and a luminescent material, and the dendrimer, the polymer compound or the composition according to claim 1.

14. The composition according to claim 13, further comprising at least one material selected from a hole transport material, an electron transport material and a luminescent material.

15. An ink composition characterized by comprising the dendrimer compound, the polymer compound or the composition according to claim 1.

16. The ink composition according to claim 15, having a viscosity of 1 to 100 mPa·s at 25° C.

17. A luminescent thin film characterized by comprising the dendrimer compound or the composition according to claim 1.

18. A conductive thin film characterized by comprising the dendrimer compound or the composition according to claim 1.

19. An organic semiconductor thin film characterized by comprising the dendrimer compound or the composition according to claim 1.

20. An organic luminescent device characterized by comprising a layer containing the dendrimer compound or the composition according to claim 1 between electrodes of an anode and a cathode.

21. The organic luminescent device according to claim 19, wherein the layer containing the dendrimer compound or the composition according to any one of claims 1 to 14 is a luminescent layer.

22. A planar light source characterized by comprising the organic luminescent device according to claim 20.

23. A segment display device characterized by comprising the organic luminescent device according to claim 20.

24. A dot matrix display device characterized by comprising the organic luminescent device according to claim 20.

25. A liquid crystal display device characterized by comprising the organic luminescent device according to claim 20 as a backlight.

26. An illumination characterized by comprising the organic luminescent device according to claim 20.

27. The dendrimer compound according to claim 1, wherein the core is represented by formula (1-3) and the dendritic structure is represented by formula (3).

* * * * *